US010682367B2

(12) United States Patent
Fuchs et al.

(10) Patent No.: US 10,682,367 B2
(45) Date of Patent: Jun. 16, 2020

(54) ANTITUMOR ARYLNAPHTHALENE LIGAND GLYCOSIDES

(71) Applicant: OHIO STATE INNOVATION FOUNDATION, Columbus, OH (US)

(72) Inventors: James Fuchs, Columbus, OH (US); Alan Douglas Kinghorn, Columbus, OH (US); Andrew Huntsman, Fort Jennings, OH (US)

(73) Assignee: OHIO STATE INNOVATION FOUNDATION, Columbus, OH (US)

( * ) Notice: Subject to any disclaimer, the term of this patent is extended or adjusted under 35 U.S.C. 154(b) by 0 days.

(21) Appl. No.: 16/079,754

(22) PCT Filed: Apr. 26, 2017

(86) PCT No.: PCT/US2017/029625
§ 371 (c)(1),
(2) Date: Aug. 24, 2018

(87) PCT Pub. No.: WO2017/147624
PCT Pub. Date: Aug. 31, 2017

(65) Prior Publication Data
US 2019/0054105 A1  Feb. 21, 2019

Related U.S. Application Data

(60) Provisional application No. 62/300,306, filed on Feb. 26, 2016.

(51) Int. Cl.
| | | |
|---|---|---|
| *A01N 43/04* | (2006.01) | |
| *A61K 31/70* | (2006.01) | |
| *A61K 31/7048* | (2006.01) | |
| *A61K 45/06* | (2006.01) | |
| *C07H 17/08* | (2006.01) | |
| *A61P 35/00* | (2006.01) | |
| *A61K 31/365* | (2006.01) | |

(52) U.S. Cl.
CPC ........ *A61K 31/7048* (2013.01); *A61K 31/365* (2013.01); *A61K 45/06* (2013.01); *A61P 35/00* (2018.01); *C07H 17/08* (2013.01); *A61K 2121/00* (2013.01)

(58) Field of Classification Search
None
See application file for complete search history.

(56) References Cited

U.S. PATENT DOCUMENTS

| | | |
|---|---|---|
| 4,771,072 A | 9/1988 | Iwasaki et al. |
| 6,130,094 A | 10/2000 | Waggoner et al. |
| 2013/0295207 A1 | 11/2013 | Kikuchi et al. |
| 2014/0088186 A1 | 3/2014 | Yang et al. |

FOREIGN PATENT DOCUMENTS

| | | |
|---|---|---|
| WO | 2013/019662 | 2/2013 |
| WO | 2015/153653 A1 | 10/2015 |

OTHER PUBLICATIONS

Abdullaev, N., Yagudaev, M., Batirov, E., & Malikov, V. (1987). C-13 Nmr-Spectra of Arulnaphthaline Lignans. Khimiya Prirodnykh Soedinenii, (1), 76-90.
Al-Abed Y. et al., "A arylnaphthalene lignan from Haplophyllum buxbaumii", Phytochemistry 1998, 49, 1779-1781.
Al-Abed, Y., Sabri, S., Zarga, M. A., & Shah, Z. (1990). Chemical constituents of the Flora of Jordan, Part VB. Three new arylnaphthalene lignan glucosides from Haplophyllum buxbaumii. Journal of natural products, 53(5), 1152-1161.
Amos, S. M. et al. (2011). Autoimmunity associated with immunotherapy of cancer. Blood, 118(3), 499-509.
Anjaneyulu, A. S. R., Ramaiah, P. A., Row, L. R., Venkateswarlu, R., Pelter, A., & Ward, R. S. (1981). New lignans from the heartwood of Cleistanthus collinus. Tetrahedron, 37(21), 3641-3652.
Atta-ur-Rahman, et al., Antifungal aryltetralin lignans from leaves of Podophyllum hexandrum, Phytochemistry 1995, 40, 427-431.
Bachmeyer, C., Mak, C. H., Yu, C. Y., & Wu, L. C. (1999). Regulation by phosphorylation of the zinc finger protein KRC that binds the κB motif and V (D) J recombination signal sequences. Nucleic acids research, 27(2), 643-648.
Baer, M. R. et al. (2008). Low-dose interleukin-2 immunotherapy does not improve outcome of patients age 60 years and older with acute myeloid leukemia in first complete remission: Cancer and Leukemia Group B Study 9720. Journal of Clinical Oncology, 26(30), 4934-4939.
Barge et al., Pharmaceutical salts. J. Pharm. Sci. (1977) 66, 1-9.
Bindseil, K. U., Jakupovic, J., Wolf, D., Lavayre, J., Leboul, J., & van der Pyl, D. (2001). Pure compound libraries; a new perspective for natural product based drug discovery. Drug Discovery Today, 6(16), 840-847.
Broomhead, A. J., & Dewick, P. M. (1990). Aryltetralin lignans from Linum flavum and Linum capitatum. Phytochemistry, 29(12), 3839-3844.
Burla, M. C. et al. (2005). SIR2004: an improved tool for crystal structure determination and refinement. Journal of Applied Crystallography, 38(2), 381-388.
Caligiuri, M. A. (2008). Human natural killer cells. Blood, 112(3), 461-469.
Chang, H. C., Han, L., Goswami, R., Nguyen, E. T., Pelloso, D., Robertson, M. J., & Kaplan, M. H. (2009). Impaired development of human Th1 cells in patients with deficient expression of STAT4. Blood, 113(23), 5887-5890.
Charlton, J. L., Oleschuk, C. J., & Chee, G. L. (1996). Hindered rotation in arylnaphthalene lignans. The journal of organic chemistry, 61(10), 3452-3457.
Chattopadhyay S. et al., Cytotoxicity of in vitro produced podophyllotoxin from podophyllum hexandrum on human cancer cell line, Nat. Prod Res. 2004, 18, 51-57.
Chehimi, J. et al. (1992). Natural killer (NK) cell stimulatory factor increases the cytotoxic activity of NK cells from both healthy donors and human immunodeficiency virus-infected patients. The Journal of experimental medicine, 175(3), 789-796.

(Continued)

*Primary Examiner* — Patrick T Lewis
(74) *Attorney, Agent, or Firm* — Meunier Carlin & Curfman LLC

(57) ABSTRACT

Described are arylnaphthalene lactone derivatives. Also disclosed herein are methods of use of the arylnaphthalene lactone derivatives as anticancer agents.

38 Claims, 14 Drawing Sheets

(56) References Cited

OTHER PUBLICATIONS

Colucci, F., Caligiuri, M. A., & Di Santo, J. P. (2003). What does it take to make a natural killer? Nature Reviews Immunology, 3(5), 413-425.
Critchley-Thorne, R. J. et al. (2009). Impaired interferon signaling is a common immune defect in human cancer. Proceedings of the National Academy of Sciences, 106(22), 9010-9015.
Day SH et al., "Cytotoxic Lignans of Justicia ciliate", J. Nat. Prod. 1999, 62, 1056-1058.
Day SH et al., "Potent Cytotoxic Lignans from Justicia P Rocumbens and Their Effects on Nitric Oxide and Tumor Necrosis Factor-A Production in Mouse Macrophages" J. Nat. Prod 2002, 65, 379-381.
Deng, Y. et al. (2014). The natural product phyllanthusmin C enhances IFN-γ production by human NK cells through upregulation of TLR-mediated NF-κB signaling. The Journal of Immunology, 193(6), 2994-3002.
Di Carlo, E., Comes, A., Orengo, A. M., Rosso, O., Meazza, R., Musiani, P., . . . & Ferrini, S. (2004). IL-21 induces tumor rejection by specific CTL and IFN-γ-dependent CXC chemokines in syngeneic mice. The Journal of Immunology, 172(3), 1540-1547.
Dunn, G. P., Bruce, A. T., Ikeda, H., Old, L. J., & Schreiber, R. D. (2002). Cancer immunoediting: from immunosurveillance to tumor escape. Nature immunology, 3(11), 991-998.
Dunn, G. P., Koebel, C. M., & Schreiber, R. D. (2006). Interferons, immunity and cancer immunoediting. Nature Reviews Immunology, 6(11), 836-848.
Estey, E., & Döhner, H. (2006). Acute myeloid leukaemia. The Lancet, 368(9550), 1894-1907.
Ezoe S., "Secondary Leukemia Associated with the Anti-Cancer Agent, Etoposide, a Topoisomerase II Inhibitor", Int. J. Environ. Res. Public Health 2012, 9, 2444-2453.
Farrugia, L. J. (1999). WinGX suite for small-molecule single-crystal crystallography. Journal of Applied Crystallography, 32(4), 837-838.
Fauriat, C., Long, E. O., Ljunggren, H. G., & Bryceson, Y. T. (2010). Regulation of human NK-cell cytokine and chemokine production by target cell recognition. Blood, 115(11), 2167-2176.
Fehniger, T. A. et al. (1999). Differential cytokine and chemokine gene expression by human NK cells following activation with IL-18 or IL-15 in combination with IL-12: implications for the innate immune response. The Journal of Immunology, 162(8), 4511-4520.
Fehniger, T. A. et al. (2003). CD56bright natural killer cells are present in human lymph nodes and are activated by T cell—derived IL-2: a potential new link between adaptive and innate immunity. Blood, 101(8), 3052-3057.
Fischer, M. H., Yu, N., Gray, G. R., Ralph, J., Anderson, L., & Marlett, J. A. (2004). The gel-forming polysaccharide of psyllium husk (Plantago ovata Forsk). Carbohydrate Research, 339(11), 2009-2017.
Freud, A. G. et al. (2006). Evidence for discrete stages of human natural killer cell differentiation in vivo. The Journal of experimental medicine, 203(4), 1033-1043.
Freud, A. G., & Caligiuri, M. A. (2006). Human natural killer cell development. Immunological reviews, 214(1), 56-72.
Fukamiya N and Lee KH., "Antitumor agents, 81. Justicidin-A and diphyllin, two cytotoxic principles from Justicia procumbens", J. Nat. Prod. 1986, 49, 348-350.
Ge, M. Q. et al. (2012). NK cells regulate CD8+ T cell priming and dendritic cell migration during influenza A infection by IFN-γ and perforin-dependent mechanisms. The Journal of Immunology, 189(5), 2099-2109.
Gertsch, J., Tobler, R. T., Brun, R., Sticher, O., & Heilmann, J. (2003). Antifungal, antiprotozoal, cytotoxic and piscicidal properties of Justicidin B and a new arylnaphthalide lignan from Phyllanthus piscatorum. Planta medica, 69(05), 420-424.
Giri A and Narasu ML., "Production of podophyllotoxin from Podophyllum hexandrum: a potential natural product for clinically useful anticancer drugs", Cytotechnology 2000, 34, 17-26.

Gottlieb, H. E., Kotlyar, V., & Nudelman, A. (1997). NMR chemical shifts of common laboratory solvents as trace impurities. The Journal of organic chemistry, 62(21), 7512-7515.
Gowda, A. et al. (Jan. 2010). Differential effects of IL-2 and IL-21 on expansion of the CD4+ CD25+ Foxp3+ T regulatory cells with redundant roles in natural killer cell mediated antibody dependent cellular cytotoxicity in chronic lymphocytic leukemia. In MAbs (vol. 2, No. 1, pp. 35-41). Taylor & Francis.
Gozler B et al. "Minor lignans from haplophyllum cappadocicum", Phytochemistry 1996, 42, 689-693.
Guillot, B., Portales, P., Thanh, A. D., Merlet, S., Dereure, O., Clot, J., & Corbeau, P. (2005). The expression of cytotoxic mediators is altered in mononuclear cells of patients with melanoma and increased by interferon-α treatment. British Journal of Dermatology, 152(4), 690-696.
Guttridge, D. C., Albanese, C., Reuther, J. Y., Pestell, R. G., & Baldwin, A. S. (1999). NF-κB controls cell growth and differentiation through transcriptional regulation of cyclin D1. Molecular and cellular biology, 19(8), 5785-5799.
Ha, K. H., Byun, M. S., Choi, J., Jeong, J., Lee, K. J., & Jue, D. M. (2009). N-Tosyl-L-phenylalanine chloromethyl ketone inhibits NF-κB activation by blocking specific cysteine residues of IκB kinase β and p65/Re1A. Biochemistry, 48(30), 7271-7278.
Häcker, S. et al.(2009). Histone deacetylase inhibitors cooperate with IFN-γ to restore caspase-8 expression and overcome TRAIL resistance in cancers with silencing of caspase-8. Oncogene, 28(35), 3097-3110.
Harvey, A. L. (2008). Natural products in drug discovery. Drug discovery today, 13(19), 894-901.
Hasinoff, B. B. et al. (2005). Biochemical and proteomics approaches to characterize topoisomerase IIα cysteines and DNA as targets responsible for cisplatin-induced inhibition of topoisomerase IIα. Molecular pharmacology, 67(3), 937-947.
Hayden, M. S., & Ghosh, S. (2004). Signaling to NF-κB. Genes & development, 18(18), 2195-2224.
Hazeldine, J., & Lord, J. M. (2013). The impact of ageing on natural killer cell function and potential consequences for health in older adults. Ageing research reviews, 12(4), 1069-1078.
He, S. et al. (2013). MicroRNAs activate natural killer cells through Toll-like receptor signaling. Blood, 121(23), 4663-4671.
Hopkins, P. A., & Sriskandan, S. (2005). Mammalian Toll-like receptors: to immunity and beyond. Clinical & Experimental Immunology, 140(3), 395-407.
Hornung, V. et al. (2002). Quantitative expression of toll-like receptor 1-10 mRNA in cellular subsets of human peripheral blood mononuclear cells and sensitivity to CpG oligodeoxynucleotides. The Journal of Immunology, 168(9), 4531-4537.
Hwang, J. T., Kwak, D. W., Lin, S. K., Kim, H. M., Kim, Y. M., & Park, O. J. (2007). Resveratrol induces apoptosis in chemoresistant cancer cells via modulation of AMPK signaling pathway. Annals of the New York Academy of Sciences, 1095(1), 441-448.
Ikeda, H., Old, L. J., & Schreiber, R. D. (2002). The roles of IFNγ in protection against tumor development and cancer immunoediting. Cytokine & growth factor reviews, 13(2), 95-109.
Imai, K., Matsuyama, S., Miyake, S., Suga, K., & Nakachi, K. (2000). Natural cytotoxic activity of peripheral-blood lymphocytes and cancer incidence: an 11-year follow-up study of a general population. The Lancet, 356(9244), 1795-1799.
Innocenti G et al., "Patavine, a new arylnaphthalene lignan glycoside from shoot cultures of Haplophyllum patavinum", Chem. Pharm. Bull. 2002, 50, 844-846.
International Preliminary Report on Patentability, Application No. PCT/US2015/023657, dated Oct. 13, 2016, 8 pages.
International Search Report and Written Opinion of the International Searching Authority, Application No. PCT/US2015/023657, dated Jun. 24, 2015, 11 pages.
International Preliminary Report on Patentability, Application No. PCT/US2017/029625, dated Sep. 7, 2018, 7 pages.
Iwasaki, A., & Medzhitov, R. (2004). Toll-like receptor control of the adaptive immune responses. Nature immunology, 5(10), 987-995.
Jahn, T., Zuther, M., Friedrichs, B., Heuser, C., Guhlke, S., Abken, H., & Hombach, A. A. (2012). An IL12-IL2-antibody fusion protein

(56) References Cited

OTHER PUBLICATIONS targeting Hodgkin's lymphoma cells potentiates activation of NK and T cells for an anti-tumor attack. PloS one, 7(9), e44482.
Jewett, A., & Tseng, H. C. (2011). Tumor Induced Inactivation of Natural Killer Cell Cytotoxic Function; Im-plication in Growth, Expansion and Differentiation of Cancer Stem Cells. Journal of Cancer, 2, 443-457.
Jin, M. S. et al. (2007). Crystal structure of the TLR1-TLR2 heterodimer induced by binding of a tri-acylated lipopeptide. Cell, 130(6), 1071-1082.
Joseph, B., Ekedahl, J., Lewensohn, R., Marchetti, P., Formstecher, P., & Zhivotovsky, B. (2001). Defective caspase-3 relocalization in non-small cell lung carcinoma. Oncogene, 20(23), 2877-2888.
Kane, A., & Yang, I. (2010). Interferon-gamma in brain tumor immunotherapy. Neurosurgery clinics of North America, 21(1), 77-86.
Kang K et al., "A novel topoisomerase inhibitor, daurinol, suppresses growth of HCT116 cells with low hematological toxicity compared to etoposide", Neoplasia 2011, 13, 1043-1057.
Kannan, Y., Yu, J., Raices, R. M., Seshadri, S., Wei, M., Caligiuri, M. A., & Wewers, M. D. (2011). IκBζ augments IL-12—and IL-18—mediated IFN-κ production in human NK cells. Blood, 117(10), 2855-2863.
King, A., Jokhi, P. P., Burrows, T. D., Gardner, L., Sharkey, A. M., & Lore, Y. W. (1996). Functions of human decidual NK cells. American Journal of Reproductive Immunology, 35(3), 258-260.
Kinghorn AD et al., "Discovery of anticancer agents of diverse natural origin", Pure Appl. Chem. 2009, 81, 1051-1063.
Kos, F. J., & Engleman, E. G. (1995). Requirement for natural killer cells in the induction of cytotoxic T cells. The Journal of Immunology, 155(2), 578-584.
Kumar CPP et al., "Cytotoxic and genotoxic effects of cleistanthin B in normal and tumour cells", Mutagenesis 1996, 11, 553-557.
Lanier, L. L. (2008). Evolutionary struggles between NK cells and viruses. Nature Reviews Immunology, 8(4), 259-268.
Lee, S. H., Miyagi, T., & Biron, C. A. (2007). Keeping NK cells in highly regulated antiviral warfare. Trends in immunology, 28(6), 252-259.
Lee, S. S. et al. (1996). Six lignans from Phyllanthus myrtifolius. Journal of natural products, 59(11), 1061-1065.
Li, J. W. H., & Vederas, J. C. (2009). Drug discovery and natural products: end of an era or an endless frontier? Science, 325(5937), 161-165.
Li, P., Nijhawan, D., & Wang, X. (2004). Mitochondrial activation of apoptosis. Cell, 116, S57-S61.
Lin MT et al., "Phyllamyricins AC, three novel lignans from Phyllanthus myrtifolius", J. Nat. Prod. 1995, 58, 244-249.
Liu, G., Wu, J., Si, J., Wang, J., & Yang, M. (2008). Complete assignments of 1H and 13C NMR data for three new arylnaphthalene lignan from Justicia procumbens. Magnetic Resonance in Chemistry, 46(3), 283-286.
Lupov, I. P. et al. (2011). Acquired STAT4 deficiency as a consequence of cancer chemotherapy. Blood, 118(23), 6097-6106.
Ma, J. X., Lan, M. S., Qu, S. J., Tan, J. J., Luo, H. F., Tan, C. H., & Zhu, D. Y. (2012). Arylnaphthalene lignan glycosides and other constituents from Phyllanthus reticulatus. Journal of Asian natural products research, 14(11), 1073-1077.
Martín-Fontecha, A., Thomsen, L. L., Brett, S., Gerard, C., Lipp, M., Lanzavecchia, A., & Sallusto, F. (2004). Induced recruitment of NK cells to lymph nodes provides IFN-γ for TH1 priming. Nature immunology, 5(12), 1260-1265.
Masaru Yoshida, et al., "Study of biodegradable copoly (L-lactic acid/glycolic acid) formulations with controlled release of Z-100 for application in radiation therapy", Int. J. Pharm. 115, 61-67, 1995.
Meresse P et al., "Etoposide: Discovery and Medicinal Chemistry", Curr. Med Chem. 2004, 11, 2443-2466.
Mi, Q. (2002). Evaluation of the Potential Cancer Chemotherapeutic Efficacy of Natural Product Isolates Employing in Vivo Hollow Fiber Tests 1. Journal of natural products, 65(6), 842-850.
Mi, Q. et al. (2009). Use of the in Vivo Hollow Fiber Assay in Natural Products Anticancer Drug Discovery. Journal of natural products, 72(3), 573-580.
Mohagheghzadeh, A., Schmidt, T. J., & Alfermann, A. W. (2002). Arylnaphthalene lignans from in vitro cultures of Linum austriacum. Journal of natural products, 65(1), 69-71.
Napetschnig J, Wu H. Molecular basis of NF-kappas signaling. Annu Rev Biophys. 2013;42:443-468.
Nathan, C. F., Murray, H. W., Wiebe, M. E., & Rubin, B. Y. (1983). Identification of interferon-gamma as the lymphokine that activates human macrophage oxidative metabolism and antimicrobial activity. The Journal of experimental medicine, 158(3), 670-689.
Newman DJ and Cragg GM., "Natural products as sources of new drugs over the 30 years from 1981 to 2010", J. Nat. Prod. 2012, 75, 311-335.
Novelli, F., & Casanova, J. L. (2004). The role of IL-12, IL-23 and IFN-γ in immunity to viruses. Cytokine & growth factor reviews, 15(5), 367-377.
Novelo M et al., "Cytotoxic Constituents from Hyptis verticillate", J. Nat. Prod. 1993, 56, 1728-1736.
O'Sullivan, T. et al. (2012). Cancer immunoediting by the innate immune system in the absence of adaptive immunity. The Journal of experimental medicine, 209(10), 1869-1882.
Okigawa, M., Maeda, T., & Kawano, N. (1970). The isolation and structure of three new lignans from Justicia procumbens Linn. var. leucantha Honda. Tetrahedron, 26(18), 4301-4305.
Pan, L., Chai, H. B., & Kinghorn, A. D. (2012). Discovery of new anticancer agents from higher plants. Frontiers in bioscience (Scholar edition), 4, 142-146.
Pan, L., Chai, H., & Kinghorn, A. D. (2010). The continuing search for antitumor agents from higher plants. Phytochemistry letters, 3(1), 1-8.
Pearce (2012). Use of the Hollow Fiber Assay for the Discovery of Novel Anticancer Agents from Fungi. Methods Mol. Biol, 944, 267-277.
Pinho PMM and Kijjoa A., "Chemical constituents of the plants of the genus Cleistanthus and their biological activity", Phytochem. Rev. 2007, 6, 175-182.
Projan, S. J., Carleton, S., & Novick, R. P. (1983). Determination of plasmid copy number By fluorescence densitometry. Plasmid, 9(2), 182-190.
Ralainirina, N., Poli, A., Michel, T., Poos, L., Andrès, E., Hentges, F., & Zimmer, J. (2007). Control of NK cell functions by CD4+ CD25+ regulatory T cells. Journal of leukocyte biology, 81(1), 144-153.
Ramesh C et al., "Arylnaphthalide lignans from Cleistanthus collinus", Chem. Pharm. Bull. 2003, 51, 1299-1300.
Rangkaew, N., Suttisri, R., Moriyasu, M., & Kawanishi, K. (2009). A new arylnaphthalene lignan from Knema furfuracea. Fitoterapia, 80(6), 377-379.
Rao, Y. K., Fang, S. H., & Tzeng, Y. M. (2006). Anti-inflammatory activities of constituents isolated from Phyllanthus polyphyllus. Journal of ethnopharmacology, 103(2), 181-186.
Ren Y et al., "Cytotoxic and NF-κB inhibitory constituents of the stems of Cratoxylum cochinchinense and their semisynthetic analogues", J. Nat. Prod 2011, 74, 1117-1125.
Ren, Y. et al. (2012). Synthesis and antitumor activity of ellagic acid peracetate. ACS medicinal chemistry letters, 3(8), 631-636.
Rezanka T et al., "Glycosides of arylnaphthalene lignans from Acanthus mollis having axial chirality", Phytochemistry 2009, 70, 1049-1054.
Robertson, M. J. et al. (1992). Response of human natural killer (NK) cells to NK cell stimulatory factor (NKSF): cytolytic activity and proliferation of NK cells are differentially regulated by NKSF. The Journal of experimental medicine, 175(3), 779-788.
Robertson, M. J., Chang, H. C., Pelloso, D., & Kaplan, M. H. (2005). Impaired interferon-γ production as a consequence of STAT4 deficiency after autologous hematopoeitic stem cell transplantation for lymphoma. Blood, 106(3), 963-970.
Rosenberg, S. A., Lotze, M. T., Yang, J. C., Aebersold, P. M., Linehan, W. M., Seipp, C. A., & White, D. E. (1989). Experience with the use of high-dose interleukin-2 in the treatment of 652 cancer patients. Annals of surgery, 210(4), 474-485.

(56) References Cited

OTHER PUBLICATIONS

Salem, M. L. et al. (2006). Review: novel nonviral delivery approaches for interleukin-12 protein and gene systems: curbing toxicity and enhancing adjuvant activity. Journal of interferon & cytokine research, 26(9), 593-608.

Sato, Y., Tamura, T., & Mori, M. (2004). Arylnaphthalene Lignans through Pd-Catalyzed [2+ 2+ 2] Cocyclization of Arynes and Diynes: Total Synthesis of Taiwanins C and E. Angewandte Chemie International Edition, 43(18), 2436-2440.

Schoenborn, J. R., & Wilson, C. B. (2007). Regulation of interferon-γ during innate and adaptive immune responses. Advances in immunology, 96, 41-101.

Schonn, I., Hennesen, J., & Dartsch, D. C. (2010). Cellular responses to etoposide: cell death despite cell cycle arrest and repair of DNA damage. Apoptosis, 15(2), 162-172.

Shah, M. H., Freud, A. G., Benson, D. M., Ferkitich, A. K., Dezube, B. J., Bernstein, Z. P., & Caligiuri, M. A. (2006). A phase I study of ultra low dose interleukin-2 and stem cell factor in patients with HIV infection or HIV and cancer. Clinical cancer research, 12(13), 3993-3996.

Shaw, A. C., Joshi, S., Greenwood, H., Panda, A., & Lord, J. M. (2010). Aging of the innate immune system. Current opinion in immunology, 22(4), 507-513.

Sheldrick, G. M. (2008). A short history of SHELX. Acta Crystallographica Section A: Foundations of Crystallography, 64(1), 112-122.

Shi DK et al., "Design, synthesis and biological evaluation of novel glycosylated diphyllin derivatives as topoisomerase II inhibitors", Eur. J. Med. Chem. 2012, 47, 424-431.

Sica, A., Dorman, L., Viggiano, V., Cippitelli, M., Ghosh, P., Rice, N., & Young, H. A. (1997). Interaction of NF-κB and NFAT with the interferon-γ promoter. Journal of Biological Chemistry, 272(48), 30412-30420.

Smyth, M. J., Hayakawa, Y., Takeda, K., & Yagita, H. (2002). New aspects of natural-killer-cell surveillance and therapy of cancer. Nature Reviews Cancer, 2(11), 850-861.

Son, Y. I., Dallal, R. M., Mailliard, R. B., Egawa, S., Jonak, Z. L., & Lotze, M. T. (2001). Interleukin-18 (IL-18) synergizes with IL-2 to enhance cytotoxicity, interferon-γ production, and expansion of natural killer cells. Cancer research, 61(3), 884-888.

Stein, E. M., & Tallman, M. S. (2012). Remission induction in acute myeloid leukemia. International journal of hematology, 96(2), 164-170.

Still, P. C. et al. (2013). Alkaloids from Microcos paniculata with cytotoxic and nicotinic receptor antagonistic activities. Journal of natural products, 76(2), 243-249.

Strengell, M., Matikainen, S., Sirén, J., Lehtonen, A., Foster, D., Julkunen, I., & Sareneva, T. (2003). IL-21 in synergy with IL-15 or IL-18 enhances IFN-γ production in human NK and T cells. The Journal of Immunology, 170(11), 5464-5469.

Susplugas S et al., "Cytotoxic Arylnaphthalene Lignans from a Vietnamese Acanthaceae, Justicia p atentiflora", J. Nat. Prod. 2005, 68, 734-738.

Tajima, F., Kawatani, T., Endo, A., & Kawasaki, H. (1996). Natural killer cell activity and cytokine production as prognostic factors in adult acute leukemia. Leukemia, 10(3), abstract.

Tian J et al., "A new lignan and four new lignan glycosides from Mananthes patentiflora", Helv. Chim. Acta 2006, 89, 291-298.

Tu, S. P., Quante, M., Bhagat, G., Takaishi, S., Cui, G., Yang, X. D., . . . & Wang, T. C. (2011). IFN-γ inhibits gastric carcinogenesis by inducing epithelial cell autophagy and T-cell apoptosis. Cancer research, 71(12), 4247-4259.

Tuchinda P et al., "Cytotoxic Arylnaphthalide Lignan Glycosides from the Aerial Parts of Phyllanthus taxodiifolius", Planta Med. 2006, 72, 60-62.

Tuchinda P et al., "Dichapetalin-type triterpenoids and lignans from the aerial parts of Phyllanthus acutissima", J. Nat. Prod 2008, 71, 655-663.

Vasilev N et al., "Production of Justicidin B, a Cytotoxic Arylnaphthalene Lignan from Genetically Transformed Root Cultures of Linum 1 eonii", J. Nat. Prod. 2006, 69, 1014-1017.

Vivier, E., Tomasello, E., Baratin, M., Walzer, T., & Ugolini, S. (2008). Functions of natural killer cells. Nature immunology, 9(5), 503-510.

Wagner, K., Schulz, P., Scholz, A., Wiedenmann, B., & Menrad, A. (2008). The targeted immunocytokine L19-IL2 efficiently inhibits the growth of orthotopic pancreatic cancer. Clinical Cancer Research, 14(15), 4951-4960.

Wang CY et al., Rapid Screening of Lignans from Phyllanthus myrtifolius and Stilbenoids from Syagrus romanzoffiana by HPLC-SPE-NMR, Phytochem. Anal. 2011, 22, 352-360.

Wang, K. S., Frank, D. A., & Ritz, J. (2000). Interleukin-2 enhances the response of natural killer cells to interleukin-12 through up-regulation of the interleukin-12 receptor and STAT4. Blood, 95(10), 3183-3190.

Watford, W. T., Hissong, B. D., Bream, J. H., Kanno, Y., Muul, L., & O'Shea, J. J. (2004). Signaling by IL-12 and IL-23 and the immunoregulatory roles of STAT4. Immunological reviews, 202(1), 139-156.

Watt, S. V., Andrews, D. M., Takeda, K., Smyth, M. J., & Hayakawa, Y. (2008). IFN-γ-dependent recruitment of mature CD27high NK cells to lymph nodes primed by dendritic cells. The Journal of Immunology, 181(8), 5323-5330.

Woo, M. et al. (1998). Essential contribution of caspase 3/CPP32 to apoptosis and its associated nuclear changes. Genes & development, 12(6), 806-819.

Wu SJ and Wu TS., "Cytotoxic arylnaphthalene lignans from Phyllanthus oligospermus", Chem. Pharm. Bull. 2006, 54, 1223-1225.

Yanada, M., & Naoe, T. (2012). Acute myeloid leukemia in older adults. International journal of hematology, 96(2), 186-193.

Yu, J. (2010). CD94 surface density identifies a functional intermediary between the CD56bright and CD56dim human NK-cell subsets. Blood, 115(2), 274-281.

Yu, J. et al. (2006). Pro-and antiinflammatory cytokine signaling: reciprocal antagonism regulates interferon-gamma production by human natural killer cells. Immunity, 24(5), 575-590.

Zhang, X., & Yu, J. (2010). Target recognition—induced NK-cell responses. Blood, 115(11), 2119-2120.

Zhao Y et al., "Synthesis and Bioevaluation of Diphyllin Glycosides as Novel Anticancer Agents", Arch. Pharm. Chem. Life Sci. 2012, 345, 622-628.

Zhao, Y., Hui, J., Wang, D., Zhu, L., Fang, J. H., & Zhao, X. D. (2010). Synthesis, cytotoxicity and pro-apoptosis of novel benzoisoindolin hydrazones as anticancer agents. Chemical and Pharmaceutical Bulletin, 58(10), 1324-1327.

Zhao, Yu, Ya-Peng, L., & Li, Z. (2008). Synthesis of Per-acetyl d-fucopyranosyl Bromide and Its Use in Preparation of Diphyllin d-fucopyranosyl Glycoside. Journal of Carbohydrate Chemistry, 27(2), 113-119.

Pubchem: Substance Record for SID 202033529. Sep. 8, 2014. [Retrieved on Jun. 21, 2017, https://pubchem.ncbi.nlm.nih.gov/substance/202033529#section=Top.

International Search Report and Written Opinion issued by the U.S. Patent and Trademark Office Search Authority for PCT Application No. PCT/US2017/029625. dated Jul. 13, 2017. 9 pages.

ANTITUMOR ARYLNAPHTHALENE LIGAND GLYCOSIDES

CROSS-REFERENCE TO RELATED APPLICATIONS

This application claims the benefit of and priority to U.S. Patent Application No. 62/300,306 filed on Feb. 26, 2016, the disclosure of which is expressly incorporated herein by reference in its entirety.

STATEMENT OF GOVERNMENT SUPPORT

This invention was made with government support under Grant No. CA125066, Grant No. CA090787, Grant No. CA155521, Grant No. OD018403, Grant No. CA163205, and Grant No. CA068458, all awarded by the National Institutes of Health. The government has certain rights in the invention.

BACKGROUND

Natural products and their semi-synthetic derivatives are used widely in cancer chemotherapy (Newman D J and Cragg G M. *J. Nat. Prod.* 2012, 75, 311-335; Kinghorn A D et al. *Pure Appl. Chem.* 2009, 81, 1051-1063). As an example, etoposide (VP-16) is a semi-synthetic aryltetralin lignan glycoside modeled on the natural product podophyllotoxin. It targets DNA topoisomerase II (topo II) and has been utilized for decades to treat several types of cancer (Meresse P et al. *Curr. Med Chem.* 2004, 11, 2443-2466). However, side effects have been reported for etoposide, including myelosuppression and the development of secondary leukemias linked to topo II inhibitory activity (Ezoe S. *Int. J. Environ. Res. Public Health* 2012, 9, 2444-2453).

Podophyllotoxin is an aryltetralin lignan that occurs in *Podophyllum peltatum* and *P. emodi* var. *hexandrum* (syn. *Sinopodophyllum hexandrum*) (Berberidaceae) (Meresse P et al. *Curr. Med Chem.* 2004, 11, 2443-2466; Chattopadhyay S et al. *Nat. Prod Res.* 2004, 18, 51-57; Girl A and Narasu M L. *Cytotechnology* 2000, 34, 17-26). In addition to *Podophyllum* species (Atta-ur-Rahman et al. *Phytochemistry* 1995, 40, 427-431), a number of arylnaphthalene lignan lactones, structurally similar to podophyllotoxin, have been identified as minor constituents from plants in the genera *Cleistanthus* (Euphorbiaceae) (Pinho P M M and Kijjoa A *Phytochem. Rev.* 2007, 6, 175-182), *Haplophyllum* (Rutaceae) (Oozier B et al. *Phytochemistry* 1996, 42, 689-693; Al-Abed Y et al. *Phytochemistry* 1998, 49, 1779-1781), *Justicia* (Acanthaceae) (Susplugas S et al. *J. Nat. Prod.* 2005, 68, 734-738), *Mananthes* (Acanthaceae) (Tian J et al. *Helv. Chim. Acta* 2006, 89, 291-298), and *Phyllanthus* (Phyllanthaceae) (Lin M T et al. *J. Nat. Prod.* 1995, 58, 244-249; Tuchinda P et al. *Planta Med.* 2006, 72, 60-62; Wu S J and Wu T S. *Chem. Pharm. Bull.* 2006, 54, 1223-1225; Tuchinda P et al. *J. Nat. Prod* 2008, 71, 655-663; Wang C Y et al. *Phytochem. Anal.* 2011, 22, 352-360). Many naturally occurring arylnaphthalene lignan lactones have been reported to possess cytotoxicity toward panels of human cancer cell lines (Susplugas S et al. *J. Nat. Prod.* 2005, 68, 734-738; Lin M T et al. *J. Nat. Prod.* 1995, 58, 244-249; Tuchinda P et al. *Planta Med.* 2006, 72, 60-62; Wu S J and Wu T S. *Chem. Pharm. Bull.* 2006, 54, 1223-1225; Tuchinda P et al. *J. Nat. Prod* 2008, 71, 655-663; *Phytochem. Anal.* 2011, 22, 352-360; Fukamiya N and Lee K H. *J. Nat. Prod.* 1986, 49, 348-350; Novelo M et al. *J. Nat. Prod.* 1993, 56, 1728-1736; Day S H et al. *J. Nat. Prod.* 1999, 62, 1056-1058; Innocenti G et al. *Chem. Pharm. Bull.* 2002, 50, 844-846; Day S H et al. *J. Nat. Prod* 2002, 65, 379-381; Ramesh C et al. *Chem. Pharm. Bull.* 2003, 51, 1299-1300; Vasilev N et al. *J. Nat. Prod.* 2006, 69, 1014-1017), and several of their synthetic analogues also showed such activity (Zhao Y et al. *Arch. Pharm. Chem. Life Sci.* 2012, 345, 622-628; Shi D K et al. *Eur. J. Med. Chem.* 2012, 47, 424-431). Some arylnaphthalene lignan lactones have exhibited in vivo antitumor efficacy (Rezanka T et al. *Phytochemistry* 2009, 70, 1049-1054; Kang K et al. *Neoplasia* 2011, 13, 1043-1057), and a compound, cleistanthin B, showed selective cytotoxicity toward human tumor cells (Kumar C P P et al. *Mutagenesis* 1996, 11, 553-557). Some of these compounds showed a mechanism of action different from etoposide (Susplugas S et al. *J. Nat. Prod.* 2005, 68, 734-738; Kang K et al. *Neoplasia* 2011, 13, 1043-1057), and several analogues did not act as topo II poisons mechanistically (Zhao Y et al. *Arch. Pharm. Chem. Life Sci.* 2012, 345, 622-628; Shi D K et al. *Eur. J. Med. Chem.* 2012, 47, 424-431). What are needed are new compositions for the treatment of cancer, e.g., arylnaphthalene lactone derivatives. The compounds, compositions and methods disclosed herein address these and other needs.

SUMMARY

In accordance with the purposes of the disclosed materials, compounds, compositions, kits and methods, as embodied and broadly described herein, the disclosed subject matter relates to compounds, compositions, methods of making said compounds and/or compositions, and methods of using said compounds and/or compositions. More specifically, arylnaphthalene lactone derivatives are provided herein. Also disclosed herein are methods of use of the disclosed arylnaphthalene lactone derivatives as anticancer and immunostimulant agents.

Additional advantages will be set forth in part in the description that follows or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE FIGURE

The accompanying figure, which is incorporated in and constitutes a part of this specification, illustrates several aspects described below.

DETAILED DESCRIPTION

Figure 1:
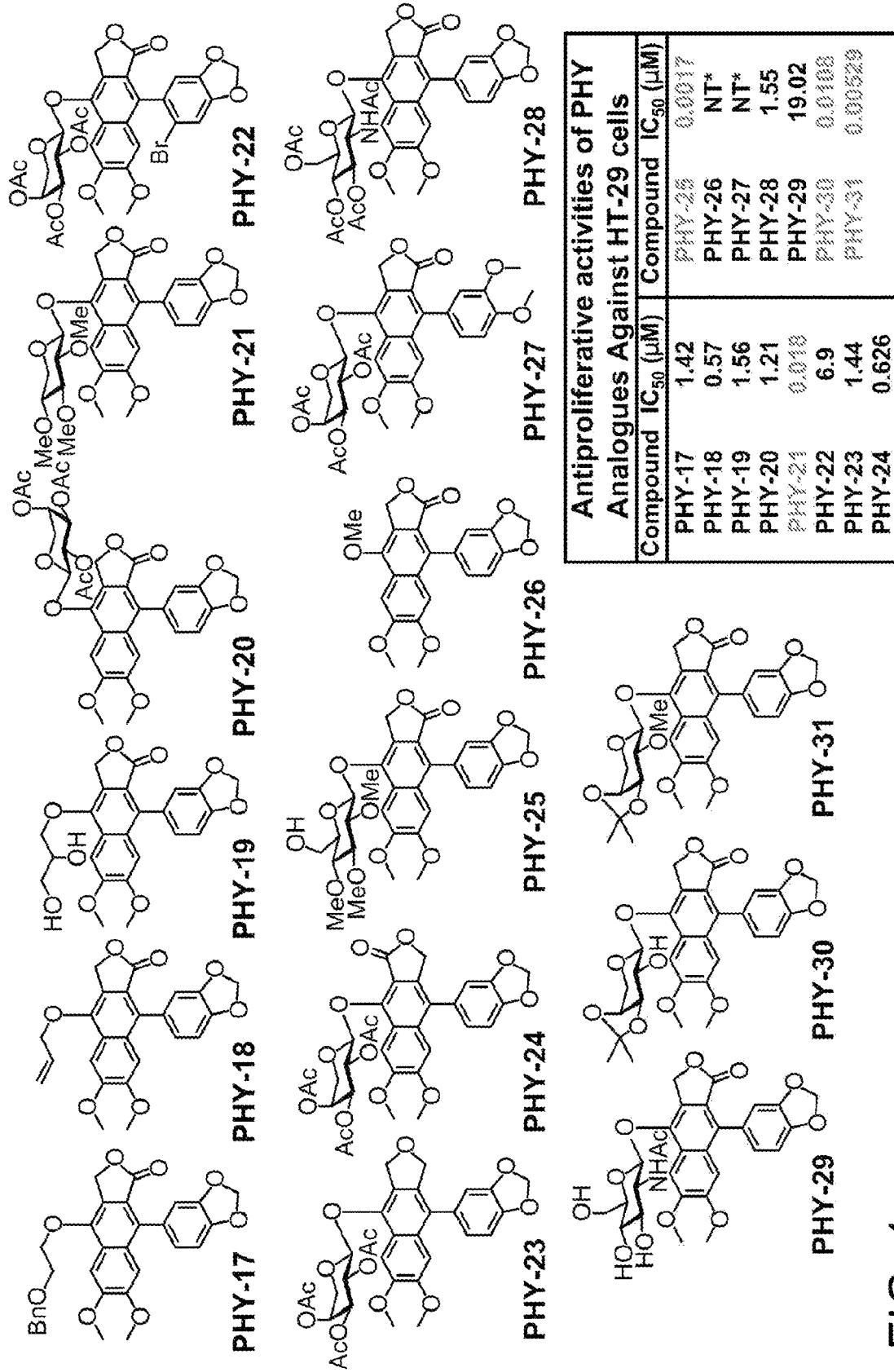
FIG. 1 displays the structures of several arylnaphthalene ligands.

The materials, compounds, compositions, articles, and methods described herein may be understood more readily by reference to the following detailed description of specific aspects of the disclosed subject matter and the Examples included therein.

Before the present materials, compounds, compositions, kits, and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

General Definitions

In this specification and in the claims that follow, reference will be made to a number of terms, which shall be defined to have the following meanings:

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "the compound" includes mixtures of two or more such compounds, reference to "an agent" includes mixture of two or more such agents, and the like.

"Optional" or "optionally" means that the subsequently described event or circumstance can or cannot occur, and that the description includes instances where the event or circumstance occurs and instances where it does not.

As used herein, by a "subject" is meant an individual. Thus, the "subject" can include domesticated animals (e.g., cats, dogs, etc.), livestock (e.g., cattle, horses, pigs, sheep, goats, etc.), laboratory animals (e.g., mouse, rabbit, rat, guinea pig, etc.), and birds. "Subject" can also include a mammal, such as a primate or a human.

By "reduce" or other forms of the word, such as "reducing" or "reduction," is meant lowering of an event or characteristic (e.g., tumor growth). It is understood that this is typically in relation to some standard or expected value, in other words it is relative, but that it is not always necessary for the standard or relative value to be referred to. For example, "reduces tumor growth" means reducing the rate of growth of a tumor relative to a standard or a control.

By "prevent" or other forms of the word, such as "preventing" or "prevention," is meant to stop a particular event or characteristic, to stabilize or delay the development or progression of a particular event or characteristic, or to minimize the chances that a particular event or characteristic will occur. Prevent does not require comparison to a control as it is typically more absolute than, for example, reduce. As used herein, something could be reduced but not prevented, but something that is reduced could also be prevented. Likewise, something could be prevented but not reduced, but something that is prevented could also be reduced. It is understood that where reduce or prevent are used, unless specifically indicated otherwise, the use of the other word is also expressly disclosed.

By "treat" or other forms of the word, such as "treated" or "treatment," is meant to administer a composition or to perform a method in order to reduce, inhibit, or eliminate a particular characteristic or event (e.g., tumor growth or survival). The term "control" is used synonymously with the term "treat."

The term "anticancer" refers to the ability to treat or control cellular proliferation and/or tumor growth at any concentration.

The term "therapeutically effective" means the amount of the composition used is of sufficient quantity to ameliorate one or more causes or symptoms of a disease or disorder. Such amelioration only requires a reduction or alteration, not necessarily elimination.

The term "pharmaceutically acceptable" refers to those compounds, materials, compositions, and/or dosage forms which are, within the scope of sound medical judgment, suitable for use in contact with the tissues of human beings and animals without excessive toxicity, irritation, allergic response, or other problems or complications commensurate with a reasonable benefit/risk ratio.

Chemical Definitions

As used herein, the term "substituted" is contemplated to include all permissible substituents of organic compounds. In a broad aspect, the permissible substituents include acyclic and cyclic, branched and unbranched, carbocyclic and heterocyclic, and aromatic and nonaromatic substituents of organic compounds. Illustrative substituents include, for example, those described below. The permissible substituents can be one or more and the same or different for appropriate organic compounds. For purposes of this disclosure, the heteroatoms, such as nitrogen, can have hydrogen substituents and/or any permissible substituents of organic compounds described herein which satisfy the valences of the heteroatoms. This disclosure is not intended to be limited in any manner by the permissible substituents of organic compounds. Also, the terms "substitution" or "substituted with" include the implicit proviso that such substitution is in accordance with permitted valence of the substituted atom and the substituent, and that the substitution results in a stable compound, e.g., a compound that does not spontaneously undergo transformation such as by rearrangement, cyclization, elimination, etc.

"$Z^1$," "$Z^2$," "$Z^3$," and "$Z^4$" are used herein as generic symbols to represent various specific substituents. These symbols can be any substituent, not limited to those disclosed herein, and when they are defined to be certain substituents in one instance, they can, in another instance, be defined as some other substituents.

As used herein, the term "acyl" refers to a group of formula —C(O)$Z^1$, where $Z^1$ is hydrogen, alkyl (e.g., $C_1$-$C_{10}$ alkyl), haloalkyl ($C_1$-$C_8$ haloalkyl), alkenyl ($C_2$-$C_8$ alkenyl), haloalkenyl (e.g., $C_2$-$C_8$ haloalkenyl), alkynyl (e.g., $C_2$-$C_8$ alkynyl), alkoxy ($C_1$-$C_8$ alkoxy), haloalkoxyl ($C_1$-$C_8$ alkoxy), aryl, or heteroaryl, arylalkyl ($C_7$-$C_{10}$ arylalkyl), as defined below, where "C(O)" or "CO" is shorthand notation for C=O. A C(O) group is also referred to herein as a carbonyl. In some embodiments, the acyl group can be a $C_1$-$C_6$ acyl group (e.g., a formyl group, a $C_1$-$C_5$ alkylcarbonyl group, or a $C_1$-$C_5$ haloalkylcarbonyl group). In some embodiments, the acyl group can be a $C_1$-$C_3$ acyl group (e.g., a formyl group, a $C_1$-$C_3$ alkylcarbonyl group, or a $C_1$-$C_3$ haloalkylcarbonyl group).

As used herein, the term "alkyl" refers to straight-chained, branched, or cyclic, saturated hydrocarbon moieties. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples of alkyl groups include methyl, ethyl, propyl, isopropyl, 1-methyl-ethyl, butyl, isobutyl, t-butyl, 1-methyl-propyl, 2-methyl-propyl, 1,1-dimethyl-ethyl, pentyl, 1-methyl-butyl, 2-methyl-butyl, 3-methyl-butyl, 2,2-dimethyl-propyl, 1-ethyl-propyl, hexyl, 1,1-dimethyl-propyl, 1,2-dimethyl-propyl, 1-methyl-pentyl, 2-methyl-pentyl, 3-methyl-pentyl, 4-methyl-pentyl, 1,1-dimethyl-butyl, 1,2-dimethyl-butyl, 1,3-dimethyl-butyl, 2,2-dimethyl-butyl, 2,3-dimethyl-butyl, 3,3-dimethyl-butyl, 1-ethyl-butyl, 2-ethyl-butyl, 1,1,2-trimethyl-propyl, 1,2,2-trimethyl-propyl, 1-ethyl-1-methyl-propyl, 1-ethyl-2-methyl-propyl, pentyl, hexyl, heptyl, octyl, nonyl, decyl, dodecyl, tetradecyl, hexadecyl, eicosyl, tetracosyl, and the like. Alkyl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, and haloalkylaminocarbonyl, provided that the substituents are sterically compatible and the rules of chemical bonding and strain energy are satisfied.

Throughout the specification "alkyl" is generally used to refer to both unsubstituted alkyl groups and substituted alkyl groups; however, substituted alkyl groups are also specifically referred to herein by identifying the specific substituent(s) on the alkyl group. For example, the term "halogenated alkyl" specifically refers to an alkyl group that is substituted with one or more halide, e.g., fluorine, chlorine, bromine, or iodine. The term "alkoxyalkyl" specifically refers to an alkyl group that is substituted with one or more alkoxy groups, as described below. The term "alkylamino" specifically refers to an alkyl group that is substituted with one or more amino groups, as described below, and the like. When "alkyl" is used in one instance and a specific term such as "alkylalcohol" is used in another, it is not meant to imply that the term "alkyl" does not also refer to specific terms such as "alkylalcohol" and the like.

This practice is also used for other groups described herein. That is, while a term such as "cycloalkyl" refers to both unsubstituted and substituted cycloalkyl moieties, the substituted moieties can, in addition, be specifically identified herein; for example, a particular substituted cycloalkyl can be referred to as, e.g., an "alkylcycloalkyl." Similarly, a substituted alkoxy can be specifically referred to as, e.g., a "halogenated alkoxy," a particular substituted alkenyl can be, e.g., an "alkenylalcohol," and the like. Again, the practice of using a general term, such as "cycloalkyl," and a specific term, such as "alkylcycloalkyl," is not meant to imply that the general term does not also include the specific term.

As used herein, the term "haloalkyl" refers to straight-chained or branched alkyl groups, wherein these groups the hydrogen atoms may partially or entirely be substituted with halogen atoms. Unless otherwise specified, $C_1$-$C_{20}$ (e.g., $C_1$-$C_{12}$, $C_1$-$C_{10}$, $C_1$-$C_8$, $C_1$-$C_6$, $C_1$-$C_4$) alkyl groups are intended. Examples include chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2-difluoroethyl, 2,2-dichloro-2-fluoroethyl, 2,2,2-trichloroethyl, pentafluoroethyl, and 1,1,1-trifluoroprop-2-yl. Haloalkyl substituents may be unsubstituted or substituted with one or more chemical moieties. Examples of suitable substituents include, for example, hydroxy, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl$C_1$-$C_6$ haloalkylcarbonyl, and haloalkylaminocarbonyl, provided that the substituents are sterically compatible and the rules of chemical bonding and strain energy are satisfied.

The term "cycloalkyl" as used herein is a non-aromatic carbon-based ring. Unless otherwise specified $C_3$-$C_{20}$ (e.g., $C_3$-$C_{12}$, $C_3$-$C_{10}$, $C_3$-$C_8$, $C_3$-$C_6$) cycloalkyl groups are intended.

Examples of cycloalkyl groups include, but are not limited to, cyclopropyl, cyclobutyl, cyclopentyl, cyclohexyl, etc. The term "heterocycloalkyl" is a cycloalkyl group as defined above, and is included within the meaning of the term "cycloalkyl," containing one or more heteroatoms, viz., N, O or S. The cycloalkyl or heterocycloalkyl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, $C_1$-$C_6$ haloalkylcarbonyl, and haloalkylaminocarbonyl, provided that the substituents are sterically compatible and the rules of chemical bonding and strain energy are satisfied.

As used herein, the term "alkenyl" refers to straight-chained, branched, or cyclic, unsaturated hydrocarbon moieties containing a double bond. Asymmetric structures such as $(Z^1Z^2)C=C(Z^3Z^4)$ are intended to include both the E and Z isomers. This can be presumed in structural formulae herein wherein an asymmetric alkene is present, or it can be explicitly indicated by the bond symbol C=C. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkenyl groups are intended. Alkenyl groups may contain more than one unsaturated bond. Examples include ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl, and 1-ethyl-2-methyl-2-propenyl. The term "vinyl" refers to a group having the structure —CH=CH$_2$; 1-propenyl refers to a group with the structure —CH=CH—CH$_3$; and 2-propenyl refers to a group with the structure —CH$_2$—CH=CH$_2$. Alkenyl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, $C_1$-$C_6$ haloalkylcarbonyl, and haloalkylaminocarbonyl, provided that the substituents are sterically compatible and the rules of chemical bonding and strain energy are satisfied.

The term "haloalkenyl," as used herein, refers to an alkenyl group, as defined above, which is substituted by one or more halogen atoms.

The term "cycloalkenyl" as used herein is a non-aromatic carbon-based ring containing at least one double bond. Unless otherwise specified $C_3$-$C_{20}$ (e.g., $C_3$-$C_{12}$, $C_3$-$C_{10}$, $C_3$-$C_8$, $C_3$-$C_6$) cycloalkenyl groups are intended. Examples of cycloalkenyl groups include, but are not limited to, cyclopropenyl, cyclobutenyl, cyclopentenyl, cyclopentadienyl, cyclohexenyl, cyclohexadienyl, and the like. The term "heterocycloalkenyl" is a type of cycloalkenyl group as defined above, and is included within the meaning of the term "cycloalkenyl," containing one or more heteroatoms, viz., N, O or S. The cycloalkenyl or heterocycloalkenyl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, $C_1$-$C_6$ haloalkylcarbonyl, and haloalkylaminocarbonyl, provided that the substituents are sterically compatible and the rules of chemical bonding and strain energy are satisfied.

As used herein, the term "alkynyl" represents straight-chained or branched hydrocarbon moieties containing a triple bond. Unless otherwise specified, $C_2$-$C_{20}$ (e.g., $C_2$-$C_{12}$, $C_2$-$C_{10}$, $C_2$-$C_8$, $C_2$-$C_6$, $C_2$-$C_4$) alkynyl groups are intended. Alkynyl groups may contain more than one unsaturated bond. Examples include $C_2$-$C_6$-alkynyl, such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl, and 1-ethyl-1-methyl-2-propynyl. Alkynyl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, $C_1$-$C_6$ haloalkylcarbonyl, and haloalkylaminocarbonyl, provided that the substituents are sterically compatible and the rules of chemical bonding and strain energy are satisfied.

As used herein, the term "alkoxy" refers to a group of the formula —$OZ^1$, where $Z^1$ is unsubstituted or substituted alkyl as defined above. In other words, as used herein an "alkoxy" group is an unsubstituted or substituted alkyl group bound through a single, terminal ether linkage. Unless otherwise specified, alkoxy groups wherein $Z^1$ is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include methoxy, ethoxy, propoxy, 1-methyl-ethoxy, butoxy, 1-methyl-propoxy, 2-methyl-propoxy, 1,1-dimethyl-ethoxy, pentoxy, 1-methyl-butyloxy, 2-methyl-butoxy, 3-methyl-butoxy, 2,2-di-methyl-propoxy, 1-ethyl-propoxy, hexoxy, 1,1-dimethyl-propoxy, 1,2-dimethyl-propoxy, 1-methyl-pentoxy, 2-methyl-pentoxy, 3-methyl-pentoxy, 4-methyl-pentoxy, 1,1-dimethyl-butoxy, 1,2-dimethyl-butoxy, 1,3-dimethyl-butoxy, 2,2-dimethyl-butoxy, 2,3-dimethyl-butoxy, 3,3-dimethyl-butoxy, 1-ethyl-butoxy, 2-ethylbutoxy, 1,1,2-trimethyl-propoxy, 1,2,2-trimethyl-propoxy, 1-ethyl-1-methyl-propoxy, and 1-ethyl-2-methyl-propoxy.

As used herein, the term "haloalkoxy" refers to a group of the formula —$OZ^1$, where $Z^1$ is unsubstituted or substituted haloalkyl as defined above. Unless otherwise specified, haloalkoxy groups wherein $Z^1$ is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group are intended. Examples include chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro, 2-difluoroethoxy, 2,2-dichloro-2-fluoroethoxy, 2,2,2-trichloroethoxy, pentafluoroethoxy, and 1,1,1-trifluoroprop-2-oxy.

As used herein, the term "aryl," as well as derivative terms such as aryloxy, refers to groups that include a monovalent aromatic carbocyclic group of from 6 to 14 carbon atoms. Aryl groups can include a single ring or multiple condensed rings. In some embodiments, aryl groups include $C_6$-$C_{10}$ aryl groups. Examples of aryl groups include, but are not limited to, phenyl, biphenyl, naphthyl, tetrahydronaphtyl, phenylcyclopropyl, and indanyl. In some embodiments, the aryl group can be a phenyl, indanyl or naphthyl group. The term "heteroaryl", as well as derivative terms such as "heteroaryloxy", refers to a 5- or 6-membered aromatic ring containing one or more heteroatoms, viz., N, O or S; these heteroaromatic rings may be fused to other aromatic systems. The aryl or heteroaryl substituents may be unsubstituted or substituted with one or more chemical moieties. Examples of suitable substituents include, for example, hydroxy, halogen, nitro, cyano, formyl, $C_1$-$C_8$ alkyl, $C_1$-$C_8$ haloalkyl, $C_3$-$C_{12}$ cycloalkyl, $C_3$-$C_{12}$ heterocycloalkyl, $C_2$-$C_8$ alkenyl, $C_2$-$C_8$ haloalkenyl, $C_3$-$C_{12}$ cycloalkenyl, $C_3$-$C_{12}$ heterocycloalkenyl, $C_2$-$C_8$ alkynyl, $C_1$-$C_8$ alkoxy, $C_1$-$C_8$ haloalkoxy, $C_1$-$C_8$ alkoxycarbonyl, hydroxycarbonyl, $C_1$-$C_8$ acyl, $C_1$-$C_8$ alkylcarbonyl, $C_6$-$C_{10}$ aryl, $C_6$-$C_{10}$ heteroaryl, amino, amido, $C_1$-$C_8$ carbamoyl, $C_1$-$C_8$ halocarbamoyl, phosphonyl, silyl, sulfinyl, $C_1$-$C_6$ alkylsulfinyl, $C_1$-$C_6$ haloalkylsulfinyl, sulfonyl, $C_1$-$C_6$ alkylsulfonyl, $C_1$-$C_6$ haloalkylsulfonyl, sulfonamide, thio, $C_1$-$C_6$ alkylthio, $C_1$-$C_6$ haloalkylthio, $C_1$-$C_6$ alkylaminocarbonyl, $C_1$-$C_6$ dialkylaminocarbonyl, $C_1$-$C_6$ haloalkoxycarbonyl, $C_1$-$C_6$ haloalkylcarbonyl, and haloalkylaminocarbonyl, provided that the substituents are sterically compatible and the rules of chemical bonding and strain energy are satisfied.

The term "biaryl" is a specific type of aryl group and is included in the definition of aryl. Biaryl refers to two aryl groups that are bound together via a fused ring structure, as in naphthalene, or are attached via one or more carbon-carbon bonds, as in biphenyl.

As used herein, the term "arylalkyl" refers to an alkyl group substituted with an unsubstituted or substituted aryl group. $C_7$-$C_{10}$ arylalkyl refers to a group wherein the total number of carbon atoms in the group is 7 to 10, not including the carbon atoms present in any substituents of the aryl group.

The term "cyclic group" is used herein to refer to either aryl groups, non-aryl groups (i.e., cycloalkyl, heterocycloalkyl, cycloalkenyl, and heterocycloalkenyl groups), or both. Cyclic groups have one or more ring systems that can be substituted or unsubstituted. A cyclic group can contain one or more aryl groups, one or more non-aryl groups, or one or more aryl groups and one or more non-aryl groups.

As used herein, the term "alkylcarbonyl" refers to an unsubstituted or substituted alkyl group bonded to a carbonyl group, wherein a carbonyl group is C(O). $C_1$-$C_3$ alkylcarbonyl and $C_1$-$C_3$ haloalkylcarbonyl refer to groups wherein a $C_1$-$C_3$ unsubstituted or substituted alkyl or haloalkyl group is bonded to a carbonyl group (the group contains a total of 2 to 4 carbon atoms).

As used herein, the term "alkoxycarbonyl" refers to a group of the formula

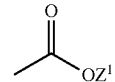

wherein can be a hydrogen, $C_1$-$C_8$ alkyl, $C_1$-$C_8$ haloalkyl, $C_2$-$C_8$ alkenyl, $C_2$-$C_8$ alkynyl, $C_6$-$C_{10}$ aryl, $C_6$-$C_{10}$ heteroaryl, $C_3$-$C_{12}$ cycloalkyl, $C_3$-$C_{12}$ cycloalkenyl, $C_3$-$C_{12}$ heterocycloalkyl, or $C_3$-$C_{12}$ heterocycloalkenyl group as described above.

The term "carboxylic acid" as used herein is represented by the formula —C(O)OH. A "carboxylate" or "carboxyl" group as used herein is represented by the formula —C(O)O$^-$.

As used herein, the terms "amine" or "amino" refers to a group of the formula —$NZ^1Z^2$, where $Z^1$ and $Z^2$ can independently be a hydrogen, alkyl, haloalkyl, alkenyl, alkynyl, aryl, heteroaryl, cycloalkyl, cycloalkenyl, heterocycloalkyl, or heterocycloalkenyl group as described above. As used herein, the term "alkylamino" refers to an amino group substituted with one or two unsubstituted or substituted alkyl groups, which may be the same or different. As used herein, the term "haloalkylamino" refers to an alkylamino group wherein the alkyl carbon atoms are partially or entirely substituted with halogen atoms.

As used herein, "amido" refers to a group of the formula —C(O)$NZ^1Z^2$, where $Z^1$ and $Z^2$ can independently be a hydrogen, $C_1$-$C_8$ alkyl, $C_1$-$C_8$ haloalkyl, $C_2$-$C_8$ alkenyl, $C_2$-$C_8$ alkynyl, $C_6$-$C_{10}$ aryl, $C_6$-$C_{10}$ heteroaryl, $C_3$-$C_{12}$ cycloalkyl, $C_3$-$C_{12}$ cycloalkenyl, $C_3$-$C_{12}$ heterocycloalkyl, or $C_3$-$C_{12}$ heterocycloalkenyl group as described above. As used herein, $C_1$-$C_6$ alkylaminocarbonyl refers to a group of the formula —C(O)$NHZ^1$ wherein $Z^1$ is $C_1$-$C_6$ unsubstituted or substituted alkyl. As used herein, $C_1$-$C_6$ dialkylaminocarbonyl refers to a group of the formula —C(O)N(Z$^1$)$_2$ wherein each Z$^1$ is independently C$_1$-C$_6$ unsubstituted or substituted alkyl.

As used herein, the term "carbamyl" (also referred to as carbamoyl and aminocarbonyl) refers to a group of the formula

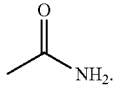

As used herein, the term "phosphonyl" refers to a group of the formula

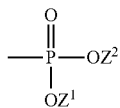

where Z$^1$ and Z$^2$ can independently be a hydrogen, C$_1$-C$_8$ alkyl, C$_1$-C$_8$ haloalkyl, C$_2$-C$_8$ alkenyl, C$_2$-C$_8$ alkynyl, C$_6$-C$_{10}$ aryl, C$_6$-C$_{10}$ heteroaryl, C$_3$-C$_{12}$ cycloalkyl, C$_3$-C$_{12}$ cycloalkenyl, C$_3$-C$_{12}$ heterocycloalkyl, or C$_3$-C$_{12}$ heterocycloalkenyl group as described above. As used herein "alkylphosphonyl" refers to a phosphonyl group substituted with one or two unsubstituted or substituted alkyl groups, which may be the same or different. As used herein, the term "haloalkylphosphonyl" refers to an alkylphosphonyl group wherein the alkyl carbon atoms are partially or entirely substituted with halogen atoms.

The term "silyl" as used herein is represented by the formula —SiZ$^1$Z$^2$Z$^3$, where Z$^1$, Z$^2$, and Z$^3$ can be, independently, a hydrogen, C$_1$-C$_8$ alkyl, C$_1$-C$_8$ haloalkyl, C$_2$-C$_8$ alkenyl, C$_2$-C$_8$ alkynyl, C$_6$-C$_{10}$ aryl, C$_6$-C$_{10}$ heteroaryl, C$_3$-C$_{12}$ cycloalkyl, C$_3$-C$_{12}$ cycloalkenyl, C$_3$-C$_{12}$ heterocycloalkyl, or C$_3$-C$_{12}$ heterocycloalkenyl group as described above. As used herein, C$_1$-C$_6$ trialkylsilyl refers to a group of the formula —Si(Z$^1$)$_3$ wherein each Z$^1$ is independently a C$_1$-C$_6$ unsubstituted or substituted alkyl group (the group contains a total of 3 to 18 carbon atoms).

As used herein, the term "sulfinyl" refers to a group of the formula

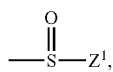

where Z$^1$ can be a hydrogen, C$_1$-C$_8$ alkyl, C$_1$-C$_8$ haloalkyl, C$_2$-C$_8$ alkenyl, C$_2$-C$_8$ alkynyl, C$_6$-C$_{10}$ aryl, C$_6$-C$_{10}$ heteroaryl, C$_3$-C$_{12}$ cycloalkyl, C$_3$-C$_{12}$ cycloalkenyl, C$_3$-C$_{12}$ heterocycloalkyl, or C$_3$-C$_{12}$ heterocycloalkenyl group as described above. The term "alkylsulfinyl" refers to a sulfinyl group substituted with an unsubstituted or substituted alkyl group. As used herein, the term "haloalkylsulfinyl" refers to an alkylsulfinyl group wherein the alkyl carbon atoms are partially or entirely substituted with halogen atoms.

As used herein, the term "sulfonyl" refers to a group of the formula

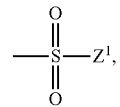

where Z$^1$ can be a hydrogen, C$_1$-C$_8$ alkyl, C$_1$-C$_8$ haloalkyl, C$_2$-C$_8$ alkenyl, C$_2$-C$_8$ alkynyl, C$_6$-C$_{10}$ aryl, C$_6$-C$_{10}$ heteroaryl, C$_3$-C$_{12}$ cycloalkyl, C$_3$-C$_{12}$ cycloalkenyl, C$_3$-C$_{12}$ heterocycloalkyl, or C$_3$-C$_{12}$ heterocycloalkenyl group as described above. The term "alkylsulfonyl" refers to a sulfonyl group substituted with an unsubstituted or substituted alkyl group. As used herein, the term "haloalkylsulfonyl" refers to an alkylsulfonyl group wherein the alkyl carbon atoms are partially or entirely substituted with halogen atoms.

The term "sulfonylamino" or "sulfonamide" as used herein is represented by the formula —S(O)$_2$NHZ$^1$, where Z$^1$ can be a hydrogen, C$_1$-C$_8$ alkyl, C$_1$-C$_8$ haloalkyl, C$_2$-C$_8$ alkenyl, C$_2$-C$_8$ alkynyl, C$_6$-C$_{10}$ aryl, C$_6$-C$_{10}$ heteroaryl, C$_3$-C$_{12}$ cycloalkyl, C$_3$-C$_{12}$ cycloalkenyl, C$_3$-C$_{12}$ heterocycloalkyl, or C$_3$-C$_{12}$ heterocycloalkenyl group as described above.

As used herein, the term "thio" refers to a group of the formula —SZ$^1$, where Z$^1$ can be a hydrogen, C$_1$-C$_8$ alkyl, C$_1$-C$_8$ haloalkyl, C$_2$-C$_8$ alkenyl, C$_2$-C$_8$ alkynyl, C$_6$-C$_{10}$ aryl, C$_6$-C$_{10}$ heteroaryl, C$_3$-C$_{12}$ cycloalkyl, C$_3$-C$_{12}$ cycloalkenyl, C$_3$-C$_{12}$ heterocycloalkyl, or C$_3$-C$_{12}$ heterocycloalkenyl group as described above.

The term "thiol" as used herein is represented by the formula —SH.

As used herein, the term "alkylthio" refers to a thio group substituted with an unsubstituted or substituted alkyl as defined above. Unless otherwise specified, alkylthio groups wherein the alkyl group is a C$_1$-C$_{20}$ (e.g., C$_1$-C$_{12}$, C$_1$-C$_{10}$, C$_1$-C$_8$, C$_1$-C$_6$, C$_1$-C$_4$) alkyl group are intended. Examples include methylthio, ethylthio, propylthio, 1-methylethylthio, butylthio, 1-methyl-propylthio, 2-methylpropylthio, 1,1-dimethylethylthio, pentylthio, 1-methylbutylthio, 2-methylbutylthio, 3-methylbutylthio, 2,2-dio-methylpropylthio, 1-ethylpropylthio, hexylthio, 1,1-dimethyl propylthio, 1,2-dimethyl propylthio, 1-methylpentylthio, 2-methylpentylthio, 3-methyl-pentylthio, 4-methyl-pentylthio, 1,1-dimethyl butylthio, 1,2-dimethyl-butylthio, 1,3-dimethyl-butylthio, 2,2-dimethyl butylthio, 2,3-dimethyl butylthio, 3,3-dimethylbutylthio, 1-ethylbutylthio, 2-ethylbutylthio, 1,1,2-trimethyl propylthio, 1,2,2-trimethyl propylthio, 1-ethyl-1-methyl propylthio, and 1-ethyl-2-methylpropylthio.

As used herein, the term "haloalkylthio" refers to an alkylthio group as defined above wherein the carbon atoms are partially or entirely substituted with halogen atoms. Unless otherwise specified, haloalkylthio groups wherein the alkyl group is a C$_1$-C$_{20}$ (e.g., C$_1$-C$_{12}$, C$_1$-C$_{10}$, C$_1$-C$_8$, C$_1$-C$_6$, C$_1$-C$_4$) alkyl group are intended. Examples include chloromethylthio, bromomethylthio, dichloromethylthio, trichloromethylthio, fluoromethylthio, difluoromethylthio, trifluoromethylthio, chlorofluoromethylthio, dichlorofluoromethylthio, chlorodifluoromethylthio, 1-chloroethylthio, 1-bromoethylthio, 1-fluoroethylthio, 2-fluoroethylthio, 2,2-difluoroethylthio, 2,2,2-trifluoroethylthio, 2-chloro-2-fluoroethylthio, 2-chloro-2-difluoroethylthio, 2,2-dichloro-2-fluoroethylthio, 2,2,2-trichloroethylthio, pentafluoroethylthio, and 1,1,1-trifluoroprop-2-ylthio.

As used herein, the term "alkylhydroxyl" or "alkylalcohol" refers to a hydroxyl group substituted with an unsubstituted or substituted alkyl as defined above. Unless otherwise specified, in alkylhydroxyl or alkylalcohol groups, the alkyl group is a $C_1$-$C_{20}$ (e.g., $C_1$-$C_{12}$, $C_1$-$C_{10}$, $C_1$-$C_8$, $C_1$-$C_6$, $C_1$-$C_4$) alkyl group. Examples include methylalcohol, ethylalcohol, propylalcohol, 1-methylethylalcohol, butylalcohol, 1-methyl-propylalcohol, 2-methylpropylalcohol, 1,1-dimethylethylalcohol, pentylalcohol, 1-methylbutylalcohol, 2-methylbutylalcohol, 3-methylbutylalcohol, 2,2-dio-methylpropylalcohol, 1-ethylpropylalcohol, hexylalcohol, 1,1-dimethyl propylalcohol, 1,2-dimethyl propylalcohol, 1-methylpentylalcohol, 2-methylpentylalcohol, 3-methylpentylalcohol, 4-methyl-pentylalcohol, 1,1-dimethyl butylalcohol, 1,2-dimethyl-butylalcohol, 1,3-dimethyl-butylalcohol, 2,2-dimethyl butylalcohol, 2,3-dimethyl butylalcohol, 3,3-dimethylbutylalcohol, 1-ethylbutylalcohol, 2-ethylbutylalcohol, 1,1,2-trimethyl propylalcohol, 1,2,2-trimethyl propylalcohol, 1-ethyl-1-methyl propylalcohol, and 1-ethyl-2-methylpropylalcohol.

As used herein, Me refers to a methyl group; OMe refers to a methoxy group; and i-Pr refers to an isopropyl group.

As used herein, the term "halogen" including derivative terms such as "halo" refers to fluorine, chlorine, bromine and iodine.

The term "hydroxyl" as used herein is represented by the formula —OH.

The term "nitro" as used herein is represented by the formula —NO$_2$.

"$R^1$," "$R^2$," "$R^3$," "$R^n$," etc., where n is some integer, as used herein can, independently, possess one or more of the groups listed above. For example, if $R^1$ is a straight chain alkyl group, one of the hydrogen atoms of the alkyl group can optionally be substituted with a hydroxyl group, an alkoxy group, an amine group, an alkyl group, a halide, and the like. Depending upon the groups that are selected, a first group can be incorporated within second group or, alternatively, the first group can be pendant (i.e., attached) to the second group. For example, with the phrase "an alkyl group comprising an amino group," the amino group can be incorporated within the backbone of the alkyl group. Alternatively, the amino group can be attached to the backbone of the alkyl group. The nature of the group(s) that is (are) selected will determine if the first group is embedded or attached to the second group.

Unless stated to the contrary, a formula with chemical bonds shown only as solid lines and not as wedges or dashed lines contemplates each possible isomer, e.g., each enantiomer, diastereomer, and meso compound, and a mixture of isomers, such as a racemic or scalemic mixture.

A prodrug refers to a compound that is made more active in vivo. Certain compounds disclosed herein can also exist as prodrugs, as described in Hydrolysis in Drug and Prodrug Metabolism: Chemistry, Biochemistry, and Enzymology (Testa, Bernard and Mayer, Joachim M. Wiley-VHCA, Zurich, Switzerland 2003). Prodrugs of the compounds described herein are structurally modified forms of the compound that readily undergo chemical changes under physiological conditions to provide the compound. Additionally, prodrugs can be converted to the compound by chemical or biochemical methods in an ex vivo environment. For example, prodrugs can be slowly converted to a compound when placed in a transdermal patch reservoir with a suitable enzyme or chemical reagent. Prodrugs are often useful because, in some situations, they can be easier to administer than the compound, or parent drug. They can, for instance, be bioavailable by oral administration whereas the parent drug is not. The prodrug can also have improved solubility in pharmaceutical compositions over the parent drug. A wide variety of prodrug derivatives are known in the art, such as those that rely on hydrolytic cleavage or oxidative activation of the prodrug.

Prodrugs of any of the disclosed compounds include, but are not limited to, carboxylate esters, carbonate esters, hemi-esters, phosphorus esters, nitro esters, sulfate esters, sulfoxides, amides, carbamates, azo compounds, phosphamides, glycosides, ethers, acetals, and ketals. Oligopeptide modifications and biodegradable polymer derivatives (as described, for example, in *Int. J. Pharm.* 115, 61-67, 1995) are within the scope of the present disclosure. Methods for selecting and preparing suitable prodrugs are provided, for example, in the following: T. Higuchi and V. Stella, "Prodrugs as Novel Delivery Systems," Vol. 14, ACS Symposium Series, 1975; H. Bundgaard, *Design of Prodrugs,* Elsevier, 1985; and *Bioreversible Carriers in Drug Design,* ed. Edward Roche, American Pharmaceutical Association and Pergamon Press, 1987.

Reference will now be made in detail to specific aspects of the disclosed materials, compounds, compositions, articles, and methods, examples of which are illustrated in the accompanying Examples and Figures.

Compounds

Disclosed herein are arylnaphthalene lactone derivatives. Disclosed herein are compounds of Formula I:

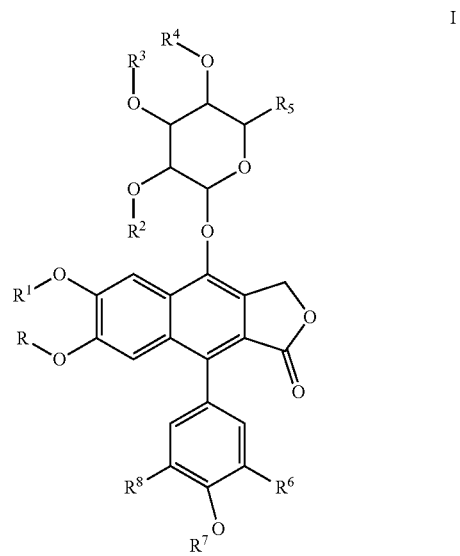

wherein

R, $R^1$, $R^2$, $R^6$, and $R^7$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R and $R^1$ taken together with the atoms to which they are attached form a substituted or unsubstituted 5 to 7 membered heterocyclic moiety, or $R^6$ and $R^7$ taken together with the atoms to which they are attached form a substituted or unsubstituted 5 to 7 membered heterocyclic moiety; $R^5$ and $R^8$ are independently hydrogen, halogen, hydroxyl, substituted or unsubstituted $C_1$-$C_6$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio;

$R^3$ is hydrogen, halogen, substituted or unsubstituted $C_1$-$C_4$ alkyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and wherein $R^3$ and $R^4$ taken together with the atoms to which they are attached form a substituted or unsubstituted 5 to 7 membered heterocyclic moiety; or $R^4$ and $R^5$ taken together with the atoms to which they are attached form a substituted or unsubstituted 5 to 7 membered heterocyclic moiety;

or a pharmaceutically acceptable salt or prodrug thereof.

In some examples of Formula I, R, $R^1$, $R^2$, $R^6$, and $R^7$ can comprise a water solubilizing group. As used herein, a water solubilizing group is a functional group that can increase the solubility of the compound in water. Examples of water solubilizing groups include, but are not limited to, phosphonyls, amino acids, succinate, poly(ethylene glycol), and the like, and combinations thereof.

In some examples of Formula I, R can be hydrogen, substituted or unsubstituted $C_1$-$C_4$ alkyl, or substituted or unsubstituted phosphonyl. For example, R can be hydrogen, $CH_3$, or $PO_3H_2$.

In some examples of Formula I, $R^1$ can be hydrogen, substituted or unsubstituted $C_1$-$C_4$ alkyl, or substituted or unsubstituted phosphonyl. For example, $R^1$ can be hydrogen, $CH_3$, or $PO_3H_2$.

In some examples of Formula I, $R^2$ can be hydrogen, substituted or unsubstituted $C_1$-$C_4$ alkyl, or substituted or unsubstituted phosphonyl. For example, $R^2$ can be hydrogen, $CH_3$, or $PO_3H_2$.

In some examples of Formula I, $R^3$ and $R^4$ taken together with the atoms to which they are attached can form a substituted or unsubstituted 5 membered heterocyclic moiety. In other examples of Formula I, $R^3$ and $R^4$ taken together with the atoms to which they are attached can form a substituted or unsubstituted 6 membered heterocyclic moiety. The heterocyclic moiety formed by $R^3$ and $R^4$ can be substituted with one or more of $C_1$-$C_6$ alkyl, $C_1$-$C_6$ alkoxy, $C_1$-$C_6$ acyl, or phosphonyl. For example, the heterocyclic moiety formed by $R^3$ and $R^4$ can be substituted with one or more of $CH_3$, $CH_2CH_3$, $OCH_3$, $C(O)CH_3$, $CO(O)CH_3$, or $PO_3H_2$.

In some examples of Formula I, when $R^3$ is hydrogen, halogen, substituted or unsubstituted $C_1$-$C_4$ alkyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, then $R^4$ and $R^5$ taken together with the atoms to which they are attached form a substituted or unsubstituted 5 to 7 membered heterocyclic moiety. For example, when $R^3$ is hydrogen, substituted or unsubstituted $C_1$-$C_4$ alkyl, or substituted or unsubstituted $C_1$-$C_4$ alkoxy, then $R^4$ and $R^5$ taken together with the atoms to which they are attached form a substituted or unsubstituted 5 to 7 membered heterocyclic moiety. In some examples, $R^4$ and $R^5$ taken together with the atoms to which they are attached form a substituted or unsubstituted 6 membered heterocyclic moiety.

In some examples of Formula I, $R^5$ can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ can be hydrogen, hydroxyl, $OCH_3$, $CH_2OCH_3$, or $CH_2OH$. In some examples, $R^5$ can be a water solubilizing group.

In some examples of Formula I, $R^6$ can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^6$ can be hydrogen, hydroxyl, $OCH_3$, $CH_2OCH_3$, or $CH_2OH$. In some examples, $R^6$ can be a water solubilizing group.

In some examples of Formula I, $R^6$ and $R^7$ taken together with the atoms to which they are attached can form a 5 membered heterocyclic moiety.

In some examples of Formula I, $R^8$ can be hydrogen, substituted or unsubstituted $C_1$-$C_4$ alkyl, or substituted or unsubstituted phosphonyl. For example, $R^8$ can be hydrogen, $CH_3$, or $PO_3H_2$.

In some examples of Formula I, the compound can have a structure according to Formula I-A, or a pharmaceutically acceptable salt or prodrug thereof:

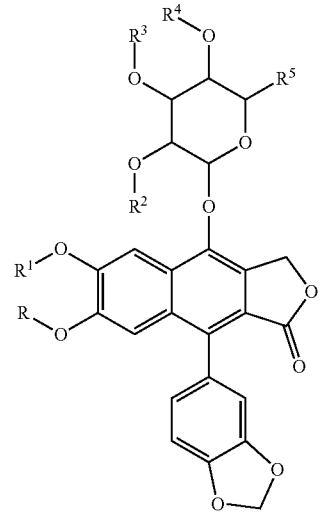

I-A wherein

R, $R^1$, and $R^2$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R and $R^1$ taken together with the atoms to which they are attached form a substituted or unsubstituted 5 to 7 membered heterocyclic moiety;

$R^5$ is hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^3$ and $R^4$ taken together with the atoms to which they are attached form a substituted or unsubstituted 5 to 7 membered heterocyclic moiety.

In some examples of Formula I-A, R, $R^1$, and $R^2$ can comprise a water solubilizing group.

In some examples of Formula I-A, R can be hydrogen, substituted or unsubstituted $C_1$-$C_4$ alkyl, or substituted or unsubstituted phosphonyl. For example, R can be hydrogen, $CH_3$, or $PO_3H_2$.

In some examples of Formula I-A, $R^1$ can be hydrogen, substituted or unsubstituted $C_1$-$C_4$ alkyl, or substituted or unsubstituted phosphonyl. For example, $R^1$ can be hydrogen, $CH_3$, or $PO_3H_2$.

In some examples of Formula I-A, $R^2$ can be hydrogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, or substituted or unsubstituted phosphonyl. For example, $R^2$ can be hydrogen, $CH_3$, benzyl, or $PO_3H_2$.

In some examples of Formula I-A, $R^3$ and $R^4$ taken together with the atoms to which they are attached can form a substituted or unsubstituted 5 membered heterocyclic moiety. In other examples of Formula I-A, $R^3$ and $R^4$ taken together with the atoms to which they are attached can form a substituted or unsubstituted 6 membered heterocyclic moiety. The heterocyclic moiety formed by $R^3$ and $R^4$ can be substituted with one or more of $C_1$-$C_6$ alkyl, $C_1$-$C_6$ alkoxy, $C_1$-$C_6$ acyl, or phosphonyl. For example, the heterocyclic moiety formed by $R^3$ and $R^4$ can be substituted with one or more of $CH_3$, $CH_2CH_3$, $OCH_3$, $C(O)CH_3$, $CO(O)CH_3$, or $PO_3H_2$.

In some examples of Formula I-A, $R^5$ can be hydrogen, hydroxyl, substituted or unsubstituted $C_1$-$C_6$ alkyl, substituted or unsubstituted alkenyl, substituted or unsubstituted alkynyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ can be hydrogen, hydroxyl, $OCH_3$, $CH_2OCH_3$, $CH_2OH$, or $CH_2CH_2OH$. In some examples, $R^5$ can be a water solubilizing group.

In some examples of Formula I, the compound can have a structure according to Formula I-B, or a pharmaceutically acceptable salt or prodrug thereof:

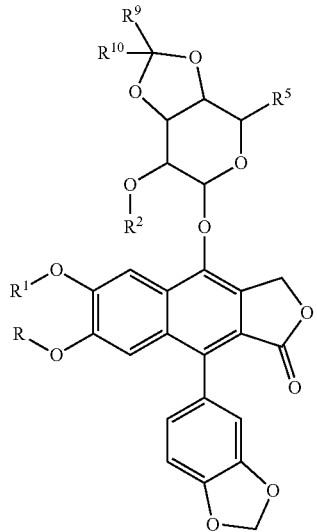

I-B wherein R, $R^1$, and $R^2$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R and $R^1$ taken together with the atoms to which they are attached form a substituted or unsubstituted 5 to 7 membered heterocyclic moiety;

$R^5$ is hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^9$ and $R^{10}$ are independently hydrogen, halogen, hydroxyl, substituted or unsubstituted $C_1$-$C_6$ alkyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ alkylhydroxyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, substituted or unsubstituted thio, or $R^9$ and $R^{10}$ taken together with the atoms to which they are attached form a substituted or unsubstituted 5 to 7 membered cyclic moiety.

In some examples of Formula I-B, R, $R^1$, and $R^2$ can comprise a water solubilizing group.

In some examples of Formula I-B, R can be hydrogen, substituted or unsubstituted $C_1$-$C_4$ alkyl, or substituted or unsubstituted phosphonyl. For example, R can be hydrogen, $CH_3$, or $PO_3H_2$.

In some examples of Formula I-B, $R^1$ can be hydrogen, substituted or unsubstituted $C_1$-$C_4$ alkyl, or substituted or unsubstituted phosphonyl. For example, $R^1$ can be hydrogen, $CH_3$, or $PO_3H_2$.

In some examples of Formula I-B, $R^2$ can be hydrogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, or substituted or unsubstituted phosphonyl. For example, $R^2$ can be hydrogen, $CH_3$, phenyl, benzyl, or $PO_3H_2$.

In some examples of Formula I-B, $R^5$ can be hydrogen, hydroxyl, substituted or unsubstituted $C_1$-$C_6$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ can be hydrogen, hydroxyl, $OCH_3$, OCCH, $CH_2OCH_3$, or $CH_2OH$. In some examples, $R^5$ can be a water solubilizing group.

In some examples of Formula I-B, $R^9$ and $R^{10}$ can be independently hydrogen, substituted or unsubstituted $C_1$-$C_6$ alkyl, substituted or unsubstituted $C_1$-$C_6$ alkoxy, substituted or unsubstituted $C_1$-$C_6$ alkylhydroxyl, substituted or unsubstituted $C_1$-$C_6$ ether, or $R^9$ and $R^{10}$ taken together with the atoms to which they are attached form a substituted or unsubstituted 5 to 7 membered cyclic moiety. For example, $R^9$ and $R^{10}$ can be independently hydrogen, $CH_3$, $OCH_3$, $CH_2OCH_3$, or —$CH_2OH$. In some examples, $R^9$ and $R^{10}$ are independently a water solubilizing group. In some examples of Formula I-B, $R^9$ and $R^{10}$ taken together with the atoms to which they are attached form an unsubstituted 5 to 7 membered cyclic moiety.

In some examples of Formula I, the compound can have a structure according to Formula I-C, or a pharmaceutically acceptable salt or prodrug thereof

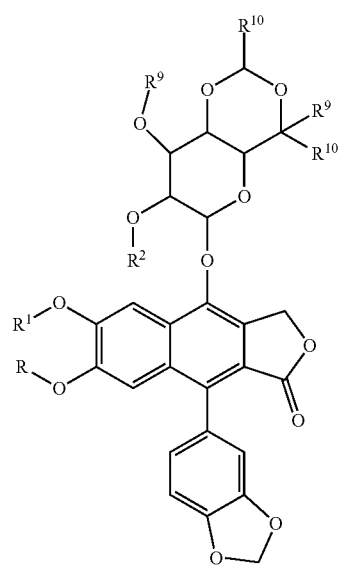

I-C wherein $R^9$ and $R^{10}$ are independently hydrogen, halogen, hydroxyl, substituted or unsubstituted $C_1$-$C_6$ alkyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ alkylhydroxyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio.

In some examples of Formula I-C, R, $R^1$, and $R^2$ can be as described herein.

For example, in some examples of Formula I-C, R, $R^1$, and $R^2$ can comprise a water solubilizing group.

In some examples of Formula I-C, R can be hydrogen, substituted or unsubstituted $C_1$-$C_4$ alkyl, or substituted or unsubstituted phosphonyl. For example, R can be hydrogen, $CH_3$, or $PO_3H_2$.

In some examples of Formula I-C, $R^1$ can be hydrogen, substituted or unsubstituted $C_1$-$C_4$ alkyl, or substituted or unsubstituted phosphonyl. For example, $R^1$ can be hydrogen, $CH_3$, or $PO_3H_2$.

In some examples of Formula I-C, $R^2$ can be hydrogen, substituted or unsubstituted $C_1$-$C_4$ alkyl, or substituted or unsubstituted phosphonyl. For example, $R^2$ can be hydrogen, $CH_3$, or $PO_3H_2$.

In some examples of Formula I-C, $R^9$ and $R^{10}$ can be independently hydrogen, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^9$ and $R^{10}$ can be independently hydrogen, $CH_3$, $OCH_3$, $CH_2OCH_3$, or —$CH_2OH$. In specific examples, $R^9$ and $R^{10}$ can be both $CH_3$. In other specific examples, $R^9$ and $R^{10}$ can be independently a substituted or unsubstituted phosphonyl, substituted or unsubstituted sulfinyl, substituted or unsubstituted sulfonyl, or substituted or unsubstituted sulfonamide.

In some examples of Formula I, the compound can have a structure below, or a pharmaceutically acceptable salt or prodrug thereof:

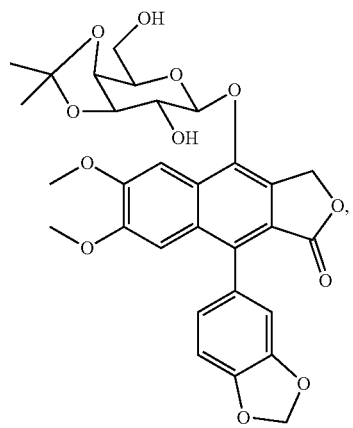

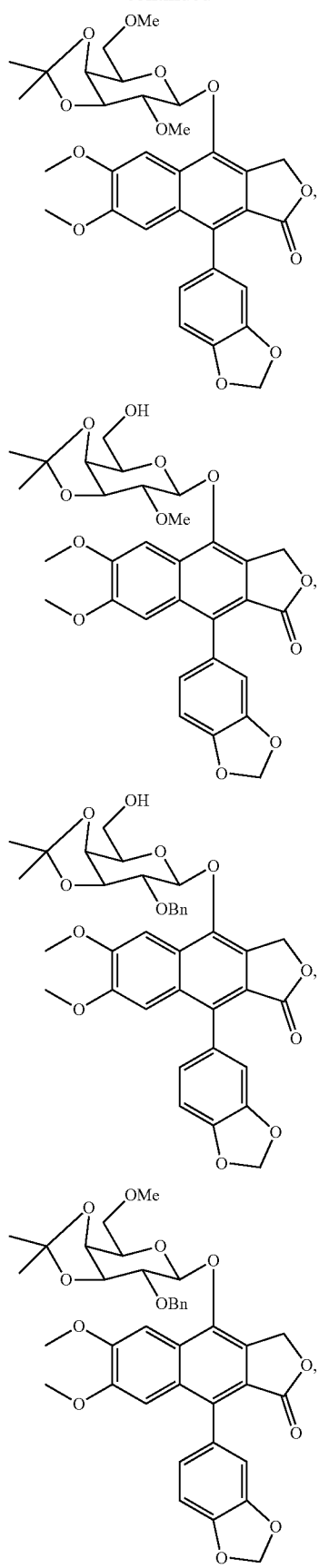
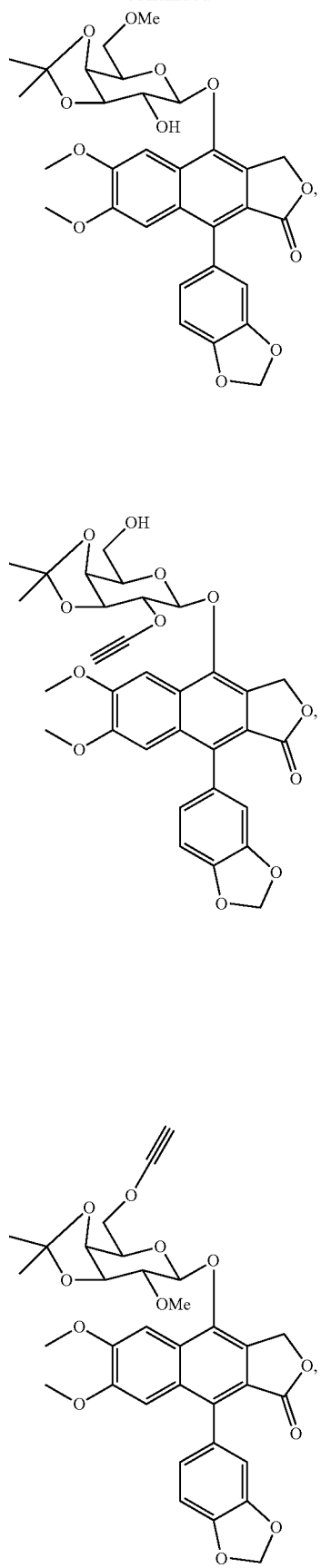

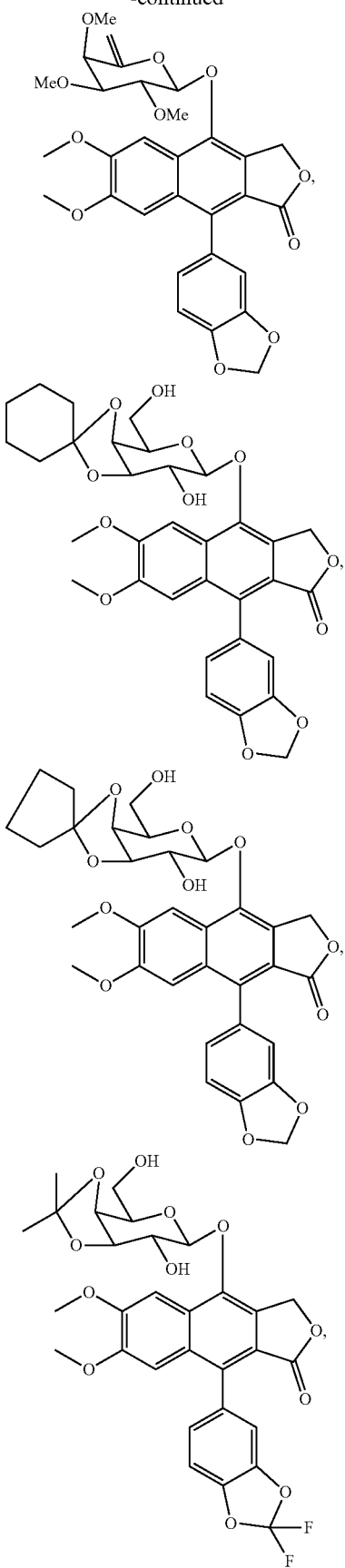
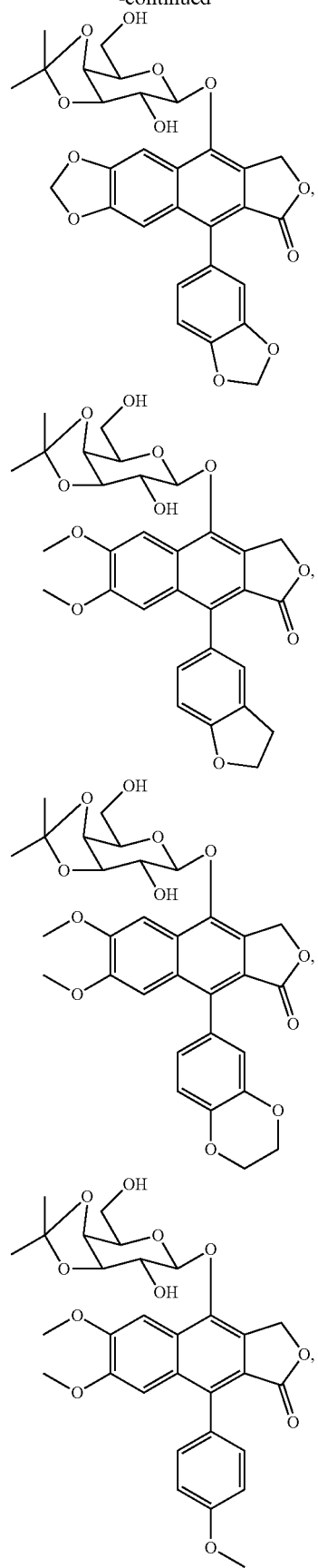

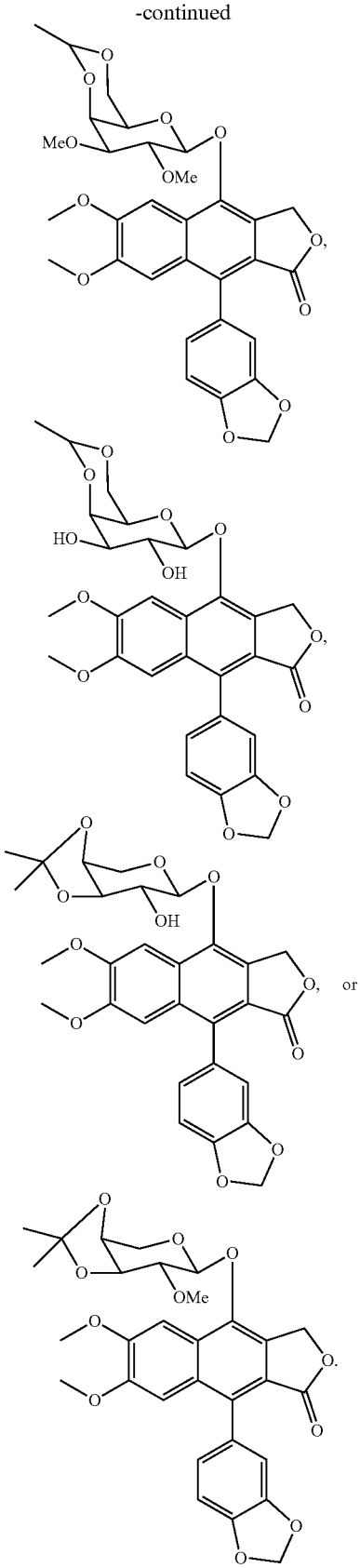

Also disclosed herein are compounds of Formula II or a pharmaceutically acceptable salt or prodrug thereof:

II wherein

R, $R^1$, $R^6$, and $R^7$ can be independently hydrogen, halogen, substituted or unsubstituted $C_1$-$C_4$ alkyl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, R and $R^1$ taken together with the atoms to which they are attached form a substituted or unsubstituted 5 to 7 membered heterocyclic moiety, or $R^6$ and $R^7$ taken together with the atoms to which they are attached form a substituted or unsubstituted 5 to 7 membered heterocyclic moiety;

$R^8$ and $R^{14}$ are independently hydrogen, halogen, hydroxyl, substituted or unsubstituted $C_1$-$C_6$ alkyl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{13}$ is a substituted or unsubstituted aryloxy, substituted or unsubstituted arylalkyl ether, substituted or unsubstituted heteroaryloxy, substituted or unsubstituted heteroarylalkyl ether, substituted or unsubstituted $C_2$-$C_6$ alkenyl, or substituted or unsubstituted $C_2$-$C_6$ diol.

In some examples of Formula II, one or more of R, $R^1$, $R^6$, and $R^7$ are water solubilizing groups. In some examples, $R^1$ can be a water solubilizing group.

In some examples of Formula II, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$ or $PO_3H_2$.

In some examples of Formula II, $R^6$ and $R^7$ taken together with the atoms to which they are attached can form a 5 membered heterocyclic moiety.

In some examples of Formula II, $R^8$ and $R^{14}$ can be independently hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^8$ and $R^{14}$ can be independently hydrogen, hydroxyl, $OCH_3$, $CH_2OCH_3$ or $CH_2OH$.

In some examples of Formula II, $R^{13}$ can be substituted or unsubstituted $C_6H_5CH_2O$, substituted or unsubstituted $C_6H_5CH_2OCH_2$, $C_2$-$C_4$ alkenyl, 1,2-ethanediol, or 1,2-propanediol.

In some examples of Formula II, the compound can be Formula II-A or a pharmaceutically acceptable salt or prodrug thereof:

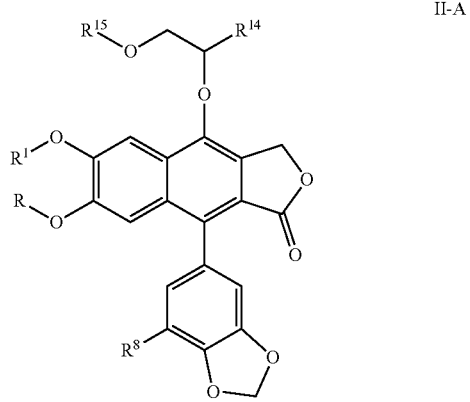

II-A wherein

R and $R^1$ can be independently hydrogen, halogen, substituted or unsubstituted $C_1$-$C_4$ alkyl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R and $R^1$ taken together with the atoms to which they are attached form a substituted or unsubstituted 5 to 7 membered heterocyclic moiety;

$R^8$ and $R^{14}$ can be independently hydrogen, halogen, hydroxyl, substituted or unsubstituted $C_1$-$C_6$ alkyl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{15}$ can be substituted or unsubstituted aryl or substituted or unsubstituted heteroaryl.

In some examples of Formula II-A, one or more of R and $R^1$, can be water solubilizing groups. In some examples, $R^1$ can be a water solubilizing group.

In some examples of Formula II-A, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula II-A, $R^8$ and $R^{14}$ can be independently hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^8$ and $R^{14}$ can be independently hydrogen, hydroxyl, $OCH_3$, $CH_2OCH_3$, or $CH_2OH$.

In some examples of Formula II-A, $R^{15}$ can be substituted or unsubstituted benzyl ($C_6H_5CH_2$) or substituted or unsubstituted $C_6H_5CH_2CH_2$.

In some examples of Formula II, the compound can be Formula II-B or a pharmaceutically acceptable salt or prodrug thereof:

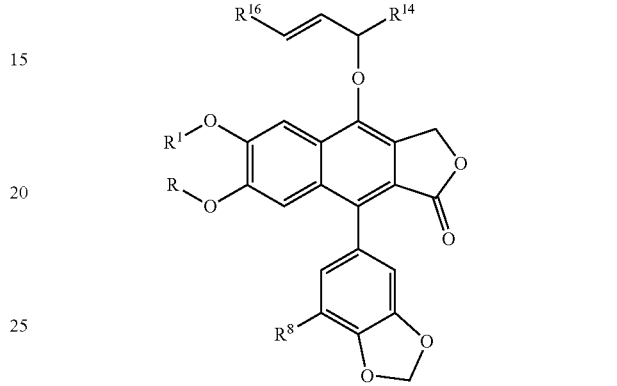

II-B wherein

R and $R^1$ can be independently hydrogen, halogen, substituted or unsubstituted $C_1$-$C_4$ alkyl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R and $R^1$ taken together with the atoms to which they are attached form a substituted or unsubstituted 5 to 7 membered heterocyclic moiety;

$R^8$ and $R^{14}$ can be independently hydrogen, halogen, hydroxyl, substituted or unsubstituted $C_1$-$C_6$ alkyl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{16}$ can be hydrogen, halogen, substituted or unsubstituted $C_1$-$C_6$ alkyl, substituted or unsubstituted $C_1$-$C_6$ alkenyl, substituted or unsubstituted $C_1$-$C_6$ alkoxy, substituted or unsubstituted $C_1$-$C_6$ alkoxycarbonyl, hydroxycarbonyl, $C_1$-$C_6$ alkylhydroxyl, substituted or unsubstituted $C_1$-$C_6$ acyl, or substituted or unsubstituted $C_1$-$C_6$ ether.

In some examples of Formula II-B, one or more of R and $R^1$, can be water solubilizing groups. In some examples, $R^1$ can be a water solubilizing group.

In some examples of Formula II-B, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula II-B, $R^8$ and $R^{14}$ can be independently hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^8$ and $R^{14}$ can be independently hydrogen, hydroxyl, $OCH_3$, $CH_2OCH_3$, or $CH_2OH$.

In some examples of Formula II-B, $R^{16}$ can be hydrogen or substituted or unsubstituted $C_1$-$C_6$ alkyl.

In some examples of Formula II, the compound can be Formula II-C or a pharmaceutically acceptable salt or prodrug thereof:

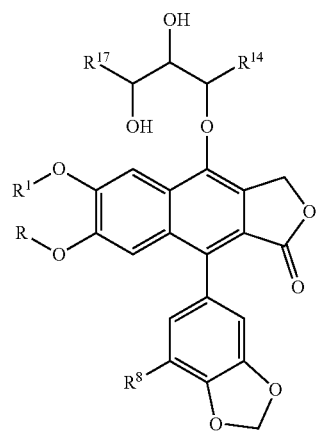

II-C wherein

R and $R^1$ can be independently hydrogen, halogen, substituted or unsubstituted $C_1$-$C_4$ alkyl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R and $R^1$ taken together with the atoms to which they are attached form a substituted or unsubstituted 5 to 7 membered heterocyclic moiety;

$R^8$ and $R^{14}$ can be independently hydrogen, halogen, hydroxyl, substituted or unsubstituted $C_1$-$C_6$ alkyl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{17}$ can be hydrogen, substituted or unsubstituted $C_1$-$C_6$ alkyl, substituted or unsubstituted $C_1$-$C_6$ alkenyl, substituted or unsubstituted $C_1$-$C_6$ alkoxy, substituted or unsubstituted $C_1$-$C_6$ alkoxycarbonyl, hydroxycarbonyl, $C_1$-$C_6$ alkylhydroxyl, substituted or unsubstituted $C_1$-$C_6$ acyl, or substituted or unsubstituted $C_1$-$C_6$ ether.

In some examples of Formula II-C, one or more of R and $R^1$, can be water solubilizing groups. In some examples, $R^1$ can be a water solubilizing group.

In some examples of Formula II-C, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula II-C, $R^8$ and $R^{14}$ can be independently hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^8$ and $R^{14}$ can be independently hydrogen, hydroxyl, $OCH_3$, $CH_2OCH_3$, or $CH_2OH$.

In some examples of Formula II-C, $R^{17}$ can be hydrogen or substituted or unsubstituted $C_1$-$C_6$ alkyl.

Also disclosed herein are compounds of Formula III or a pharmaceutically acceptable salt or prodrug thereof:

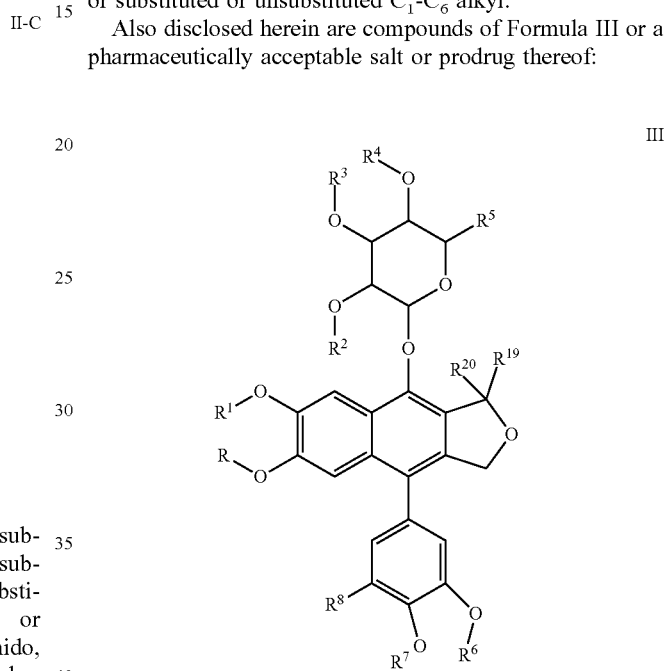

III wherein

R, $R^1$, $R^2$, $R^3$, $R^4$, $R^6$, and $R^7$ can be independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or one or more of R and $R^1$, $R^3$ and $R^4$ or $R^6$ and $R^7$ taken together with the atoms to which they are attached form a substituted or unsubstituted 5 to 7 membered heterocyclic moiety;

$R^5$ and $R^8$ can be independently hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{19}$ and $R^{20}$ can be hydrogen or $R^{19}$ and $R^{20}$ taken together with the atoms to which they are attached form C=O.

In some examples of Formula III, one or more of R, $R^1$, $R^2$, $R^3$, $R^4$, $R^6$, and $R^7$ can be water solubilizing groups. In some examples, $R^1$ can be a water solubilizing group.

In some examples of Formula III, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula III, $R^2$, $R^3$, and $R^4$ can be independently hydrogen, hydroxyl, substituted or unsubstituted $C_1$-$C_6$ alkyl, or substituted or unsubstituted $C_1$-$C_4$ alkylcarbonyl. For example, $R^2$, $R^3$, and $R^4$ can be independently hydrogen, hydroxyl, $CH_3$, $C(O)CH_3$, or $C(O)CH_2CH_3$.

In some examples of Formula III, $R^5$ and $R^8$ can be independently can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ and $R^8$ can be independently hydrogen, hydroxyl, $OCH_3$, $CH_2OCH_3$, or $CH_2OH$.

In some examples of Formula III, $R^6$ and $R^7$ taken together with the atoms to which they are attached can form a 5 membered heterocyclic moiety.

In some examples of Formula III, $R^{19}$ and $R^{20}$ can be hydrogen.

In some examples of Formula III, $R^{19}$ and $R^{20}$ taken together with the atoms to which they are attached can form C=O.

In some examples of Formula III, the compound can be Formula III-A or a pharmaceutically acceptable salt or prodrug thereof:

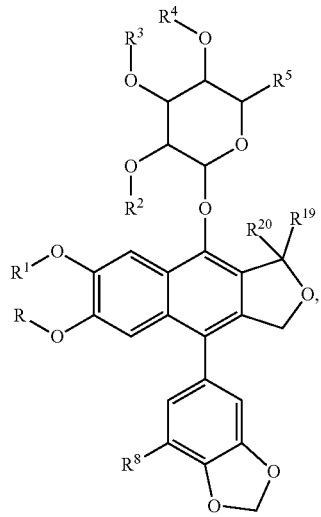

III-A wherein

R, $R^1$, $R^2$, $R^3$, and $R^4$ can be independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or one or more of R and $R^1$, $R^3$ and $R^4$ or $R^3$ and $R^4$ taken together with the atoms to which they are attached form a substituted or unsubstituted 5 to 7 membered heterocyclic moiety;

$R^5$ and $R^8$ can be independently hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{19}$ and $R^{20}$ can be hydrogen or $R^{19}$ and $R^{20}$ taken together with the atoms to which they are attached form C=O.

In some examples of Formula III-A, one or more of R, $R^1$, $R^2$, $R^3$, and $R^4$ can be water solubilizing groups. In some examples, $R^1$ can be a water solubilizing group.

In some examples of Formula III-A, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula III-A, $R^2$, $R^3$, and $R^4$ can be independently hydrogen, hydroxyl, substituted or unsubstituted $C_1$-$C_6$ alkyl, or substituted or unsubstituted $C_1$-$C_4$ alkylcarbonyl. For example, $R^2$, $R^3$, and $R^4$ can be independently hydrogen, hydroxyl, $CH_3$, $C(O)CH_3$, or $C(O)CH_2CH_3$.

In some examples of Formula III-A, $R^5$ and $R^8$ can be independently can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ and $R^8$ can be independently hydrogen, hydroxyl, $OCH_3$, $CH_2OCH_3$, or $CH_2OH$.

In some examples of Formula III-A, $R^{19}$ and $R^{20}$ can be hydrogen.

In some examples of Formula III-A, $R^{19}$ and $R^{20}$ taken together with the atoms to which they are attached can form C=O.

In some examples of Formula III, the compound can be Formula III-B or a pharmaceutically acceptable salt or prodrug thereof:

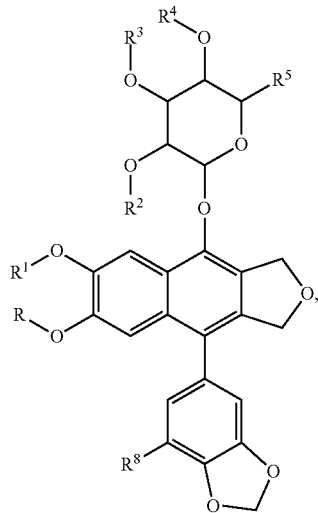

III-B wherein

R, $R^1$, $R^2$, $R^3$, and $R^4$ can be independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or one or more of R and $R^1$, $R^3$ and $R^4$ or $R^3$ and $R^4$ taken together with the atoms to which they are attached form a substituted or unsubstituted 5 to 7 membered heterocyclic moiety; and $R^5$ and $R^8$ can be independently hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio.

In some examples of Formula III-B, one or more of R, $R^1$, $R^2$, $R^3$, and $R^4$ can be water solubilizing groups. In some examples, $R^1$ can be a water solubilizing group.

In some examples of Formula III-B, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula III-B, $R^2$, $R^3$, and $R^4$ can be independently hydrogen, hydroxyl, substituted or unsubstituted $C_1$-$C_6$ alkyl, or substituted or unsubstituted $C_1$-$C_4$ alkylcarbonyl. For example, $R^2$, $R^3$, and $R^4$ can be independently hydrogen, hydroxyl, $CH_3$, $C(O)CH_3$, or $C(O)CH_2CH_3$.

In some examples of Formula III-B, $R^5$ and $R^8$ can be independently can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ and $R^8$ can be independently hydrogen, hydroxyl, $OCH_3$, $CH_2OCH_3$, or $CH_2OH$.

In some examples of Formula III, the compound can be Formula III-C or a pharmaceutically acceptable salt or prodrug thereof:

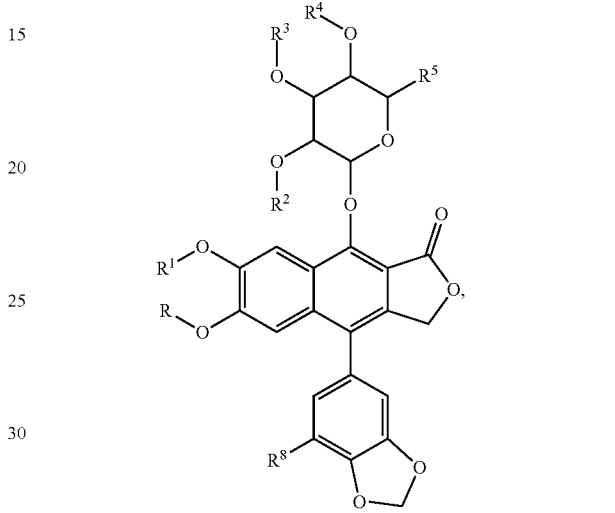

III-C wherein

R, $R^1$, $R^2$, $R^3$, and $R^4$ can be independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or one or more of R and $R^1$, $R^3$ and $R^4$ or $R^3$ and $R^4$ taken together with the atoms to which they are attached form a substituted or unsubstituted 5 to 7 membered heterocyclic moiety; and $R^5$ and $R^8$ can be independently hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio.

In some examples of Formula III-C, one or more of R, $R^1$, $R^2$, $R^3$, and $R^4$ can be water solubilizing groups. In some examples, $R^1$ can be a water solubilizing group.

In some examples of Formula III-C, R and $R^1$ can be independently hydrogen, substituted or unsubstituted $C_1$-$C_4$ alkyl, or substituted or unsubstituted phosphonyl. For example, R and $R^1$ can be independently hydrogen, $CH_3$, or $PO_3H_2$.

In some examples of Formula III-C, $R^2$, $R^3$, and $R^4$ can be independently hydrogen, hydroxyl, substituted or unsubstituted $C_1$-$C_6$ alkyl, or substituted or unsubstituted $C_1$-$C_4$ alkylcarbonyl. For example, $R^2$, $R^3$, and $R^4$ can be independently hydrogen, hydroxyl, $CH_3$, $C(O)CH_3$, or $C(O)CH_2CH_3$.

In some examples of Formula III-C, $R^5$ and $R^8$ can be independently can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ and $R^8$ can be independently hydrogen, hydroxyl, $OCH_3$, $CH_2OCH_3$, or $CH_2OH$.

Also disclosed herein are compounds of Formula IV or a pharmaceutically acceptable salt or prodrug thereof:

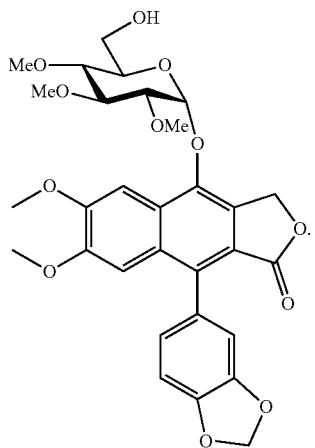

IV

Also disclosed herein are compounds of Formula V or a pharmaceutically acceptable salt or prodrug thereof:

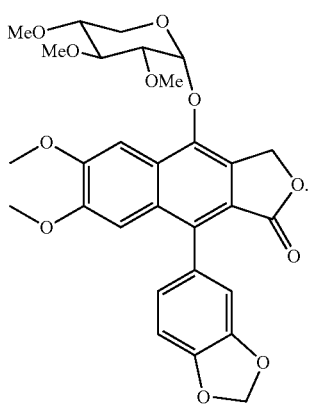

V

Also disclosed herein are compounds of Formula VI or a pharmaceutically acceptable salt or prodrug thereof:

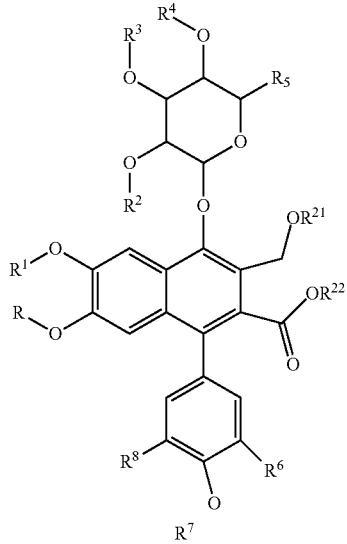

VI wherein

R, $R^1$, $R^2$, $R^6$, $R^7$, $R^{21}$, and $R^{22}$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, R and $R^1$ taken together with the atoms to which they are attached form a substituted or unsubstituted 5 to 7 membered heterocyclic moiety, or $R^6$ and $R^7$ taken together with the atoms to which they are attached form a substituted or unsubstituted 5 to 7 membered heterocyclic moiety;

$R^5$ and $R^8$ are independently hydrogen, halogen, hydroxyl, substituted or unsubstituted $C_1$-$C_6$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^3$ and $R^4$ are independently hydrogen, halogen, substituted or unsubstituted $C_1$-$C_4$ alkyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or R³ and R⁴ taken together with the atoms to which they are attached form a substituted or unsubstituted 5 to 7 membered heterocyclic moiety, or R⁴ and R⁵ taken together with the atoms to which they are attached form a substituted or unsubstituted 5 to 7 membered heterocyclic moiety.

In some examples of Formula VI, R and R¹ can be both CH₃.

In some examples of Formula VI, R² can be H or CH₃.

In some examples of Formula VI, R³ and R⁴ taken together with the atoms to which they are attached form a substituted or unsubstituted 5 membered heterocyclic moiety. For example, R³ and R⁴ taken together with the atoms to which they are attached form a substituted or unsubstituted 6 membered heterocyclic moiety. In specific examples, the heterocyclic moiety formed by R³ and R⁴ is substituted with a $C_1$-$C_6$ alkyl, $C_1$-$C_6$ alkoxy, $C_1$-$C_6$ acyl, or phosphonyl. In other specific examples of Formula VI, the heterocyclic moiety formed by R³ and R⁴ is substituted with CH₃, OCH₃, C(O)CH₃, CO(O)CH₃, or PO₃H₂.

In some examples of Formula VI, R⁵ can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, R⁵ can be hydrogen, hydroxyl, OCH₃, CH₂OCH₃, or CH₂OH. In some examples, R⁵ can be substituted or unsubstituted phosphonyl, substituted or unsubstituted sulfinyl, substituted or unsubstituted sulfonyl, or substituted or unsubstituted sulfonamide.

In some examples of Formula VI, R⁶ and R⁷ taken together with the atoms to which they are attached form a 5 membered heterocyclic moiety.

In some examples of Formula VI, R⁸ is hydrogen, CH₃, or PO₃H₂.

In some examples of Formula VI, $R^{21}$ and $R^{22}$ can be independent selected from hydrogen or substituted or unsubstituted $C_1$-$C_4$ alkyl. For example, $R^{21}$ and $R^{22}$ can be unsubstituted $C_1$-$C_4$ alkyl such as $C_1$ alkyl.

In some examples of Formula VI, the compound can have a structure below, or a pharmaceutically acceptable salt or prodrug thereof:

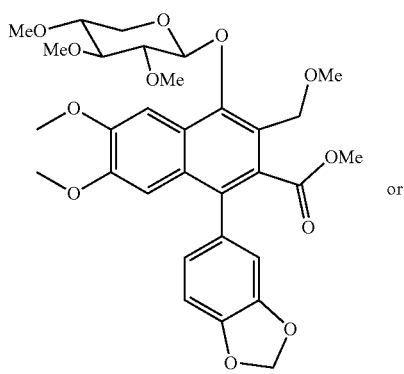

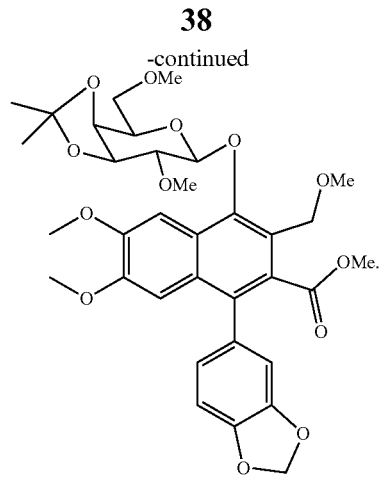

Also disclosed herein are compounds of Formula VII or a pharmaceutically acceptable salt or prodrug thereof:

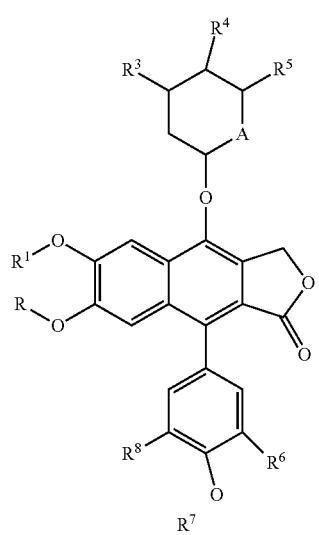

VII wherein

A can be CH₂ or O;

R, R¹, R⁶, and R⁷ can be independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, R and R¹ taken together with the atoms to which they are attached form a substituted or unsubstituted 5 to 7 membered heterocyclic moiety, or R⁶ and R⁷ taken together with the atoms to which they are attached form a substituted or unsubstituted 5 to 7 membered heterocyclic moiety;

R⁸ can be hydrogen, halogen, hydroxyl, substituted or unsubstituted $C_1$-$C_6$ alkyl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^3$ and $R^4$ can be independently hydrogen, halogen, substituted or unsubstituted $C_1$-$C_4$ alkyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or $R^3$ and $R^4$ taken together with the atoms to which they are attached form a substituted or unsubstituted 5 to 7 membered heterocyclic moiety; and $R^5$ can be independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or $R^4$ and $R^5$ taken together with the atoms to which they are attached form a substituted or unsubstituted 5 to 7 membered heterocyclic moiety.

In some examples of Formula VII, A can be $CH_2$.

In some examples of Formula VII, R and $R^1$ are both $CH_3$.

In some examples of Formula VII, $R^2$ can be H or $CH_3$.

In some examples of Formula VII, $R^3$ and $R^4$ taken together with the atoms to which they are attached form a substituted or unsubstituted 5 membered heterocyclic moiety. For example, $R^3$ and $R^4$ taken together with the atoms to which they are attached form a substituted or unsubstituted 6 membered heterocyclic moiety. In specific examples, the heterocyclic moiety formed by $R^3$ and $R^4$ is substituted with a $C_1$-$C_6$ alkyl, $C_1$-$C_6$ alkoxy, $C_1$-$C_6$ acyl, or phosphonyl. In other specific examples of Formula VII, the heterocyclic moiety formed by $R^3$ and $R^4$ is substituted with $CH_3$, $OCH_3$, $C(O)CH_3$, $CO(O)CH_3$, or $PO_3H_2$.

In some examples of Formula VII, $R^3$ and $R^4$ are both hydrogen.

In some examples of Formula VII, $R^5$ can be hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether. For example, $R^5$ can be hydrogen, hydroxyl, $OCH_3$, $CH_2OCH_3$, or $CH_2OH$. In some examples, $R^5$ can be substituted or unsubstituted phosphonyl, substituted or unsubstituted sulfinyl, substituted or unsubstituted sulfonyl, or substituted or unsubstituted sulfonamide.

In some examples of Formula VII, $R^6$ and $R^7$ taken together with the atoms to which they are attached form a 5 membered heterocyclic moiety.

In some examples of Formula VII, $R^8$ is hydrogen, $CH_3$, or $PO_3H_2$.

In some examples of Formula VI, $R^{21}$ and $R^{22}$ can be independent selected from hydrogen or substituted or unsubstituted $C_1$-$C_4$ alkyl. For example, $R^{21}$ and $R^{22}$ can be unsubstituted $C_1$-$C_4$ alkyl such as $C_1$ alkyl.

In some examples of Formula VII, the compound can have a structure below, or a pharmaceutically acceptable salt or prodrug thereof:

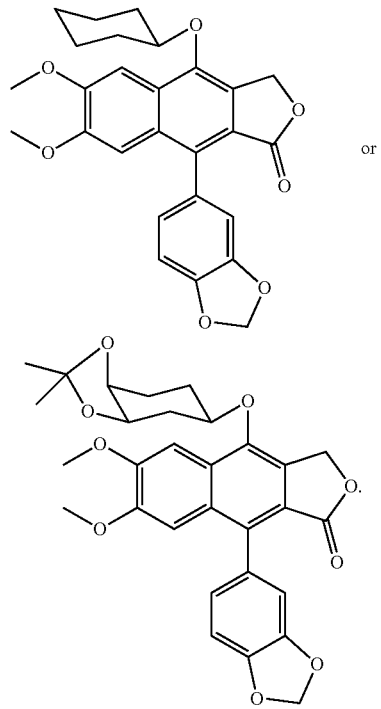

or

Pharmaceutical Compositions

The compounds described herein or derivatives thereof can be provided in a pharmaceutical composition. In some embodiments, the composition can include a compound of any one of Formulas I-VII. In some embodiments, the composition can include a compound as described in FIG. 1. In some embodiments, the composition can include a compound as described in FIG. 2.

Depending on the intended mode of administration, the pharmaceutical composition can be in the form of solid, semi-solid or liquid dosage forms, such as, for example, tablets, suppositories, pills, capsules, powders, liquids, or suspensions, preferably in unit dosage form suitable for single administration of a precise dosage. The compositions will include a therapeutically effective amount of the compound described herein or derivatives thereof in combination with a pharmaceutically acceptable carrier and, in addition, can include other medicinal agents, pharmaceutical agents, carriers, or diluents. By pharmaceutically acceptable is meant a material that is not biologically or otherwise undesirable, which can be administered to an individual along with the selected compound without causing unacceptable biological effects or interacting in a deleterious manner with the other components of the pharmaceutical composition in which it is contained.

As used herein, the term carrier encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., *Remington's Pharmaceutical Sciences*, 21st Edition, ed. University of the Sciences in Philadelphia, Lippincott, Williams & Wilkins, Philadelphia, Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

Compositions containing the compound described herein or derivatives thereof suitable for parenteral injection can comprise physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers, diluents, solvents or vehicles include water, ethanol, polyols (propyleneglycol, polyethyleneglycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions and by the use of surfactants.

These compositions can also contain adjuvants such as preserving, wetting, emulsifying, and dispensing agents. Prevention of the action of microorganisms can be promoted by various antibacterial and antifungal agents, for example, parabens, chlorobutanol, phenol, sorbic acid, and the like. Isotonic agents, for example, sugars, sodium chloride, and the like can also be included. Prolonged absorption of the injectable pharmaceutical form can be brought about by the use of agents delaying absorption, for example, aluminum monostearate and gelatin.

Solid dosage forms for oral administration of the compounds described herein or derivatives thereof include capsules, tablets, pills, powders, and granules. In such solid dosage forms, the compounds described herein or derivatives thereof is admixed with at least one inert customary excipient (or carrier) such as sodium citrate or dicalcium phosphate or (a) fillers or extenders, as for example, starches, lactose, sucrose, glucose, mannitol, and silicic acid, (b) binders, as for example, carboxymethylcellulose, alginates, gelatin, polyvinylpyrrolidone, sucrose, and acacia, (c) humectants, as for example, glycerol, (d) disintegrating agents, as for example, agar-agar, calcium carbonate, potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, and glycerol monostearate, (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms can also comprise buffering agents.

Solid compositions of a similar type can also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others known in the art. They can contain opacifying agents and can also be of such composition that they release the active compound or compounds in a certain part of the intestinal tract in a delayed manner. Examples of embedding compositions that can be used are polymeric substances and waxes. The active compounds can also be in micro-encapsulated form, if appropriate, with one or more of the above-mentioned excipients. The disclosed compounds can also be incorporated into polymers, examples of which include poly (D-L lactide-co-glycolide) polymer for intracranial tumors; poly[bis(pcarboxyphenoxy) propane:sebacic acid] in a 20:80 molar ratio (as used in GLIADEL); chondroitin; chitin; and chitosan.

Liquid dosage forms for oral administration of the compounds described herein or derivatives thereof include pharmaceutically acceptable emulsions, solutions, suspensions, syrups, and elixirs. In addition to the active compounds, the liquid dosage forms can contain inert diluents commonly used in the art, such as water or other solvents, solubilizing agents, and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil, sesame oil, glycerol, tetrahydrofurfuryl alcohol, polyethyleneglycols, and fatty acid esters of sorbitan, or mixtures of these substances, and the like.

Besides such inert diluents, the composition can also include additional agents, such as wetting, emulsifying, suspending, sweetening, flavoring, or perfuming agents.

Suspensions, in addition to the active compounds, can contain additional agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions of the compounds described herein or derivatives thereof for rectal administrations are optionally suppositories, which can be prepared by mixing the compounds with suitable non-irritating excipients or carriers such as cocoa butter, polyethyleneglycol or a suppository wax, which are solid at ordinary temperatures but liquid at body temperature and therefore, melt in the rectum or vaginal cavity and release the active component.

Dosage forms for topical administration of the compounds described herein or derivatives thereof include ointments, powders, sprays, and inhalants. The compounds described herein or derivatives thereof are admixed under sterile conditions with a physiologically acceptable carrier and any preservatives, buffers, or propellants as can be required. Ophthalmic formulations, ointments, powders, and solutions are also contemplated as being within the scope of the compositions.

The compositions can include one or more of the compounds described herein and a pharmaceutically acceptable carrier. As used herein, the term pharmaceutically acceptable salt refers to those salts of the compound described herein or derivatives thereof that are, within the scope of sound medical judgment, suitable for use in contact with the tissues of subjects without undue toxicity, irritation, allergic response, and the like, commensurate with a reasonable benefit/risk ratio, and effective for their intended use, as well as the zwitterionic forms, where possible, of the compounds described herein. The term salts refers to the relatively non-toxic, inorganic and organic acid addition salts of the compounds described herein. These salts can be prepared in situ during the isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobionate, methane sulphonate, and laurylsulphonate salts, and the like. These can include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like. (See S. M. Barge et al., *J. Pharm. Sci.* (1977) 66, 1, which is incorporated herein by reference in its entirety, at least, for compositions taught herein.) Administration of the compounds and compositions described herein or pharmaceutically acceptable salts thereof to a subject can be carried out using therapeutically effective amounts of the compounds and compositions described herein or pharmaceutically acceptable salts thereof as described herein for periods of time effective to treat a disorder.

The effective amount of the compounds and compositions described herein or pharmaceutically acceptable salts thereof as described herein can be determined by one of ordinary skill in the art and includes exemplary dosage amounts for a mammal of from about 0.5 to about 200 mg/kg of body weight of active compound per day, which can be administered in a single dose or in the form of individual divided doses, such as from 1 to 4 times per day. Alternatively, the dosage amount can be from about 0.5 to about 150 mg/kg of body weight of active compound per day, about 0.5 to 100 mg/kg of body weight of active compound per day, about 0.5 to about 75 mg/kg of body weight of active compound per day, about 0.5 to about 50 mg/kg of body weight of active compound per day, about 0.5 to about 25 mg/kg of body weight of active compound per day, about 1 to about 20 mg/kg of body weight of active compound per day, about 1 to about 10 mg/kg of body weight of active compound per day, about 20 mg/kg of body weight of active compound per day, about 10 mg/kg of body weight of active compound per day, or about mg/kg of body weight of active compound per day. The expression effective amount, when used to describe an amount of compound in a method, refers to the amount of a compound that achieves the desired pharmacological effect or other effect, for example an amount that results in enzyme inhibition.

Those of skill in the art will understand that the specific dose level and frequency of dosage for any particular subject can be varied and will depend upon a variety of factors, including the activity of the specific compound employed, the metabolic stability and length of action of that compound, the species, age, body weight, general health, sex and diet of the subject, the mode and time of administration, rate of excretion, drug combination, and severity of the particular condition.

Methods of Making the Compounds

The compounds described herein can be prepared in a variety of ways known to one skilled in the art of organic synthesis or variations thereon as appreciated by those skilled in the art. The compounds described herein can be prepared from readily available starting materials.

Optimum reaction conditions can vary with the particular reactants or solvents used, but such conditions can be determined by one skilled in the art.

Variations on the compounds discussed herein include the addition, subtraction, or movement of the various constituents as described for each compound. Similarly, when one or more chiral centers are present in a molecule, the chirality of the molecule can be changed. Additionally, compound synthesis can involve the protection and deprotection of various chemical groups. The use of protection and deprotection, and the selection of appropriate protecting groups can be determined by one skilled in the art. The chemistry of protecting groups can be found, for example, in Wuts and Greene, Protective Groups in Organic Synthesis, 4th Ed., Wiley & Sons, 2006, which is incorporated herein by reference in its entirety.

The starting materials and reagents used in preparing the disclosed compounds and compositions are either available from commercial suppliers such as Aldrich Chemical Co., (Milwaukee, Wis.), Acros Organics (Morris Plains, N.J.), Fisher Scientific (Pittsburgh, Pa.), Sigma (St. Louis, Mo.), Pfizer (New York, N.Y.), GlaxoSmithKline (Raleigh, N.C.), Merck (Whitehouse Station, N.J.), Johnson & Johnson (New Brunswick, N.J.), Aventis (Bridgewater, N.J.), AstraZeneca (Wilmington, Del.), Novartis (Basel, Switzerland), Wyeth (Madison, N.J.), Bristol-Myers-Squibb (New York, N.Y.), Roche (Basel, Switzerland), Lilly (Indianapolis, Ind.), Abbott (Abbott Park, Ill.), Schering Plough (Kenilworth, N.J.), or Boehringer Ingelheim (Ingelheim, Germany), or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991); March's Advanced Organic Chemistry, (John Wiley and Sons, 4th Edition); and Larock's Comprehensive Organic Transformations (VCH Publishers Inc., 1989). Other materials, such as the pharmaceutical carriers disclosed herein can be obtained from commercial sources.

Reactions to produce the compounds described herein can be carried out in solvents, which can be selected by one of skill in the art of organic synthesis. Solvents can be substantially nonreactive with the starting materials (reactants), the intermediates, or products under the conditions at which the reactions are carried out, i.e., temperature and pressure. Reactions can be carried out in one solvent or a mixture of more than one solvent. Product or intermediate formation can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), or mass spectrometry, or by chromatography such as high performance liquid chromatography (HPLC) or thin layer chromatography.

Activity Assays

The activity of the compounds provided herein as anticancer and immunostimulatory agents can be measured in standard assays. The activities of the compounds as determined using the assays described herein can be reported in terms of $IC_{50}$. As used herein, $IC_{50}$ refers to an amount, concentration, or dosage of a particular test compound that achieves a 50% inhibition of a maximal response in an assay that measures such response.

In certain aspects, the disclosed compounds and compositions need not actually be synthesized, but instead can be used as targets for any molecular modeling technique to predict and characterize interactions with cancer associated enzymes. This is achieved through structural information and computer modeling. Computer modeling technology allows visualization of the three-dimensional atomic structure of a selected molecule and the rational design of new compounds that will interact with an enzyme. The three-dimensional construct of the enzyme typically depends on data from x-ray crystallographic analyses or NMR imaging of the selected molecule. The molecular dynamics require force field data (e.g., Merck Molecular Force Field). The computer graphics systems enable prediction of how a new compound will link to the enzyme and allow experimental manipulation of the structures of the compound to perfect binding specificity. Prediction of what the interactions will be when small changes are made in one or both requires molecular mechanics software and computationally intensive computers, usually coupled with user-friendly, menu-driven interfaces between the molecular design program and the user.

Examples of molecular modeling systems are the CHARMm and QUANTA programs, Polygen Corporation, Waltham, Mass. CHARMm performs the energy minimization and molecular dynamics functions. QUANTA performs the construction, graphic modeling and analysis of molecular structure. QUANTA allows interactive construction, modification, visualization, and analysis of the behavior of molecules with each other. Upon identification of compounds that interact in a desired way with the enzyme in silico, actual compounds can be synthesized and assayed as disclosed herein.

Kits

Also provided herein are kits for treating or preventing cancer in a subject. A kit can include any of the compounds or compositions described herein. A kit can further include one or more anti-cancer agents (e.g., paclitaxel). A kit can include an oral formulation of any of the compounds or compositions described herein. A kit can additionally include directions for use of the kit (e.g., instructions for treating a subject).

The examples below are intended to further illustrate certain aspects of the methods and compounds described herein, and are not intended to limit the scope of the claims.

Methods of Use

Provided herein are methods of treating, preventing, or ameliorating cancer in a subject. Also provided are methods of stimulating the immune system of a subject. These methods include administering to a subject an effective amount of one or more of the compounds or compositions described herein, or a pharmaceutically acceptable salt or prodrug thereof. The compounds and compositions described herein or pharmaceutically acceptable salts thereof are useful for treating cancer in humans, e.g., pediatric and geriatric populations, and in animals, e.g., veterinary applications. They can also be useful as immunostimulants. The disclosed methods can optionally include identifying a patient who is or can be in need of treatment of a cancer. Examples of cancer types treatable by the compounds and compositions described herein include bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells). Some examples of cancers contemplated for treatment include carcinomas, Karposi's sarcoma, melanoma, mesothelioma, soft tissue sarcoma, pancreatic cancer, colon cancer, lung cancer, leukemia (acute lymphoblastic, acute myeloid, chronic lymphocytic, chronic myeloid, and other), and lymphoma (Burkitt's, follicular, Hodgkin's, non-Hodgkin's, mantle cell, and other), and multiple myeloma.

The methods of treatment or prevention described herein can further include treatment with one or more additional agents (e.g., an anticancer agent or ionizing radiation). The one or more additional agents and the compounds and compositions or pharmaceutically acceptable salts thereof as described herein can be administered in any order, including simultaneous administration, as well as temporally spaced order of up to several days apart. The methods can also include more than a single administration of the one or more additional agents and/or the compounds and compositions or pharmaceutically acceptable salts thereof as described herein. The administration of the one or more additional agents and the compounds and compositions or pharmaceutically acceptable salts thereof as described herein can be by the same or different routes. When treating with one or more additional agents, the compounds and compositions or pharmaceutically acceptable salts thereof as described herein can be combined into a pharmaceutical composition that includes the one or more additional agents.

For example, the compounds or compositions or pharmaceutically acceptable salts or prodrugs thereof as described herein can be combined into a pharmaceutical composition with an additional anti-cancer agent, such as 13-cis-Retinoic Acid, 2-Amino-6-Mercaptopurine, 2-CdA, 2-Chlorodeoxyadenosine, 5-Fluorouracil, 6-Thioguanine, 6-Mercaptopurine, Accutane, Actinomycin-D, Adriamycin, Adrucil, Agrylin, Ala-Cort, Aldesleukin, Alemtuzumab, Alitretinoin, Alkaban-AQ, Alkeran, All-trans-retinoic acid, Alpha-interferon, Altretamine, Amethopterin, Amifostine, Aminoglutethimide, Anagrelide, Anandron, Anastrozole, Arabinosylcytosine, Aranesp, Aredia, Arimidex, Aromasin, Arsenic trioxide, Asparaginase, ATRA, Avastin, BCG, BCNU, Bevacizumab, Bexarotene, Bicalutamide, BiCNU, Blenoxane, Bleomycin, Bortezomib, Busulfan, Busulfex, C225, Calcium Leucovorin, Campath, Camptosar, Camptothecin-11, Capecitabine, Carac, Carboplatin, Carmustine, Carmustine wafer, Casodex, CCNU, CDDP, CeeNU, Cerubidine, Cetuximab, Chlorambucil, Cisplatin, Citrovorum Factor, Cladribine, Cortisone, Cosmegen, CPT-11, Cyclophosphamide, Cytadren, Cytarabine, Cytarabine liposomal, Cytosar-U, Cytoxan, Dacarbazine, Dactinomycin, Darbepoetin alfa, Daunomycin, Daunorubicin, Daunorubicin hydrochloride, Daunorubicin liposomal, DaunoXome, Decadron, Delta-Cortef, Deltasone, Denileukin diftitox, DepoCyt, Dexamethasone, Dexamethasone acetate, Dexamethasone sodium phosphate, Dexasone, Dexrazoxane, DHAD, DIC, Diodex, Docetaxel, Doxil, Doxorubicin, Doxorubicin liposomal, Droxia, DTIC, DTIC-Dome, Duralone, Efudex, Eligard, Ellence, Eloxatin, Elspar, Emcyt, Epirubicin, Epoetin alfa, Erbitux, *Erwinia* L-asparaginase, Estramustine, Ethyol, Etopophos, Etoposide, Etoposide phosphate, Eulexin, Evista, Exemestane, Fareston, Faslodex, Femara, Filgrastim, Floxuridine, Fludara, Fludarabine, Fluoroplex, Fluorouracil, Fluorouracil (cream), Fluoxymesterone, Flutamide, Folinic Acid, FUDR, Fulvestrant, G-CSF, Gefitinib, Gemcitabine, Gemtuzumab ozogamicin, Gemzar, Gleevec, Lupron, Lupron Depot, Matulane, Maxidex, Mechlorethamine, Mechlorethamine Hydrochlorine, Medralone, Medrol, Megace, Megestrol, Megestrol Acetate, Melphalan, Mercaptopurine, Mesna, Mesnex, Methotrexate, Methotrexate Sodium, Methylprednisolone, Mylocel, Letrozole, Neosar, Neulasta, Neumega, Neupogen, Nilandron, Nilutamide, Nitrogen Mustard, Novaldex, Novantrone, Octreotide, Octreotide acetate, Oncospar, Oncovin, Ontak, Onxal, Oprevelkin, Orapred, Orasone, Oxaliplatin, Paclitaxel, Pamidronate, Panretin, Paraplatin, Pediapred, PEG Interferon, Pegaspargase, Pegfilgrastim, PEG-INTRON, PEG-L-asparaginase, Phenylalanine Mustard, Platinol, Platinol-AQ, Prednisolone, Prednisone, Prelone, Procarbazine, PROCRIT, Proleukin, Prolifeprospan 20 with Carmustine implant, Purinethol, Raloxifene, Rheumatrex, Rituxan, Rituximab, Roveron-A (interferon alfa-2a), Rubex, Rubidomycin hydrochloride, Sandostatin, Sandostatin LAR, Sargramostim, Solu-Cortef, Solu-Medrol, STI-571, Streptozocin, Tamoxifen, Targretin, Taxol, Taxotere, Temodar, Temozolomide, Teniposide, TESPA, Thalidomide, Thalomid, TheraCys, Thioguanine, Thioguanine Tabloid, Thiophosphoamide, Thioplex, Thiotepa, TICE, Toposar, Topotecan, Toremifene, Trastuzumab, Tretinoin, Trexall, Trisenox, TSPA, VCR, Velban, Velcade, VePesid, Vesanoid, Viadur, Vinblastine, Vinblastine Sulfate, Vincasar Pfs, Vincristine, Vinorelbine, Vinorelbine tartrate, VLB, VP-16, Vumon, Xeloda, Zanosar, Zevalin, Zinecard, Zoladex, Zoledronic acid, Zometa, Gliadel wafer, Glivec, GM-CSF, Goserelin, granulocyte colony stimulating factor, Halotestin, Herceptin, Hexadrol, Hexalen, Hexamethylmelamine, HMM, Hycamtin, Hydrea, Hydrocort Acetate, Hydrocortisone, Hydrocortisone sodium phosphate, Hydrocortisone sodium succinate, Hydrocortone phosphate, Hydroxyurea, Ibritumomab, Ibritumomab Tiuxetan, Idamycin, Idarubicin, Ifex, IFN-alpha, Ifosfamide, IL 2, IL-11, Imatinib mesylate, Imidazole Carboxamide, Interferon alfa, Interferon Alfa-2b (PEG conjugate), Interleukin 2, Interleukin-11, Intron A (Interferon alfa-2b), Leucovorin, Leukeran, Leukine, Leuprolide, Leurocristine, Leustatin, Liposomal Ara-C, Liquid Pred, Lomustine, L-PAM, L-Sarcolysin, Meticorten, Mitomycin, Mitomycin-C, Mitoxantrone, M-Prednisol, MTC, MTX, Mustargen, Mustine, Mutamycin, Myleran, Iressa, Irinotecan, Isotretinoin, Kidrolase, Lanacort, L-Asparaginase, and LCR. The additional anti-cancer agent can also include biopharmaceuticals such as, for example, antibodies.

Many tumors and cancers have viral genome present in the tumor or cancer cells. For example, Epstein-Barr Virus (EBV) is associated with a number of mammalian malignancies. The compounds disclosed herein can also be used alone or in combination with anticancer or antiviral agents, such as ganciclovir, azidothymidine (AZT), lamivudine (3TC), etc., to treat patients infected with a virus that can cause cellular transformation and/or to treat patients having a tumor or cancer that is associated with the presence of viral genome in the cells. The compounds disclosed herein can also be used in combination with viral based treatments of oncologic disease.

Also described herein are methods of killing a tumor cell in a subject. The method includes contacting the tumor cell with an effective amount of a compound or composition as described herein, and optionally includes the step of irradiating the tumor cell with an effective amount of ionizing radiation. Additionally, methods of radiotherapy of tumors are provided herein. The methods include contacting the tumor cell with an effective amount of a compound or composition as described herein, and irradiating the tumor with an effective amount of ionizing radiation. As used herein, the term ionizing radiation refers to radiation comprising particles or photons that have sufficient energy or can produce sufficient energy via nuclear interactions to produce ionization. An example of ionizing radiation is X-radiation. An effective amount of ionizing radiation refers to a dose of ionizing radiation that produces an increase in cell damage or death when administered in combination with the compounds described herein. The ionizing radiation can be delivered according to methods as known in the art, including administering radiolabeled antibodies and radioisotopes.

The methods and compounds as described herein are useful for both prophylactic and therapeutic treatment. As used herein the term treating or treatment includes prevention; delay in onset; diminution, eradication, or delay in exacerbation of signs or symptoms after onset; and prevention of relapse. For prophylactic use, a therapeutically effective amount of the compounds and compositions or pharmaceutically acceptable salts thereof as described herein are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms of an infection. Prophylactic administration can be used, for example, in the chemopreventative treatment of subjects presenting precancerous lesions, those diagnosed with early stage malignancies, and for subgroups with susceptibilities (e.g., family, racial, and/or occupational) to particular cancers. Therapeutic treatment involves administering to a subject a therapeutically effective amount of the compounds and compositions or pharmaceutically acceptable salts thereof as described herein after cancer is diagnosed.

In some examples, the compounds disclosed herein are not topoisomerase II inhibitors. In some examples, the compounds disclosed herein can activate caspase-3.

EXAMPLES

The following examples are set forth below to illustrate the methods and results according to the disclosed subject matter. These examples are not intended to be inclusive of all aspects of the subject matter disclosed herein, but rather to illustrate representative methods, compositions, and results. These examples are not intended to exclude equivalents and variations of the present invention, which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, temperatures, pressures, and other reaction ranges and conditions that can be used to optimize the product purity and yield obtained from the described process. Only reasonable and routine experimentation will be required to optimize such process conditions.

The melting point was measured using a Fisher Scientific apparatus and is uncorrected. Specific rotation values were obtained on a Perkin-Elmer model 343 polarimeter. UV spectra were recorded on a Hitachi U2910 UV spectrophotometer. ECD measurements were performed using a JASCO J-810 spectropolarimeter. IR spectra were recorded on a Nicolet 6700 FT-IR spectrometer. $^1$H and $^{13}$C, DEPT, HSQC, HMBC, NOESY, and COSY NMR spectra were recorded at room temperature on Bruker Avance DRX-400, DRX-600, or DRX-800 MHz NMR spectrometers. ESIMS and HRESIMS were measured on a LCT-TOF or a Q-TOF mass spectrometer in the positive-ion mode. Column chromatography was conducted using silica gel (65×250 or 230×400 mesh, Sorbent Technologies, Atlanta, Ga.). Analytical thin-layer chromatography (TLC) was performed on precoated silica gel 60 F254 plates (Sorbent Technologies, Atlanta, Ga.). Sephadex LH-20 was purchased from Amersham Biosciences, Uppsala, Sweden. For visualization of TLC plates, sulfuric acid reagent was used. Fluorescence was tested using a Spectroline (model ENF-260C) UV light source. All procedures were carried out using anhydrous solvents purchased from commercial sources and employed without further purification. Reagents for chemical synthesis were purchased from Sigma except where indicated, and reactions were monitored by TLC using precoated silica gel plates. Crystallographic data were collected through the Service Crystallography at Advanced Light Source (SCrALS) program at the Small-Crystal Crystallography Beamline 11.3.1 at the Advanced Light Source (ALS), Lawrence Berkeley National Laboratory, with Bruker APEXII CCD detector (Bruker Analytical X-ray Instruments, Inc., Madison, Wis.).

Example 1

Phyllanthusmin Compounds:

A series of phyllanthusmin compounds (FIGS. 1 and 2) were synthesized and analyzed for their in vitro activity. The majority of these analogues showed highly potent activity against HT-29 cells (see Table 1) and ovarian cancer cells (data not shown). The compounds PHY-25 and PHY-31 displayed IC$_{50}$ values of less than 20 nM against HT-29 cells.

Synthetic Schemes.

The synthetic schemes of the phyllanthusmin compounds are described in Scheme 1.

Scheme 1: Synthetic schemes for phyllanthusmin compounds.

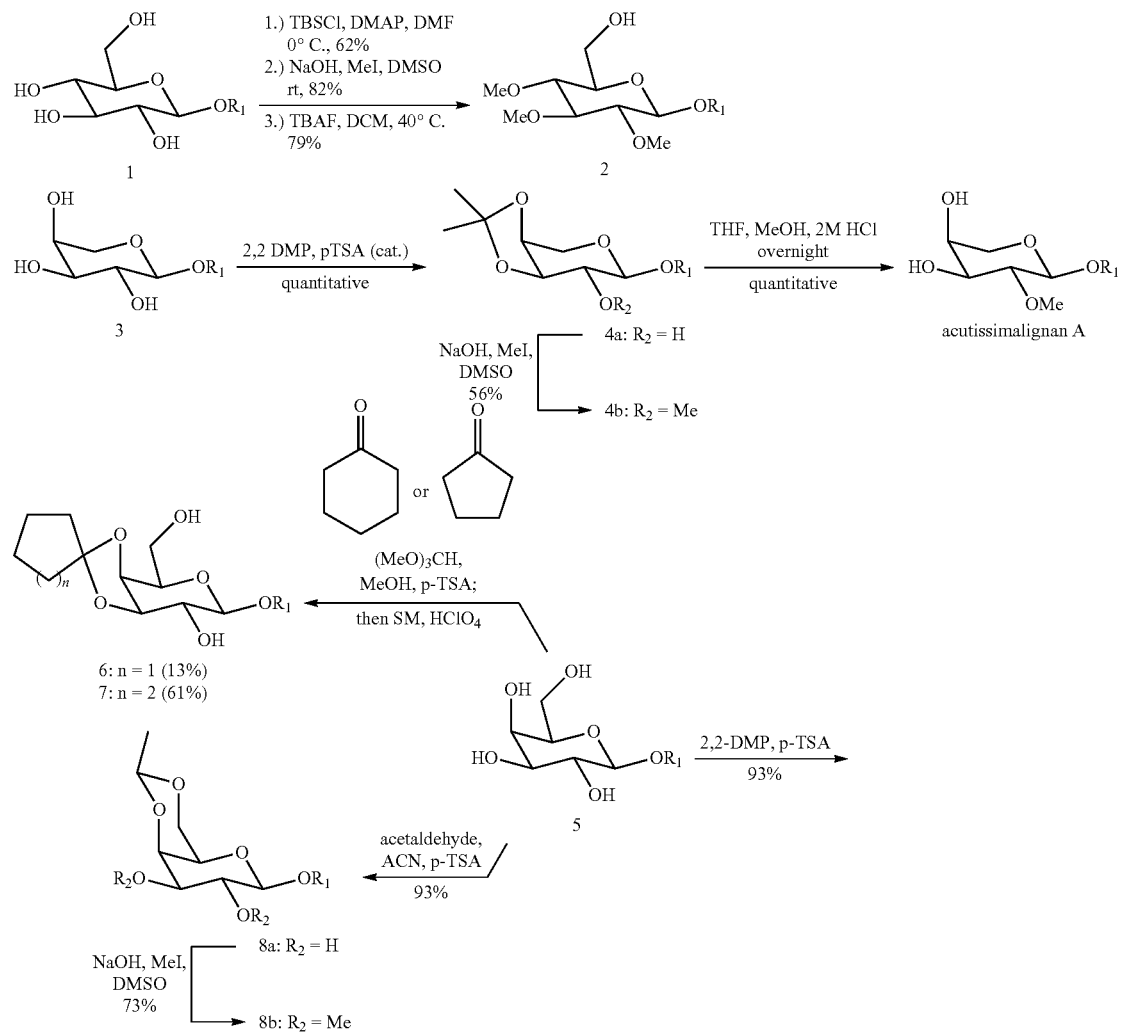

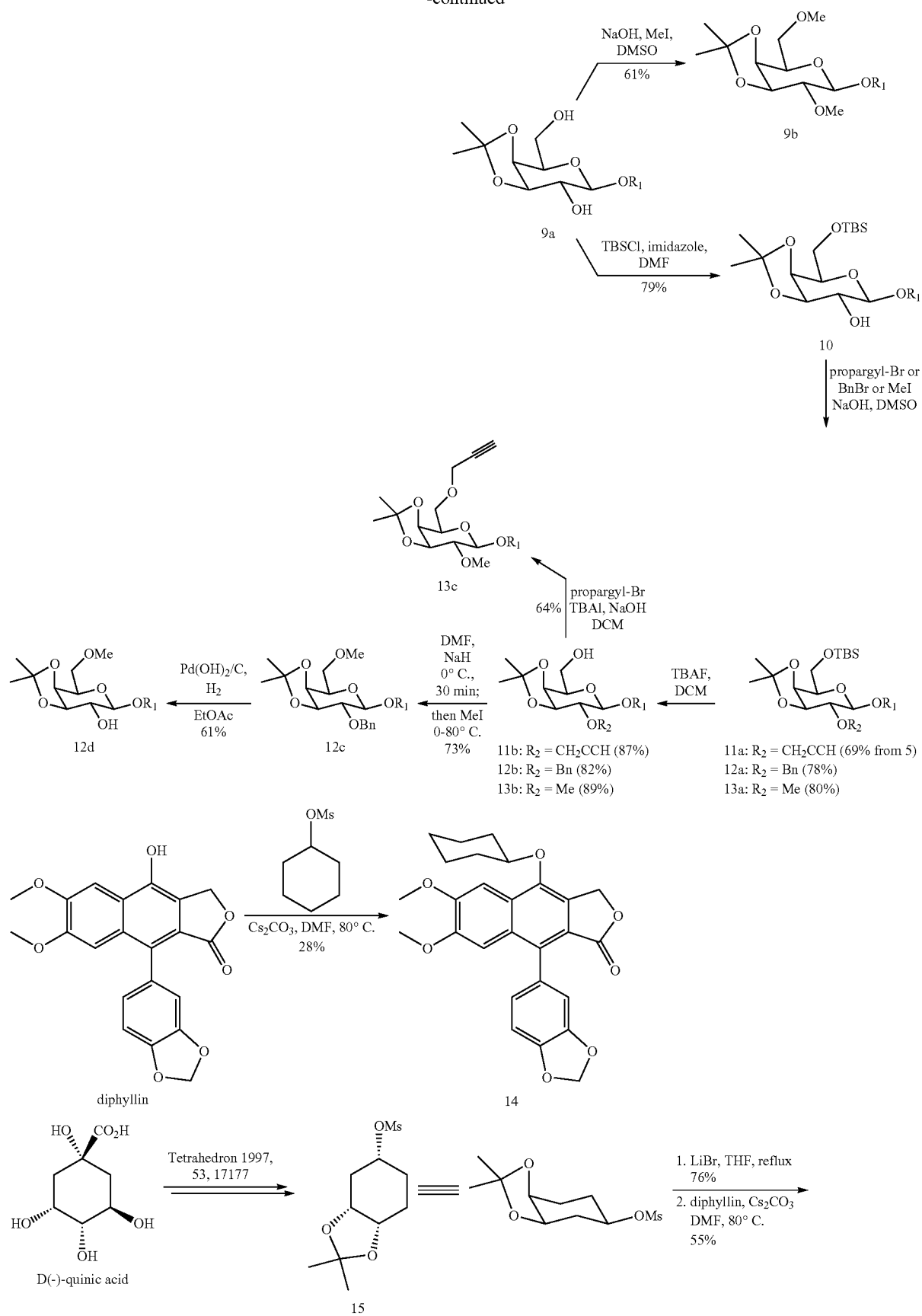

EXPERIMENTALS

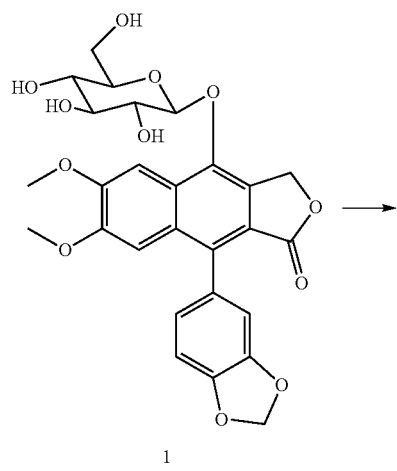

1

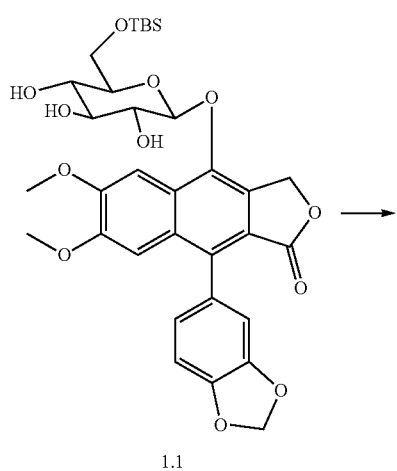

1.1

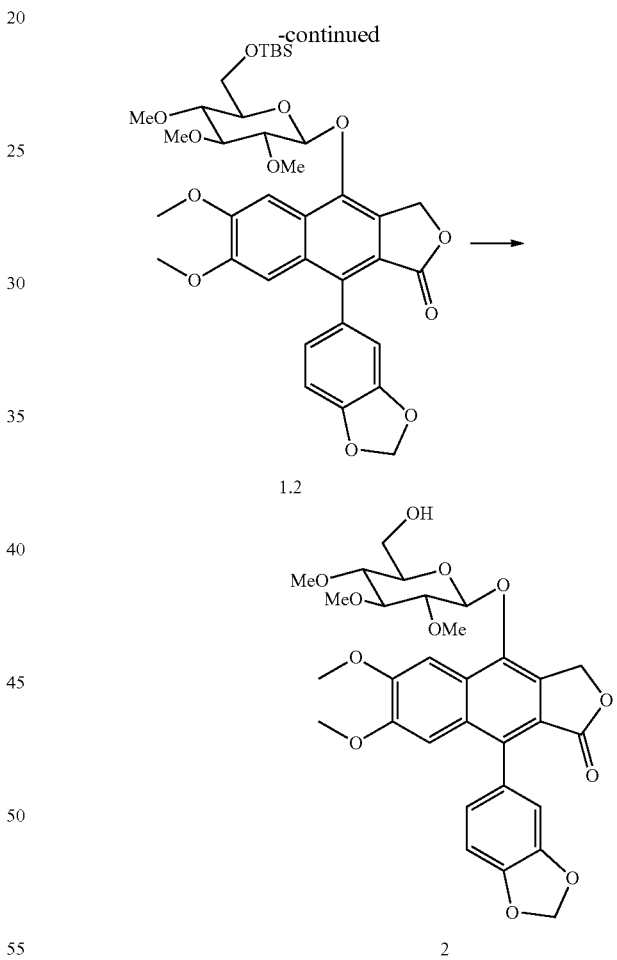

Synthesis of 2 (PHY-25).

To a solution of (β-D-glucopyranosyl diphyllin (1; 0.300 g, 0.553 mmol) in dimethylformamide (5.5 mL) held at −10 to −12° C. was added imidazole (0.188 g, 2.77 mmol) and tert-butyldimethylsilyl chloride (0.333 g, 2.21 mmol). The reaction was allowed to stir at this temperature for 20 minutes before being quenched with the addition of water, followed by extraction with ethyl acetate. The combined organic layers were washed with brine, dried over sodium sulfate, and then concentrated in vacuo. Filtration through a

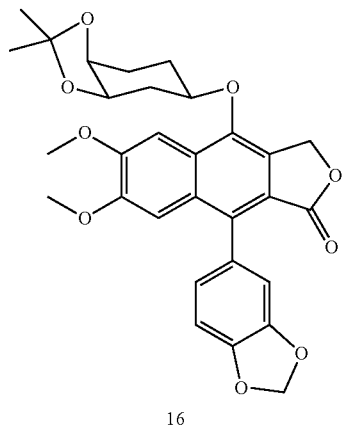

bed of silica with ethyl acetate then afforded 1.1 (0.225 g, 62%) as a white solid: IR $\nu_{max}$ (KBr, cm$^{-1}$): 3429, 3084, 3006, 2953, 2929, 2884, 2857, 1740, 1623, 1597; $^1$H NMR (400 MHz, CDCl$_3$) δ 7.94 (s, 1H), 7.09 (s, 1H), 6.96 (d, J=7.3 Hz, 1H), 6.85-6.79 (m, 2H), 6.08 (d, J=17.8 Hz, 2H), 5.49 (d, J=14.9 Hz, 1H), 5.40 (d, J=15.1 Hz, 1H), 4.88 (d, J=7.9 Hz, 1H), 4.05 (s, 3H), 3.93-3.82 (m, 3H), 3.81 (s, 3H), 3.73-3.61 (m, 2H), 3.45 (s, 1H), 3.35 (s, 1H), 2.99 (s, 1H), 2.85 (s, 1H), 0.87 (s, 9H), 0.10 (s, 3H), 0.08 (s, 3H); $^{13}$C NMR (75 MHz, CDCl$_3$) δ 170.28, 152.16, 150.38, 147.69, 147.66, 144.37, 136.77, 131.29, 130.82, 128.36, 127.27, 123.72, 119.14, 110.83, 108.31, 106.31, 104.64, 101.39, 101.07, 74.65, 73.82, 72.89, 67.63, 64.58, 56.43, 55.96, 25.84, 18.22, −5.43, −5.47; HRMS-ESI calcd for C$_{33}$H$_{40}$O$_{12}$Si (M+Na)$^+$ 679.21812, found 679.21732; mp 146-148° C.

To a solution of 1.1 (0.513 g, 0.781 mmol) in dimethyl sulfoxide (15.6 mL) was sequentially added crushed sodium hydroxide pellets (0.625 g, 15.62 mmol) and iodomethane (2.92 mL, 46.86 mmol) at rt. The resulting mixture was shaken for 4 hr prior to dilution with ethyl acetate and H$_2$O. Following extraction with ethyl acetate, the combined organics were washed with several portions of H$_2$O, brine, and then dried over sodium sulfate prior to concentration en vacuo. Flash column chromatography (silica gel, 10% EtOAc, 5% EtOH in Hex) afforded 1.2 (0.446 g, 82%) as a white solid: IR $\nu_{max}$ (KBr, cm$^{-1}$): 3083, 2953, 2931, 2857, 2835, 1764, 1622, 1596, 1507; $^1$H NMR (400 MHz, CDCl$_3$) δ 7.86 (s, 1H), 7.09 (s, 1H), 6.96 (d, J=8.2 Hz, 1H), 6.85-6.78 (m, 2H), 6.07 (d, J=19.0 Hz, 2H), 5.63 (dd, J=14.8, 2.6 Hz, 1H), 5.41 (d, J=15.2 Hz, 1H), 4.76 (d, J=7.8 Hz, 1H), 4.08 (s, 3H), 3.85 (s, 3H), 3.81 (s, 3H), 3.77 (s, 2H), 3.71 (s, 3H), 3.56 (s, 3H), 3.40 (t, J=8.1 Hz, 1H), 3.28 (dq, J=17.7, 8.9 Hz, 2H), 3.10 (d, J=9.4 Hz, 1H), 0.87 (s, 9H), 0.05 (s, 6H); $^{13}$C NMR (101 MHz, CDCl$_3$) δ 170.07, 152.03, 150.23, 147.61, 144.42, 136.49, 131.81, 131.77, 130.89, 128.56, 128.52, 127.20, 123.74, 123.71, 119.49, 110.86, 110.81, 108.35, 106.37, 104.73, 101.36, 100.69, 87.04, 84.22, 79.13, 76.18, 67.71, 61.92, 61.38, 61.10, 60.64, 56.27, 55.99, 25.87, 18.30, −5.34, −5.40; HRMS-ESI calcd for C$_{36}$H$_{46}$O$_{12}$Si (M+Na)$^+$ 721.26507, found 721.26548; mp 99-101° C.

To a solution of 1.2 (0.446 g, 0.638 mmol) in dichloromethane (6.4 mL) was added tetrabutylammonium fluoride (1M in THF, 1.6 mL). The reaction was allowed to stir overnight at 40° C. The reaction was quenched with water and extracted with dichloromethane. The combined organic layers were washed with brine, dried over sodium sulfate, and then concentrated in vacuo. Flash column chromatography (silica gel; 10% EtOH, 3% EtOAc in Hex) afforded 2 (0.293 g, 79%) as a white solid: $[\alpha]_D^{20}$+9° (c 2.7, CHCl$_3$); IR $\nu_{max}$ (KBr, cm$^{-1}$): 3525, 3091, 2938, 2835, 1765, 1624, 1595, 1507; $^1$H NMR (400 MHz, CDCl$_3$) δ 7.85 (s, 1H), 7.09 (s, 1H), 6.96 (d, J=7.9 Hz, 1H), 6.87-6.78 (m, 2H), 6.08 (dd, J=17.9, 1.3 Hz, 2H), 5.52-5.42 (m, 2H), 4.82 (d, J=7.9 Hz, 1H), 4.08 (s, 3H), 3.84 (s, 3H), 3.81 (s, 3H), 3.79-3.73 (m, 1H), 3.71 (s, 3H), 3.59 (s, 3H), 3.41 (t, J=8.2 Hz, 1H), 3.36-3.25 (m, 2H), 3.18 (d, J=9.3 Hz, 1H), 1.69 (s, 1H); $^{13}$C NMR (101 MHz, CDCl$_3$) δ 169.86, 152.09, 150.32, 147.68, 147.65, 144.59, 136.78, 131.03, 130.91, 128.38, 127.27, 123.73, 123.70, 119.35, 110.81, 110.79, 108.35, 106.38, 104.85, 101.39, 100.73, 86.78, 84.13, 79.34, 75.49, 67.32, 62.00, 61.48, 61.13, 60.78, 56.28, 56.00; HRMS-ESI calcd for C$_{30}$H$_{32}$O$_{12}$ (M+Na)$^+$ 607.17860, found 607.17991; mp 189-191° C.

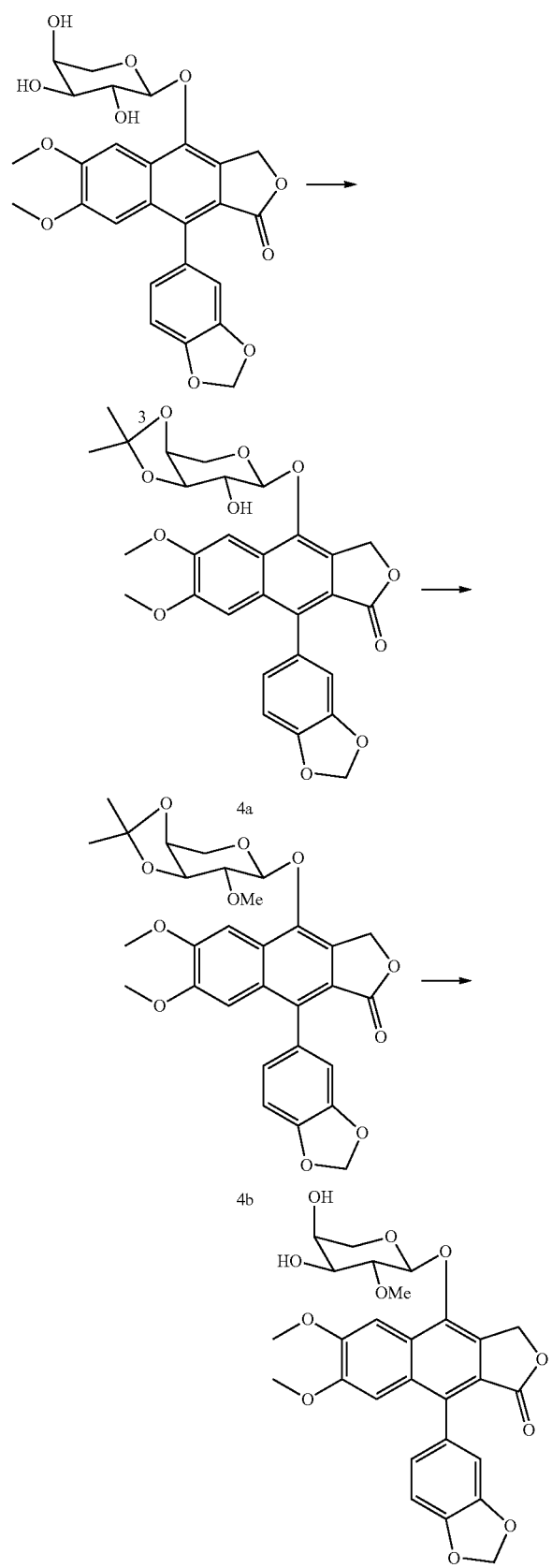

acutissimalignan A

Synthesis of 4a (PHY-30).

To α-L-arabinopyranosyl diphyllin (0.128 g, 0.250 mmol) in 2,2-dimethoxy propane (1.25 mL) was added a catalytic amount of p-toluene sulfonic acid. The resulting mixture was stirred at room temperature overnight. The reaction was quenched with aqueous sodium bicarbonate (sat.) and extracted with dichloromethane. The combined organic layers were washed with brine and then dried over sodium sulfate prior to being concentrated in vacuo to afford 4a (0.141 g, quantitative) as a white solid: $[\alpha]_D^{20}$ −32° (c 0.9, CHCl$_3$); IR $v_{max}$ (KBr, cm$^{-1}$): 3466, 3084, 2986, 2937, 2895, 2834, 1758, 1622, 1597, 1507; $^1$H NMR (400 MHz, CDCl$_3$) δ 7.88 (s, 1H), 7.08 (d, J=1.5 Hz, 1H), 6.95 (d, J=7.8 Hz, 1H), 6.85-6.78 (m, 2H), 6.11-6.03 (m, 2H), 5.52 (dd, J=15.0, 2.8 Hz, 1H), 5.43 (dd, J=15.1, 1.2 Hz, 1H), 4.85 (d, J=7.2 Hz, 1H), 4.37 (dd, J=9.8, 4.2 Hz, 1H), 4.25 (dd, J=12.8, 4.0 Hz, 1H), 4.19-4.10 (m, 2H), 4.04 (s, 3H), 3.89 (dd, J=12.9, 4.1 Hz, 1H), 3.80 (s, 3H), 2.89 (s, 1H), 1.63 (s, 3H), 1.42 (s, 3H); $^{13}$C NMR (75 MHz, CDCl$_3$) δ 169.94, 152.14, 150.37, 147.66, 144.43, 136.65, 131.14, 130.95, 128.45, 127.25, 123.74, 119.36, 111.06, 110.84, 108.32, 106.46, 104.40, 101.38, 100.92, 78.54, 74.25, 72.83, 67.38, 63.49, 56.41, 55.98, 28.07, 25.96; HRMS-ESI calcd for C$_{29}$H$_{28}$O$_{11}$ (M+Na)$^+$ 575.15238, found 575.15188; mp 252-254° C.

Synthesis of 4b (PHY-31).

To a solution of 4a (0.116 g, 0.210 mmol) in dimethyl sulfoxide (4.2 mL) was added solid crushed sodium hydroxide pellets (0.168 g, 4.199 mmol) prior to the addition of iodomethane (0.784 mL, 12.6 mmol). The resulting mixture was then shaken overnight. Dimethyl sulfoxide was transferred away from the solid sodium hydroxide, which was then rinsed with several portions of dichloromethane. The combined organics were then washed with several portions of water, brine, and then dried over sodium sulfate prior to concentration in vacuo. The resulting crude material was purified by flash column chromatography (silica gel; 5% EtOAc, 7.5% EtOH in Hex) to afford 4b (67 mg, 56%) as a white solid: $[\alpha]_D^{20}$ −7° (c 2.5, CHCl$_3$); IR $v_{max}$ (KBr, cm$^{-1}$): 3083, 2935, 2833, 1760, 1622, 1596, 1507; $^1$H NMR (400 MHz, CDCl$_3$) δ 7.87 (s, 1H), 7.09 (s, 1H), 6.96 (d, J=7.9 Hz, 1H), 6.86-6.79 (m, 2H), 6.11-6.03 (m, 2H), 5.53 (dd, J=15.1, 2.4 Hz, 1H), 5.44 (dd, J=15.1, 1.6 Hz, 1H), 4.81 (d, J=7.5 Hz, 1H), 4.30 (dd, J=6.7, 3.2 Hz, 1H), 4.24-4.18 (m, 2H), 4.07 (s, 3H), 3.81 (s, 3H), 3.80 (s, 3H), 3.78 (d, J=3.8 Hz, 1H), 3.70 (t, J=7.4 Hz, 1H), 1.65 (s, 3H), 1.41 (s, 3H); $^{13}$C NMR (75 MHz, CDCl$_3$) δ 169.90, 152.06, 150.29, 147.63, 144.55, 136.52, 131.17, 130.94, 128.48, 127.23, 123.74, 123.69, 119.39, 110.83, 110.54, 108.31, 106.41, 104.32, 101.35, 100.88, 82.87, 78.64, 72.91, 67.44, 63.41, 60.31, 56.23, 55.95, 27.96, 25.89; HRMS-ESI calcd for C$_{30}$H$_{30}$O$_{11}$ (M+Na)$^+$ 589.16803, found 589.16761; mp 123-125° C.

Synthesis of Acutissimalignan A.

A solution of 4b (0.039 g, 0.069 mmol) in tetrahydrofuran (0.345 mL), methanol (0.345 mL), and 2M HCl (0.276 mL) was allowed to stir at room temperature overnight. Water was added to the reaction mixture which was then extracted with ethyl acetate. The combined organic layers were washed with brine, dried over sodium sulfate, and concentrated in vacuo to afford pure acutissimalignan A (0.036 g, quantitative) as a pale yellow crystalline solid without further purification: $[c]^{20}$ +14° (c 1.8, CHCl$_3$) [reported: $[\alpha]_D^{24}$ +12.1 (c 0.54, CHCl$_3$) in JNP 2008, 71, 655]; $^1$H NMR (400 MHz, CDCl$_3$) δ 7.80 (s, 1H), 7.09 (s, 1H), 6.95 (d, J=8.2 Hz, 1H), 6.84-6.77 (m, 2H), 6.05 (dd, J=9.9, 8.8 Hz, 2H), 5.56 (dd, J=15.1, 2.5 Hz, 1H), 5.45 (dd, J=15.1, 1.9 Hz, 1H), 4.78 (d, J=7.0 Hz, 1H), 4.07 (s, 3H), 4.04 (d, J=13.1 Hz, 1H), 3.98 (s, 1H), 3.89 (s, 3H), 3.81 (s, 3H), 3.76-3.66 (m, 2H), 3.43 (d, J=12.9 Hz, 1H), 2.88 (d, J=4.4 Hz, 1H), 2.71 (d, J=3.2 Hz, 1H); $^{13}$C NMR (101 MHz, CDCl$_3$) δ 170.07, 152.12, 150.27, 147.65, 144.34, 136.63, 131.33, 131.30, 130.98, 128.39, 127.02, 123.74, 123.64, 119.37, 110.83, 110.74, 108.35, 108.32, 106.46, 105.37, 101.38, 100.55, 81.74, 73.13, 68.30, 67.69, 66.25, 61.86, 56.24, 55.98.

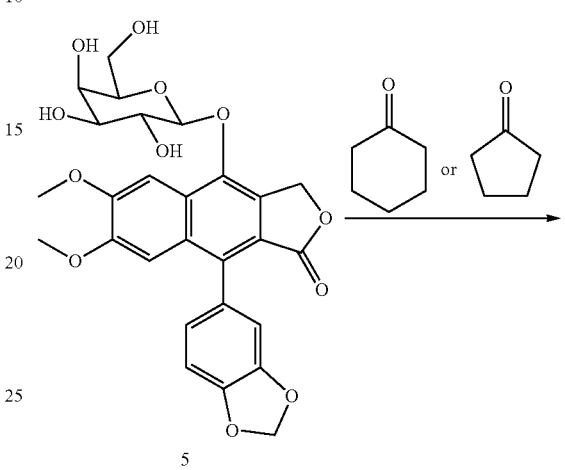

5

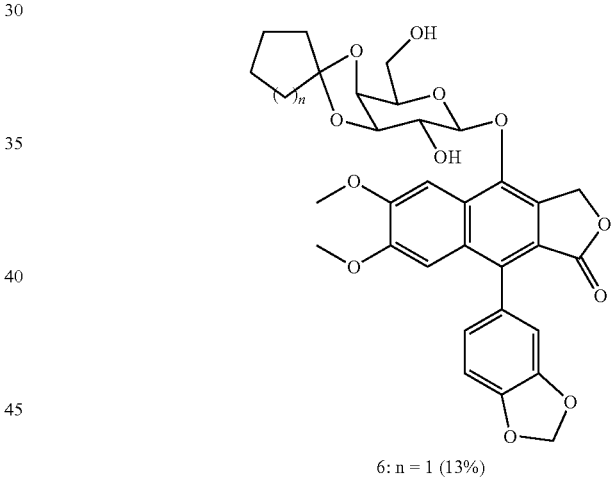

6: n = 1 (13%)
7: n = 2 (61%)

Synthesis of 6 (PHY-43).

A catalytic amount of p-toluenesulfonic acid was added to a solution of cyclopentanone (1.33 mL, 15 mmol), trimethyl orthoformate (0.121 mL, 1.105 mmol), and methanol (5 mL) contained within a reaction flask equipped with a short path distillation apparatus. The reaction was then stirred at 55° C. for 3 hours to remove the methyl formate formed as a byproduct. The temperature was then increased to 90° C. to remove methanol. After 45 minutes of stirring at 90° C., the reaction mixture was allowed to cool to room temperature whereupon β-D-galactopyranosyl-diphyllin (0.050 g, 0.092 mmol) was added followed by the addition of several drops of 70% perchloric acid. After stirring 4.5 hours at room temperature, aqueous sodium bicarbonate (sat.) was added. The reaction was extracted with ethyl acetate and the combined organics were washed with brine, dried over sodium sulfate and then concentrated in vacuo. Flash chromatography (deactivated silica gel; 20% EtOAc, 7.5% EtOH in Hex) afforded 6 (0.007 g, 13%) as a white solid, $[\alpha]_D^{20}$ −21° (c 0.1, CHCl$_3$); IR $\nu_{max}$ (KBr, cm$^{-1}$): 3413, 2937, 1749, 1622, 1595, 1507; $^1$H NMR (400 MHz, CDCl$_3$) δ 7.91 (s, 1H), 7.07 (d, J=1.5 Hz, 1H), 6.94 (dd, J=7.9, 2.6 Hz, 1H), 6.80 (dd, J=4.5, 1.5 Hz, 1H), 6.77 (dd, J=7.9, 1.6 Hz, 1H), 6.10-6.03 (m, 2H), 5.58 (dd, J=15.2, 2.2 Hz, 1H), 5.45 (dd, J=15.2, 1.2 Hz, 1H), 4.76 (d, J=8.3 Hz, 1H), 4.17 (dd, J=7.3, 5.4 Hz, 1H), 4.09 (dd, J=5.4, 2.1 Hz, 1H), 4.04 (s, 3H), 4.00 (d, J=7.8 Hz, 1H), 3.98-3.95 (m, 1H), 3.90 (dd, J=11.4, 4.6 Hz, 1H), 3.83-3.81 (m, 1H), 3.80 (s, 3H), 2.98 (s, 1H), 2.05 (t, J=7.2 Hz, 2H), 1.79-1.70 (m, 4H), 1.69-1.59 (m, 2H); $^{13}$C NMR (101 MHz, CDCl$_3$) δ 170.00, 152.15, 150.37, 147.67, 147.64, 144.56, 136.82, 131.18, 131.16, 130.92, 128.39, 128.38, 127.29, 123.74, 123.71, 120.64, 119.38, 110.82, 110.80, 108.32, 106.37, 104.46, 101.38, 100.97, 79.12, 74.60, 73.64, 73.62, 67.60, 62.55, 56.44, 55.98, 37.87, 37.82, 23.70, 23.55; HRMS-ESI calcd for C$_{32}$H$_{32}$O$_{12}$ (M+Na)$^+$ 631.17860, found 631.17680; mp 165-167° C.

Synthesis of 7 (PHY-42).

A catalytic amount of p-toluenesulfonic acid was added to a solution of cyclohexanone (1.55 mL, 15 mmol), trimethyl orthoformate (0.121 mL, 1.105 mmol), and methanol (5 mL) contained within a reaction flask equipped with a short path distillation apparatus. The reaction was then stirred at 55° C. for 3 hours to remove the methyl formate formed as a byproduct. The temperature was then increased to 90° C. to remove methanol. After 45 minutes of stirring at 90° C., the reaction mixture was allowed to cool to room temperature whereupon β-D-galactopyranosyl-diphyllin (0.050 g, 0.092 mmol) was added followed by the addition of several drops of 70% perchloric acid. After stirring overnight at room temperature water was added. After stirring for 15 minutes the reaction was extracted with ethyl acetate and the combined organics were washed with aqueous sodium bicarbonate (sat.), brine, and then dried over sodium sulfate. Following concentration in vacuo, the resulting crude solid was purified by flash chromatography (silica gel; 20% EtOAc, 7.5% EtOH in Hex) to afford 8 (0.035 g, 61%) as a white solid: $[\alpha]_D^{20}$ −12° (c 3.2, CHCl$_3$); IR $\nu_{max}$ (KBr, cm$^{-1}$): 3447, 2937, 2863, 1752, 1622, 1597, 1507; $^1$H NMR (400 MHz, CDCl$_3$) δ 7.92 (s, 1H), 7.07 (s, 1H), 6.94 (dd, J=7.9, 2.2 Hz, 1H), 6.79 (dd, J=12.7, 5.6 Hz, 2H), 6.11-6.03 (m, 2H), 5.59 (d, J=15.4 Hz, 1H), 5.45 (d, J=15.2 Hz, 1H), 4.74 (d, J=8.4 Hz, 1H), 4.26-4.17 (m, 2H), 4.04 (s, 3H), 4.01 (s, 1H), 3.97-3.82 (m, 3H), 3.80 (s, 3H), 2.96 (s, 1H), 2.09 (s, 1H), 1.91-1.80 (m, 2H), 1.80-1.64 (m, 4H), 1.60-1.52 (m, 2H), 1.51-1.38 (m, 2H); $^{13}$C NMR (75 MHz, CDCl$_3$) δ 170.20, 152.05, 150.30, 147.55, 147.51, 144.66, 136.57, 130.95, 130.93, 130.71, 128.32, 128.30, 127.30, 123.70, 123.64, 119.17, 119.13, 111.51, 110.77, 110.72, 108.18, 106.19, 104.53, 101.32, 101.12, 79.36, 74.29, 73.81, 67.73, 62.51, 56.39, 55.91, 38.04, 35.54, 25.02, 24.23, 23.83; HRMS-ESI calcd for C$_{33}$H$_{34}$O$_{12}$ (M+Na)$^+$ 645.19425, found 645.19563; mp 168-170° C.

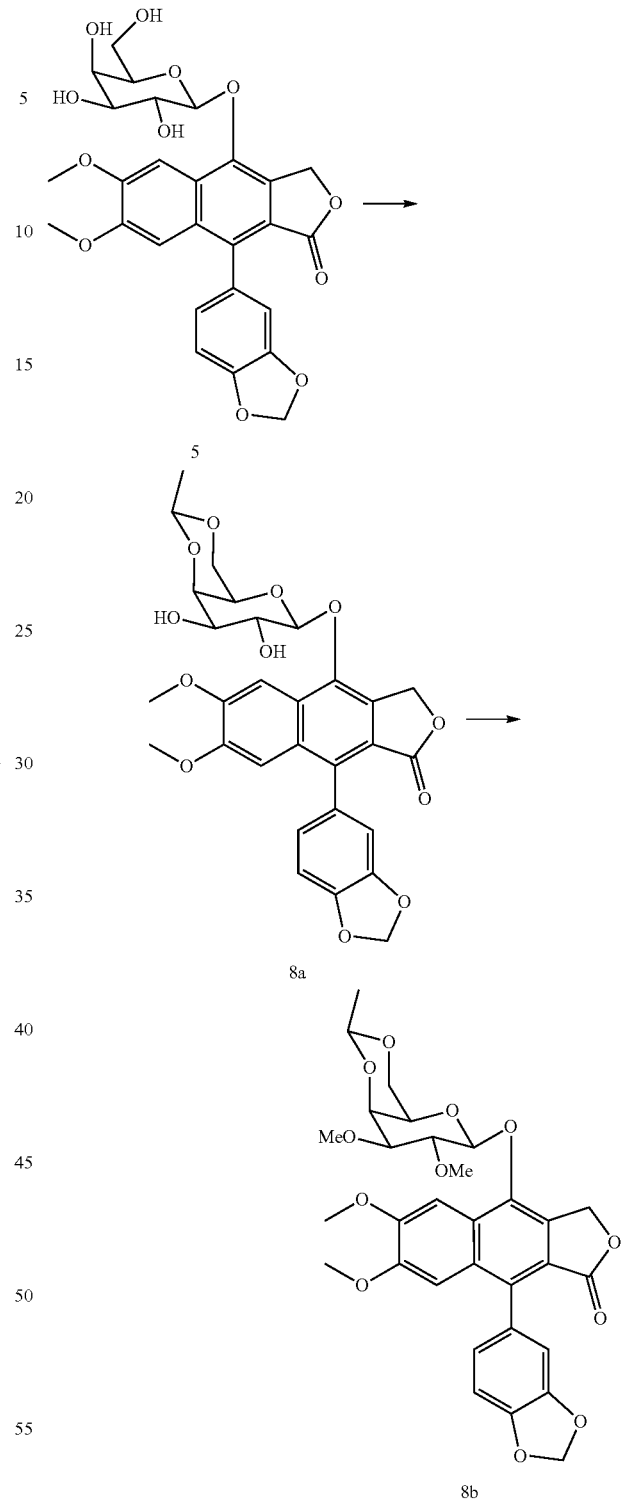

Synthesis of 8a (PHY-32).

To a solution of β-D-galactopyranosyl-diphyllin (0.100 g, 0.184 mmol), acetaldehyde (0.013 mL, 0.221 mmol), and acetonitrile (1 mL) was added p-toluenesulfonic acid until a pH of 3 was acquired. The reaction was allowed to stir at room temperate for 8 hours before being quenched with trimethylamine and concentrated under reduced pressure. The resulting crude material was purified by flash column chromatography (deactivated silica gel; 1→4% MeOH in DCM) to afford xx (97 mg, 93%) as a white solid: $[\alpha]_D^{20}$ −23° (c 1.8, CHCl$_3$); IR $\nu_{max}$ (KBr, cm$^{-1}$): 3469, 3086, 2992, 2968, 2940, 2883, 2835, 1756, 1624, 1597, 1507; $^1$H NMR (400 MHz, CDCl$_3$) δ 8.01 (s, 1H), 7.07 (s, 1H), 6.95 (dd, J=7.8, 3.2 Hz, 1H), 6.84-6.76 (m, 2H), 6.07 (dd, J=17.7, 1.3 Hz, 2H), 5.58 (dd, J=15.4, 1.6 Hz, 1H), 5.51 (dd, J=15.3, 1.1 Hz, 1H), 4.82 (d, J=7.8 Hz, 1H), 4.78 (q, J=5.0 Hz, 1H), 4.17-4.06 (m, 2H), 4.06 (s, 3H), 4.03 (d, J=3.6 Hz, 1H), 3.86 (d, J=12.5 Hz, 1H), 3.80 (s, 3H), 3.70-3.62 (m, 1H), 3.34 (s, 1H), 3.01 (s, 1H), 2.63 (d, J=9.0 Hz, 1H), 1.45 (d, J=5.0 Hz, 3H); $^{13}$C NMR (101 MHz, CDCl$_3$) δ 170.19, 151.95, 150.26, 147.56, 147.53, 144.59, 136.57, 131.23, 130.73, 128.36, 127.48, 123.71, 123.63, 119.16, 110.82, 110.72, 108.26, 108.22, 106.05, 104.86, 101.42, 101.35, 99.34, 74.44, 73.19, 71.99, 68.74, 67.71, 66.95, 56.44, 55.91, 20.97; HRMS-ESI calcd for C$_{29}$H$_{28}$O$_{12}$ (M+Na)$^+$ 591.14730, found 591.14668; mp 183.5-186° C.

Synthesis of 8b (PHY-33).

To a mixture of 7-O-(4,6-O-ethylidene-β-D-galactopyranosyl)-diphyllin (0.031 g, 0.055 mmol) and ground NaOH (0.044 g, 1.09 mmol) in DMSO (1.1 mL) was added MeI (0.204 mL, 3.27 mmol). The reaction was shaken 1 hour before being quenched with the simultaneous addition of water and EtOAc. The Organic layer was then washed with water (×3), brine, and then dried over sodium sulfate and concentrated under reduced pressure. Tritration (25% EtOH in hex) of the crude material afforded the desired methylated product, 7-O-(4,6-O-ethylidene-2,3-di-O-methyl-β-D-galactopyranosyl)-diphyllin (24 mg, 73%), as a white solid: $[\alpha]_D^{20}$+18° (c 1.1, CHCl$_3$); IR $\nu_{max}$ (KBr, cm$^{-1}$): 3082, 2938, 2906, 1759, 1623, 1596, 1507; $^1$H NMR (400 MHz, CDCl$_3$) δ 7.94 (s, 1H), 7.08 (s, 1H), 6.96 (dd, J=8.0, 1.7 Hz, 1H), 6.85-6.78 (m, 2H), 6.07 (dd, J=18.0, 1.3 Hz, 2H), 5.59 (dd, J=15.4, 2.2 Hz, 1H), 5.53 (d, J=15.4 Hz, 1H), 4.82 (d, J=7.8 Hz, 1H), 4.78 (q, J=4.9 Hz, 1H), 4.11 (d, J=3.4 Hz, 1H), 4.08 (s, 3H), 4.04 (d, J=14.7 Hz, 1H), 3.87-3.79 (m, 2H), 3.84 (s, 3H), 3.81 (s, 3H), 3.56 (s, 3H), 3.29 (dd, J=9.7, 3.5 Hz, 1H), 3.21 (s, 1H), 1.48 (d, J=5.1 Hz, 3H); $^{13}$C NMR (101 MHz, CDCl$_3$) δ 170.07, 151.96, 150.29, 147.65, 147.64, 144.70, 144.68, 136.58, 131.52, 131.49, 130.91, 128.52, 127.60, 123.80, 123.66, 119.46, 110.90, 110.78, 108.37, 108.32, 106.20, 105.14, 101.38, 101.29, 101.26, 99.38, 81.86, 79.99, 72.17, 68.84, 67.63, 66.77, 61.68, 58.02, 56.32, 55.98, 21.18; HRMS-ESI calcd for C$_{31}$H$_{32}$O$_{12}$ (M+Na)$^+$ 619.17860, found 619.17772; mp 175-177° C.

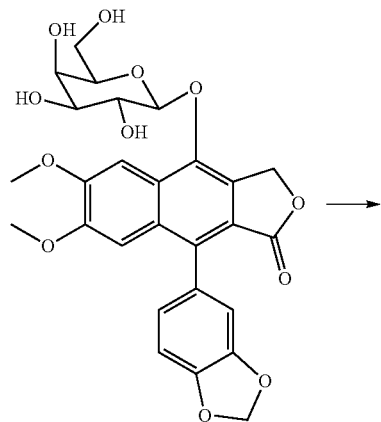

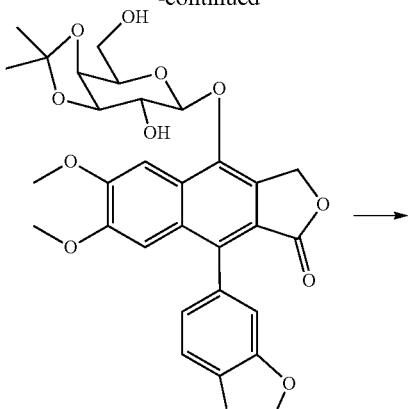

9a

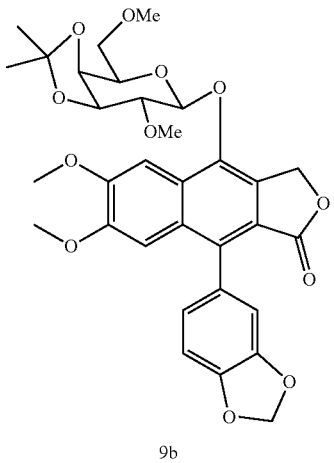

9b

Synthesis of 9a (PHY-34).

A slurry of β-D-galactopyranosyl-diphyllin (0.070 g, 0.129 mmol), p-toluenesulfonic acid (cat.), and 2,2-dimethoxy propane (1 mL) was allowed to stir for 4 days. Following the addition of water, the reaction mixture was allowed to stir 1 hr before extraction with EtOAc. The combined organic layers were washed with brine and then dried over sodium sulfate and concentrated under reduced pressure. Flash column chromatography (1→2% MeOH in DCM) afforded 9a (70 mg, 93%) as a white solid: $[\alpha]_D^{20}$ −7° (c 3.1, CHCl$_3$); IR $\nu_{max}$ (KBr, cm$^{-1}$): 3485, 3082, 2985, 2937, 2892, 2834, 1752, 1622, 1597, 1507; $^1$H NMR (400 MHz, CDCl$_3$) δ 7.90 (s, 1H), 7.06 (d, J=2.3 Hz, 1H), 6.93 (dd, J=7.9, 3.9 Hz, 1H), 6.78 (dd, J=3.6, 1.6 Hz, 1H), 6.75 (ddd, J=7.9, 3.1, 1.7 Hz, 1H), 6.08 (d, J=1.4 Hz, 1H), 6.04 (t, J=1.7 Hz, 1H), 5.58 (dd, J=15.3, 2.2 Hz, 1H), 5.44 (dd, J=15.2, 1.0 Hz, 1H), 4.75 (d, J=8.3 Hz, 1H), 4.25-4.17 (m, 2H), 4.04 (s, 3H), 4.03-3.95 (m, 2H), 3.90 (ddd, J=11.5, 4.7, 1.0 Hz, 1H), 3.84-3.80 (m, 1H), 3.79 (s, 3H), 1.63 (s, 3H), 1.40 (s, 3H); $^{13}$C NMR (101 MHz, CDCl$_3$) δ 170.04, 152.11, 150.32, 147.64, 147.60, 144.50, 136.80, 131.18, 131.16, 130.88, 128.34, 127.26, 123.71, 123.68, 119.33, 110.96, 110.79, 110.76, 108.31, 106.31, 104.45, 101.38, 100.89, 79.63, 74.18, 74.05, 73.68, 67.61, 62.44, 56.45, 55.97, 28.38, 26.46; HRMS-ESI calcd for C$_{30}$H$_{30}$O$_{12}$ (M+H)$^+$ 583.18100, found 583.18101; mp 166-168° C.

Synthesis of 9b (PHY-35).

To a solution of 9a (0.093 g, 0.160 mmol) in dimethyl sulfoxide (3.2 mL) was sequentially added crushed sodium hydroxide pellets (0.128 g, 3.19 mmol) and iodomethane (0.598 mL, 9.6 mmol) at rt. After 3 hours of shaking, the reaction solvent was quantitatively transferred away from the solid NaOH with DCM. The organic layer was then washed with several portions of water, brine, and then dried over sodium sulfate and concentrated under reduced pressure. Flash column chromatography (5:7.5:87.5 EtOAc/EtOH/Hex) afforded 9b (60 mg, 61%) as a white solid: $[\alpha]_D^{20}$ −7° (c 2.0, CHCl$_3$) IR $\nu_{max}$ (KBr, cm$^{-1}$): 3082, 2985, 2934, 2833, 1758, 1622, 1596, 1507; $^1$H NMR (400 MHz, CDCl$_3$) δ 7.93 (s, 1H), 7.07 (s, 1H), 6.96 (dd, J=7.9, 4.0 Hz, 1H), 6.89-6.78 (m, 2H), 6.11-6.03 (m, 2H), 5.70 (dd, J=15.3, 2.2 Hz, 1H), 5.45 (d, J=15.3 Hz, 1H), 4.67 (d, J=8.2 Hz, 1H), 4.20 (t, J=6.1 Hz, 1H), 4.13 (d, J=7.0 Hz, 1H), 4.06 (s, 3H), 3.80 (d, J=2.1 Hz, 6H), 3.81-3.75 (m, 1H), 3.72-3.66 (m, 2H), 3.64-3.58 (m, 1H), 3.38 (d, J=1.7 Hz, 3H), 1.65 (s, 3H), 1.39 (s, 3H); $^{13}$C NMR (101 MHz, CDCl$_3$) δ 170.18, 152.08, 150.27, 147.64, 144.76, 136.74, 131.76, 130.92, 128.62, 128.59, 127.42, 123.76, 123.71, 119.60, 110.90, 110.83, 110.54, 108.32, 106.35, 104.54, 101.36, 100.93, 82.70, 79.65, 73.91, 72.72, 71.88, 67.88, 60.29, 59.34, 56.24, 55.97, 28.28, 26.41; HRMS-ESI calcd for C$_{32}$H$_{34}$O$_{12}$ (M+Na)$^+$ 633.19425, found 633.19360; mp 115.5-118° C.

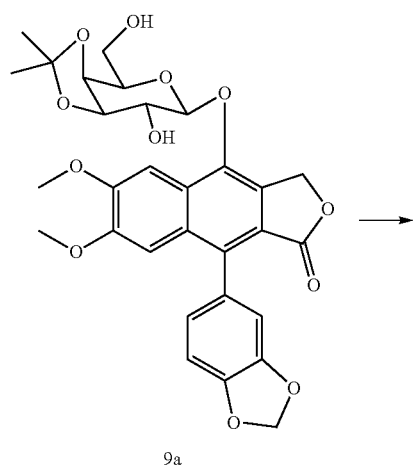

9a

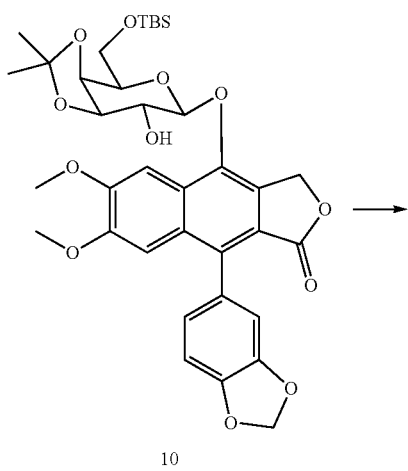

10

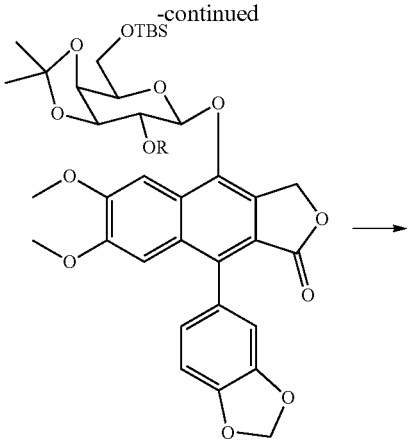

11a: R = CH$_2$CCH
12a: R = Bn
13a: R = Me

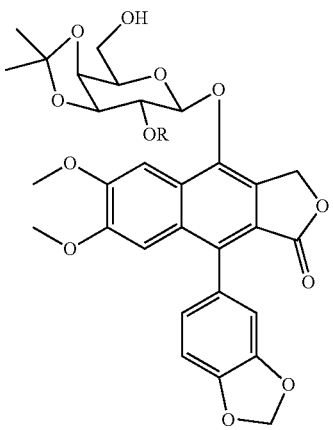

11b: R = CH$_2$CCH
12b: R = Bn
13b: R = Me

Synthesis of 10.

To a solution of 9a (0.155 g, 0.266 mmol) and imidazole (0.072 g, 1.064 mmol) in DMF (2.66 mL) at 0° C. was added TBSCl (0.120 g, 0.798 mmol). The reaction was stirred at 0° C. for 1 hour and then quenched with water. The aqueous layer was extracted with EtOAc and then dried over sodium sulfate and concentrated under reduced pressure. Flash column chromatography (silica gel; 2:1:17 EtOAc/EtOH/Hex) afforded 10 (66 mg, 79%) as a white solid: IR $\nu_{max}$ (KBr, cm$^{-1}$): 3446, 3082, 2954, 2930, 2884, 2857, 1760, 1623, 1597, 1507, 1481; $^1$H NMR (400 MHz, CDCl$_3$) δ 7.91 (s, 1H), 7.09 (s, 1H), 6.96 (dd, J=7.9, 1.8 Hz, 1H), 6.85-6.78 (m, 2H), 6.06 (dd, J=10.5, 9.0 Hz, 2H), 5.61 (dd, J=15.2, 3.2 Hz, 1H), 5.43 (dd, J=15.3, 1.6 Hz, 1H), 4.73 (d, J=8.3 Hz, 1H), 4.21 (dd, J=5.4, 2.0 Hz, 1H), 4.17-4.12 (m, 1H), 4.04 (s, 3H), 4.01 (d, J=7.8 Hz, 1H), 3.93-3.83 (m, 2H), 3.81 (s, 3H), 3.76 (t, J=6.2 Hz, 1H), 1.63 (s, 3H), 1.39 (s, 3H), 0.83 (d, J=0.9 Hz, 9H), 0.04 (s, 6H); $^{13}$C NMR (101 MHz, CDCl$_3$) δ 169.96, 152.09, 150.28, 147.65, 147.63, 144.38, 136.75, 131.60, 131.56, 130.88, 128.45, 128.43, 127.16, 123.73, 119.45, 110.83, 110.81, 110.62, 108.37, 108.35, 106.36, 104.51, 101.38, 100.80, 79.56, 74.48, 74.31, 73.33, 67.68, 62.04, 56.44, 55.99, 28.47, 26.40, 25.81 (3), 18.29, −5.31, −5.51; HRMS-ESI calcd for C$_{36}$H$_{44}$O$_{12}$Si (M+Na)$^+$ 719.24942, found 719.24939; mp 129-131° C.

Synthesis of 11a.

To a solution of crude 10 (0.161 mmol) in dimethylsulfoxide (3.22 mL) was sequentially added solid sodium hydroxide (0.129 g, 3.22 mmol) and propargyl-bromide (80% in toluene; 0.915 mL, 9.66 mmol). The reaction was shaken for two hours at rt until complete conversion was observed by TLC. Dichloromethane was added to the reaction mixture and the solid sodium hydroxide was filtered off, rinsing with several portions of dichloromethane. The resulting organics were rinsed several times with $H_2O$, brine, and then dried over sodium sulfate prior to concentrating in vacuo. Flash chromatography (silica gel; 10% EtOAc, 7.5% EtOH in Hexanes) afforded 11a (0.082 g, 69% over 2 steps from 5) as a pale orange solid: IR $\nu_{max}$ (KBr, cm$^{-1}$): 3271, 2930, 2857, 1759, 1622, 1507; $^1$H NMR (400 MHz, CDCl$_3$) δ 7.85 (s, 1H), 7.09 (s, 1H), 6.96 (dd, J=7.9, 2.1 Hz, 1H), 6.84-6.79 (m, 2H), 6.10 (t, J=1.3 Hz, 1H), 6.05 (dd, J=4.0, 1.5 Hz, 1H), 5.61 (dd, J=15.2, 3.3 Hz, 1H), 5.45 (dd, J=15.2, 1.8 Hz, 1H), 4.75 (d, J=8.2 Hz, 1H), 4.65 (dd, J=3.6, 2.4 Hz, 2H), 4.25-4.18 (m, 2H), 4.09 (s, 3H), 3.93 (dd, J=8.2, 6.2 Hz, 1H), 3.91-3.83 (m, 2H), 3.81 (d, J=0.4 Hz, 3H), 3.71 (t, J=6.6 Hz, 1H), 2.50 (t, J=2.4 Hz, 1H), 1.66 (s, 3H), 1.38 (s, 3H), 0.82 (d, J=1.2 Hz, 9H), 0.04 (d, J=1.0 Hz, 6H); $^{13}$C NMR (101 MHz, CDCl$_3$) δ 169.95, 152.13, 150.32, 147.65, 144.74, 144.51, 136.62, 131.46, 131.41, 130.89, 128.58, 128.54, 127.19, 123.74, 119.47, 110.86, 110.51, 108.36, 108.33, 106.37, 103.99, 101.37, 100.95, 100.93, 79.75, 79.70, 79.37, 75.14, 74.36, 73.48, 67.78, 67.76, 62.06, 59.05, 56.66, 55.98, 28.25, 26.39, 25.81, 18.27, −5.32, −5.51; HRMS-ESI calcd for $C_{39}H_{46}O_{12}Si$ (M+Na)$^+$ 757.26507, found 757.26348; mp 98-100° C.

Synthesis of 11b (PHY-40).

To a solution of 11a (0.060 g, 0.082 mmol) in dichloromethane (1 mL) was added tetrabutylammonium fluoride (1M in THF; 0.245 mL). The resulting solution was stirred at 40° C. overnight and then quenched with $H_2O$ the following morning after cooling to rt. The aqueous layer was extracted with several portions of dichloromethane and the combined organics were rinsed with brine, dried over sodium sulfate, and then concentrated in vacuo. Flash column chromatography (silica gel; 10% EtOH, 10% EtOAc in Hex) then afforded 11b (0.044 g, 87%) as a white solid: IR $\nu_{max}$ (KBr, cm$^{-1}$): 3521, 3287, 3061, 2987, 2937, 2834, 2118, 2034, 1755, 1623, 1597, 1506; $^1$H NMR (400 MHz, CDCl$_3$) δ 7.85 (s, 1H), 7.07 (s, 1H), 6.95 (ddd, J=7.7, 2.0, 0.5 Hz, 1H), 6.83-6.77 (m, 2H), 6.09 (d, J=1.5 Hz, 1H), 6.05 (dd, J=1.9, 1.5 Hz, 1H), 5.59 (dd, J=15.3, 1.5 Hz, 1H), 5.47 (dd, J=15.3, 1.9 Hz, 1H), 4.79 (d, J=8.1 Hz, 1H), 4.65 (dd, J=3.7, 2.4 Hz, 2H), 4.29-4.25 (m, 1H), 4.23 (dd, J=5.5, 2.0 Hz, 1H), 4.09 (s, 3H), 3.95 (dd, J=8.1, 6.8 Hz, 2H), 3.92-3.86 (m, 1H), 3.80 (s, 3H), 3.79-3.75 (m, 1H), 2.51 (t, J=2.4 Hz, 1H), 2.02 (dd, J=6.8, 4.5 Hz, 1H), 1.66 (s, 3H), 1.40 (s, 3H); $^{13}$C NMR (75 MHz, CDCl$_3$) δ 169.96, 152.17, 150.37, 147.66, 144.62, 136.75, 131.15, 130.96, 128.49, 128.47, 127.29, 123.76, 123.70, 119.43, 110.89, 110.85, 110.82, 108.33, 106.38, 103.92, 101.37, 100.98, 79.57, 79.45, 79.41, 75.27, 74.32, 73.56, 67.68, 62.44, 59.07, 56.64, 55.98, 28.16, 26.45; HRMS-ESI calcd for $C_{33}H_{32}O_{12}$ (M+Na)$^+$ 643.17860, found 643.17744; mp 139-141° C.

Synthesis of 12a.

To a solution of 10 (0.050 g, 0.072 mmol) in dichloromethane (2.9 mL) was added 2N sodium hydroxide (2.9 mL) and a catalytic amount of tetrabutylammonium iodide. The resulting mixture was stirred at room temperature for 10 minutes prior to the addition of benzyl bromide (0.043 mL, 0.359 mmol). The reaction was allowed to stir overnight at room temperature. The layers were separated and the aqueous layer was extracted with dichloromethane. The combined organics layers were then washed with brine, dried over sodium sulfate, and concentrated in vacuo. Flash chromatography (silica gel; 5% ACN in Toluene) afforded 12a (0.044 g, 78%) as a white crystalline solid: IR $\nu_{max}$ (KBr, cm$^{-1}$): 3066, 2984, 2952, 2931, 2884, 2857, 1761, 1622, 1597, 1507; $^1$H NMR (300 MHz, CDCl$_3$) δ 7.78 (s, 1H), 7.48 (dd, J=7.7, 1.7 Hz, 2H), 7.37-7.29 (m, 3H), 7.08 (s, 1H), 6.96 (dd, J=7.8, 1.1 Hz, 1H), 6.84-6.78 (m, 2H), 6.09 (d, J=0.8 Hz, 1H), 6.05 (dd, J=3.1, 1.5 Hz, 1H), 5.60 (dd, J=15.2, 2.8 Hz, 1H), 5.44 (d, J=15.4 Hz, 1H), 5.07 (d, J=11.4 Hz, 1H), 4.95 (d, J=11.4 Hz, 1H), 4.81 (d, J=8.2 Hz, 1H), 4.31 (dd, J=6.9, 5.5 Hz, 1H), 4.21 (dd, J=5.4, 2.0 Hz, 1H), 3.89-3.80 (m, 3H), 3.78 (s, 3H), 3.70 (d, J=6.0 Hz, 1H), 3.49 (s, 3H), 1.53 (s, 3H), 1.38 (s, 3H), 0.81 (d, J=1.1 Hz, 9H), 0.03 (s, 6H); $^{13}$C NMR (75 MHz, CDCl$_3$) δ 169.97, 152.10, 150.24, 147.61, 144.44, 138.00, 136.57, 132.09, 132.06, 130.86, 129.14, 128.90, 128.69, 128.59, 128.55, 128.14, 127.23, 123.71, 119.40, 110.82, 110.28, 108.34, 108.30, 106.37, 104.35, 101.33, 100.82, 80.50, 79.85, 77.58, 77.16, 76.74, 74.30, 74.23, 73.51, 67.80, 62.05, 55.91, 28.17, 26.41, 25.76, 18.21, −5.36, −5.55; HRMS-ESI calcd for $C_{43}H_{50}O_{12}Si$ (M+Na)$^+$ 809.29637, found 809.29454; mp 92-94° C.

Synthesis of 12b (PHY-50).

To a solution of 12a (0.044 g, 0.056 mmol) in dichloromethane (0.56 mL) was added tetrabutylammonium fluoride (1.0M in THF, 0.168 mL). The resulting mixture was stirred at 40° C. overnight. The reaction mixture was concentrated in vacuo, after which flash chromatography (silica gel; 10% ACN in Toluene) afforded 12b (0.031 g, 82%) as an off-white solid: [α]$_D^{20}$+26° (c 0.8, CHCl$_3$); IR $\nu_{max}$ (KBr, cm$^{-1}$): 3523, 3066, 2984, 2934, 1756, 1622, 1597, 1506; $^1$H NMR (400 MHz, CDCl$_3$) δ 7.79 (s, 1H), 7.50-7.45 (m, 2H), 7.37-7.29 (m, 3H), 7.07 (s, 1H), 6.95 (d, J=8.1 Hz, 1H), 6.86-6.77 (m, 2H), 6.09 (d, J=1.4 Hz, 1H), 6.04 (t, J=1.4 Hz, 1H), 5.56 (dd, J=15.3, 2.0 Hz, 1H), 5.45 (dd, J=15.2, 1.3 Hz, 1H), 5.06 (d, J=11.4 Hz, 1H), 4.95 (d, J=11.4 Hz, 1H), 4.84 (d, J=8.1 Hz, 1H), 4.39-4.34 (m, 1H), 4.23 (dd, J=5.6, 2.1 Hz, 1H), 3.95 (ddd, J=11.4, 6.2, 1.4 Hz, 1H), 3.90-3.84 (m, 2H), 3.78 (s, 3H), 3.77-3.73 (m, 1H), 3.55 (s, 3H), 1.53 (s, 3H), 1.40 (s, 3H); $^{13}$C NMR (101 MHz, CDCl$_3$) δ 170.00, 152.15, 150.30, 147.66, 144.52, 137.86, 136.75, 131.76, 130.97, 128.70, 128.60, 128.50, 128.48, 128.23, 127.33, 123.75, 123.70, 119.37, 110.85, 110.81, 110.71, 108.34, 106.39, 104.28, 101.37, 100.86, 100.85, 80.18, 79.87, 74.38, 74.28, 73.46, 67.71, 62.48, 55.99, 55.94, 28.09, 26.49; HRMS-ESI calcd for $C_{37}H_{36}O_{12}$ (M+Na)+695.20990, found 695.20862; mp 125-127° C.

Synthesis of 13a.

To a solution of 10 (0.060 g, 0.086 mmol) in dimethyl sulfoxide (3.2 mL) was sequentially added crushed sodium hydroxide pellets (0.069 g, 1.72 mmol) and iodomethane (0.321 mL, 5.16 mmol) at rt. After 3 hrs of shaking, the reaction was quenched with the simultaneous addition of water and EtOAc. The combined organic layers were then washed with several portions of water, brine, and then dried over sodium sulfate and concentrated under reduced pressure. Flash column chromatography (silica gel; 7.5% EtOH, 3% EtOAc in Hex) afforded 13a (0.049 g, 80%) as a white solid: IR $\nu_{max}$ (KBr, cm$^{-1}$): 2933, 2885, 2857, 1763, 1623, 1596, 1507; $^1$H NMR (400 MHz, CDCl$_3$) δ 7.92 (s, 1H), 7.09 (s, 1H), 6.96 (dd, J=7.7, 1.5 Hz, 1H), 6.87-6.78 (m, 2H), 6.13-6.02 (m, 2H), 5.63 (dd, J=15.2, 3.2 Hz, 1H), 5.44 (d, J=15.2 Hz, 1H), 4.70 (d, J=8.2 Hz, 1H), 4.21-4.15 (m, 2H), 4.07 (s, 3H), 3.91-3.83 (m, 2H), 3.81 (s, 3H), 3.80 (s, 3H), 3.69 (t, J=6.3 Hz, 1H), 3.62-3.58 (m, 1H), 1.65 (s, 3H), 1.38 (s, 3H), 0.82 (s, 9H), 0.04 (s, 6H); $^{13}$C NMR (101 MHz, CDCl$_3$) δ 169.95, 152.08, 150.28, 147.64, 144.68, 144.66, 136.64, 131.71, 131.67, 130.90, 128.56, 128.53, 127.29, 123.75, 119.49, 110.86, 110.85, 110.33, 108.36, 108.32, 106.38, 104.72, 101.36, 100.95, 100.93, 82.89, 79.58, 74.35, 73.37, 67.73, 62.11, 60.34, 56.25, 55.98, 28.34, 26.37, 25.81, 18.28, −5.32, −5.51; HRMS-ESI calcd for C$_{37}$H$_{46}$O$_{12}$Si (M+Na)$^+$ 733.26507, found 733.26497; mp 121-123° C.

Synthesis of 13b (PHY-37).

To a solution of 13a (0.024 g, 0.034 mmol) in dichloromethane (0.5 mL) was added tetrabutylammonium fluoride (1M in THF, 0.100 mL). The reaction was allowed to stir at 40° C. overnight. After cooling to room temperature, the reaction mixture was quenched with water and extracted with dichloromethane. The combined organic layers were washed with brine and then dried over sodium sulfate and concentrated under reduced pressure. Flash column chromatography (silica gel; 10% EtOH, 3% EtOAc in Hex) afforded 13b (0.018 g, 89%) as a white solid: [α]$_D^{20}$+7 (c 1.9, CHCl$_3$); IR ν$_{max}$ (KBr, cm$^{-1}$): 3529, 2986, 2937, 2834, 1757, 1623, 1597, 1507; $^1$H NMR (400 MHz, CDCl$_3$) δ 7.91 (s, 1H), 7.07 (s, 1H), 6.93 (dd, J=7.7, 4.5 Hz, 1H), 6.79 (dd, J=11.2, 6.3 Hz, 2H), 6.06 (d, J=15.9 Hz, 2H), 5.60 (d, J=15.3 Hz, 1H), 5.45 (d, J=15.3 Hz, 1H), 4.74 (d, J=8.0 Hz, 1H), 4.26-4.18 (m, 2H), 4.06 (s, 3H), 4.00-3.93 (m, 1H), 3.92-3.85 (m, 1H), 3.80 (s, 6H), 3.77-3.72 (m, 1H), 3.61 (dd, J=7.5, 6.7 Hz, 1H), 2.06 (s, 1H), 1.65 (s, 3H), 1.40 (s, 3H); $^{13}$C NMR (101 MHz, CDCl$_3$) δ 170.00, 152.10, 150.31, 147.62, 144.74, 136.72, 131.37, 130.94, 128.44, 127.36, 123.74, 123.68, 119.42, 110.84, 110.79, 110.67, 108.29, 106.35, 104.57, 101.35, 100.95, 82.63, 79.59, 74.21, 73.54, 67.65, 62.46, 60.35, 56.26, 55.96, 28.24, 26.41; HRMS-ESI calcd for C$_{31}$H$_{32}$O$_{12}$ (M+Na)$^+$ 619.17860, found 619.17828; mp 145-147° C.

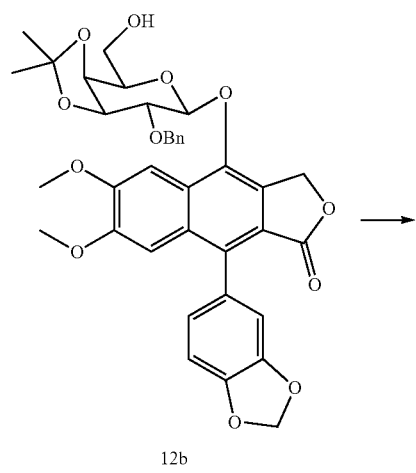

12b

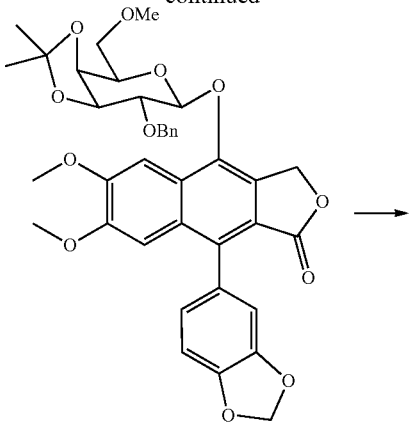

12c

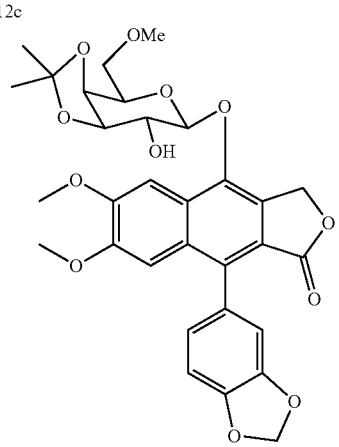

12d

Synthesis of 12c (PHY-51).

To a solution of 12b (0.038 g, 0.056 mmol) in dimethylformamide (1.5 mL) at 0° C. was added 60% sodium hydride (0.007 g, 0.168 mmol). The resulting mixture was stirred for 30 minutes at 0° C. prior to the addition of methyl iodide (0.014 mL, 0.224 mmol). The reaction was allowed to warm to room temperature before being heated to 80° C. After stirring at 80° C. for 3 hours, the reaction mixture was diluted with ethyl acetate and quenched with water. Following extraction by ethyl acetate, the combined organic layers were washed with brine, dried over sodium sulfate, and then concentrated under reduced pressure. Flash chromatography (silica gel; 5% EtOH, 1% EtOAc in Hex) afforded 12c (0.028 g, 73%) as a white solid: [α]$_D^{20}$+12° (c 1.9, CHCl$_3$); IR ν$_{max}$ (KBr, cm$^{-1}$): 3065, 2985, 2931, 1759, 1622, 1596, 1506; $^1$H NMR (400 MHz, CDCl$_3$) δ 7.80 (s, 1H), 7.48 (d, J=7.0 Hz, 2H), 7.37-7.29 (m, 3H), 7.07 (s, 1H), 6.96 (dd, J=7.9, 4.1 Hz, 1H), 6.90-6.77 (m, 2H), 6.09 (s, 1H), 6.05 (s, 1H), 5.66 (dd, J=15.3, 2.2 Hz, 1H), 5.45 (d, J=15.3 Hz, 1H), 5.Z07 (d, J=11.5 Hz, 1H), 4.96 (d, J=11.4 Hz, 1H), 4.79 (d, J=8.2 Hz, 1H), 4.36-4.30 (m, 1H), 4.16 (dd, J=5.4, 1.7 Hz, 1H), 3.89-3.79 (m, 2H), 3.78 (s, 3H), 3.67 (d, J=5.7 Hz, 2H), 3.50 (s, J=6.9 Hz, 3H), 3.36 (d, J=2.0 Hz, 3H), 1.52 (s, 3H), 1.39 (s, 3H); $^{13}$C NMR (101 MHz, CDCl$_3$) δ 170.19, 152.11, 150.24, 147.63, 144.53, 137.93, 136.70, 132.12, 130.91, 128.67, 128.59, 128.19, 127.39, 123.74, 123.71, 119.50, 110.88, 110.83, 110.49, 108.33, 106.35, 104.21, 101.35, 100.81, 80.20, 79.90, 74.17, 74.04, 72.66, 71.81, 67.96, 59.36, 55.92, 28.11, 26.47; HRMS-ESI calcd for C$_{38}$H$_{38}$O$_{12}$ (M+Na)$^+$ 709.22555, found 709.22481; mp 109-111° C.

Synthesis of 12d (PHY-54).

Argon was bubbled through a stirring solution of 12c (0.032 g, 0.047 mmol) in ethyl acetate (2 mL) for ten minutes prior to the addition of 20% palladium (II) hydroxide on carbon (0.007 g, 0.009 mmol). Hydrogen gas was then bubbled through this stirring suspension for 15 minutes, after which the reaction mixture was allowed to stir at room temperature under an atmosphere of hydrogen overnight. The reaction mixture was filtered through celite, rinsed with ethyl acetate, and then concentrated in vacuo. Flash chromatography (silica gel; 10% EtOH, 7.5% EtOAc in Hex) afforded 12d (0.017 g, 61%) as an off-white solid: $[\alpha]_D^{20}$-27° (c 1.2, CHCl$_3$); IR $\nu_{max}$ (KBr, cm$^{-1}$): 3437, 3083, 2985, 2931, 1755, 1622, 1597, 1507; $^1$H NMR (400 MHz, CDCl$_3$) δ 7.93 (s, 1H), 7.07 (d, J=1.9 Hz, 1H), 6.95 (dd, J=7.9, 3.9 Hz, 1H), 6.87-6.76 (m, 2H), 6.09 (t, J=1.4 Hz, 1H), 6.05 (dd, J=2.2, 1.5 Hz, 1H), 5.68 (dd, J=15.3, 2.7 Hz, 1H), 5.44 (dd, J=15.3, 1.6 Hz, 1H), 4.69 (dd, J=8.3, 0.8 Hz, 1H), 4.18-4.13 (m, 2H), 4.03 (s, 3H), 4.02-3.98 (m, 1H), 3.87 (t, J=5.8 Hz, 1H), 3.80 (s, 3H), 3.72-3.68 (m, 2H), 3.38 (d, J=1.8 Hz, 3H), 2.92 (s, 1H), 1.63 (s, 3H), 1.39 (s, 3H); $^{13}$C NMR (101 MHz, CDCl$_3$) δ 170.15, 152.12, 150.31, 147.65, 147.63, 144.56, 136.82, 131.61, 130.88, 128.54, 128.51, 127.31, 123.76, 123.70, 119.57, 110.88, 110.83, 110.80, 108.32, 106.37, 106.35, 104.47, 101.37, 100.90, 79.76, 74.18, 73.89, 72.88, 71.80, 67.83, 59.36, 56.40, 55.97, 28.40, 26.44; HRMS-ESI calcd for C$_{31}$H$_{32}$O$_{12}$ (M+Na)$^+$ 619.17860, found 619.17761; mp 140-142° C.

Synthesis of 13c (PHY-49).

To a solution of 13b (0.022 g, 0.037 mmol) and tetrabutylammonium iodide (cat.) in dichloromethane (1.5 mL) was sequentially added NaOH (2N; 1.5 mL) and propargylbromide (80% in toluene; 0.017 mL, 0.184 mmol). The resulting solution was allowed to stir at rt for 4 days. The reaction was quenched with H$_2$O and the resulting aqueous layer was extracted several times with dichloromethane. Combined organics were rinsed with brine, dried over sodium sulfate, and then concentrated in vacuo. Flash chromatography (silica gel; 10% ACN in toluene) then afforded 13c (0.015 g, 64%) as a white crystalline solid: IR $\nu_{max}$ (KBr, cm$^{-1}$): 3276, 2985, 2934, 1758, 1622, 1596, 1507; $^1$H NMR (400 MHz, CDCl$_3$) δ 7.92 (s, 1H), 7.08 (s, 1H), 6.96 (dd, J=7.8, 3.3 Hz, 1H), 6.90-6.77 (m, 2H), 6.09 (s, 1H), 6.05 (s, 1H), 5.71 (dd, J=15.3, 1.9 Hz, 1H), 5.44 (d, J=15.4 Hz, 1H), 4.68 (d, J=8.1 Hz, 1H), 4.25-4.11 (m, 4H), 4.06 (s, 3H), 3.84 (d, J=5.1 Hz, 2H), 3.81 (s, 3H), 3.80 (s, 3H), 3.65-3.58 (m, 1H), 2.44 (d, J=1.9 Hz, 1H), 1.65 (s, 3H), 1.39 (s, 3H); $^{13}$C NMR (101 MHz, CDCl$_3$) δ 170.17, 152.08, 150.26, 147.63, 144.69, 136.74, 131.82, 130.91, 128.57, 127.37, 123.77, 123.70, 119.62, 110.90, 110.82, 110.60, 108.32, 106.36, 104.48, 101.36, 100.88, 82.66, 79.63, 79.19, 75.23, 73.87, 72.61, 69.27, 67.90, 60.29, 58.69, 56.25, 55.97, 28.26, 26.41; mp 212-214° C.

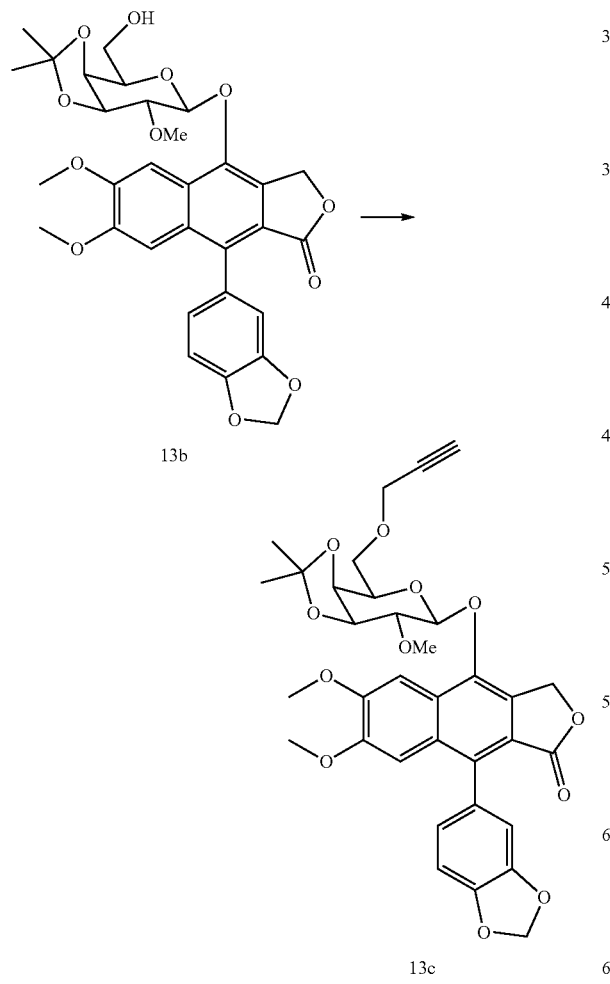

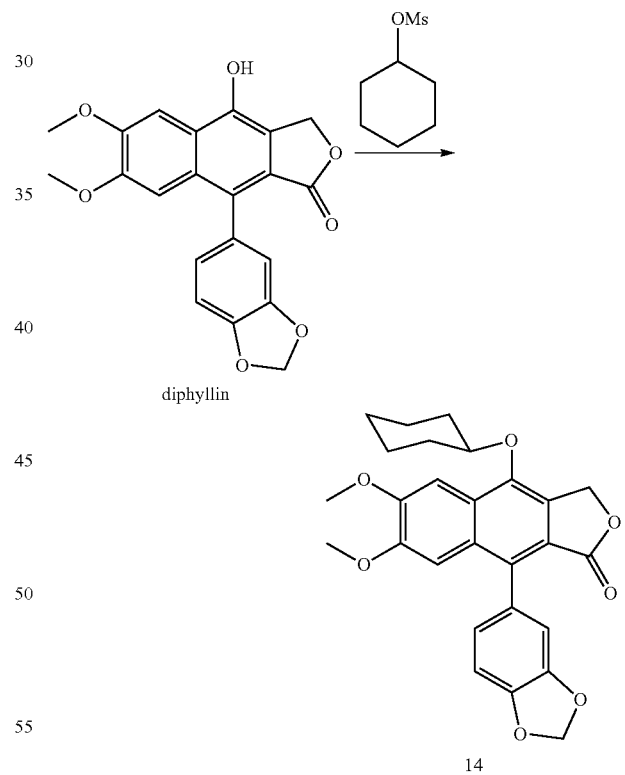

Synthesis of 14 (PHY-52).

To a mixture of diphyllin (0.050 g, 0.131 mmol) and Cs$_2$CO$_3$ (0.085 g, 0.262 mmol) in DMF (0.5 mL) was added cyclohexyl mesylate (0.026 g, 0.144 mmol) at rt. The resulting mixture was then brought to 80° C. and allowed to stir overnight. The reaction was then cooled to rt, quenched with H$_2$O, and extracted with ethyl acetate. The combined organic layers were then rinsed with H$_2$O, brine, and dried over sodium sulfate prior to concentrating under reduced pressure. Flash chromatography (silica gel; 3-5% ACN in toluene) then afforded 14 (0.017 g, 28%) as an off-white solid: IR $v_{max}$ (KBr, cm$^{-1}$): 2935, 2857, 1760, 1621, 1596, 1506; $^1$H NMR (400 MHz, CDCl$_3$) δ 7.59 (s, 1H), 7.07 (s, 1H), 6.96 (d, J=7.9 Hz, 1H), 6.85-6.79 (m, 2H), 6.07 (dd, J=18.2, 1.5 Hz, 2H), 5.40 (s, 2H), 4.26-4.18 (m, 1H), 4.06 (s, 3H), 3.81 (s, 3H), 2.10-2.00 (m, 2H), 1.93-1.83 (m, 2H), 1.78-1.67 (m, 2H), 1.67-1.53 (m, 1H), 1.44-1.33 (m, 3H); $^{13}$C NMR (101 MHz, CDCl$_3$) δ 169.91, 151.53, 150.34, 147.63, 147.55, 146.13, 134.50, 130.85, 128.73, 127.70, 126.98, 123.82, 119.38, 110.96, 108.32, 106.29, 101.34, 101.30, 80.65, 67.02, 56.10, 55.97, 33.09, 25.55, 24.00; HRMS-ESI calcd for C$_{27}$H$_{26}$O$_7$ (M+Na)$^+$ 485.15707, found 485.15595; mp 202-204° C.

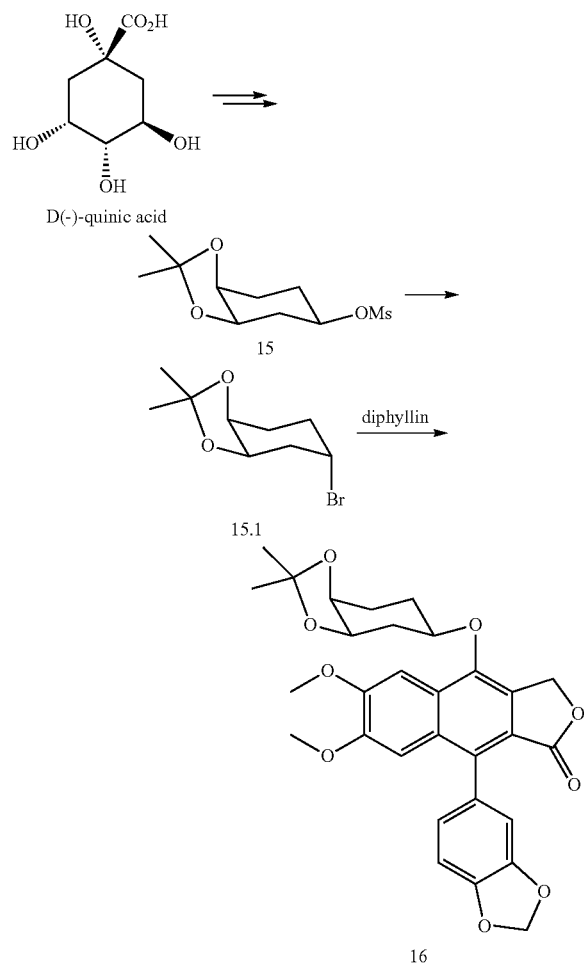

Synthesis of 16 (PHY-55).

Mesylate 15 was prepared from D(−)-quinic acid according to the work of Albertini et al. (Tetrahedron 1997, 53, 17177): $^1$H NMR (300 MHz, CDCl$_3$) δ 4.69-4.56 (m, 1H), 4.23-4.09 (m, 2H), 3.02 (s, J=2.6 Hz, 3H), 2.29-2.12 (m, 2H), 1.97-1.84 (m, 3H), 1.78-1.65 (m, 1H), 1.52 (s, 3H), 1.34 (s, 3H).

A mixture of 15 (0.106 g, 0.423 mmol) and LiBr (0.441 g, 5.08) in THF (18 mL) was brought to reflux. After stirring for 1.5 hr at reflux, TLC analysis prompted the addition of more LiBr (0.220 g, 2.53 mmol). The reaction was stirred for an additional 1 hr at reflux before TLC revealed complete conversion of starting material. The reaction mixture was then filtered through a plug of silica gel using 10% EtOAc in hexanes to rinse. Concentration of the filtrate in vacuo afforded 15.1 as a clear yellow oil (0.076 g, 76%) which appeared pure by NMR: $^1$H NMR (300 MHz, CDCl$_3$) δ 4.45-4.35 (m, 1H), 4.28 (q, J=5.3 Hz, 1H), 4.16 (dd, J=9.8, 4.9 Hz, 1H), 2.37-2.16 (m, 2H), 2.16-2.05 (m, 2H), 1.92-1.74 (m, 2H), 1.48 (s, 3H), 1.34 (s, 3H).

To a mixture of diphyllin (0.064 g, 0.167 mmol) and Cs$_2$CO$_3$ (0.109 g, 0.334 mmol) in DMF (0.5 mL) was added a solution of 15.1 (0.059 g, 0.251 mmol) in DMF (0.5 mL) at rt. The resulting mixture was then brought to 80° C. and allowed to stir. Upon complete conversion of starting material, as observed by TLC after 1 hr of stirring, the reaction was cooled to rt and quenched with H$_2$O. Following extraction with ethyl acetate, the combined organic layers were rinsed with H$_2$O, brine, and then dried over magnesium sulfate prior to being concentrated in vacuo. Flash chromatography (silica gel; 5% ACN in toluene) then afforded 16 (0.049 g, 55%) as an off-white solid: IR $v_{max}$ (KBr, cm$^{-1}$): 2931, 1760, 1621, 1506; $^1$H NMR (400 MHz, CDCl$_3$) δ 7.59 (s, 1H), 7.07 (s, 1H), 6.95 (d, J=7.9 Hz, 1H), 6.85-6.77 (m, 2H), 6.07 (dd, J=18.1, 1.4 Hz, 2H), 5.40 (s, 2H), 4.25-4.17 (m, 2H), 4.18-4.11 (m, 1H), 4.06 (s, 3H), 3.81 (s, 3H), 2.33-2.21 (m, 2H), 2.09-1.98 (m, 2H), 1.98-1.88 (m, 1H), 1.75-1.63 (m, 1H), 1.60 (s, 3H), 1.38 (s, 3H); $^{13}$C NMR (101 MHz, CDCl$_3$) δ 169.78, 151.76, 150.43, 147.66, 147.62, 146.06, 135.15, 130.94, 128.56, 127.85, 127.78, 123.78, 119.37, 110.89, 108.80, 108.34, 106.35, 101.37, 101.25, 78.12, 73.58, 72.39, 66.80, 56.19, 55.98, 35.77, 28.65, 27.11, 26.30, 24.16; HRMS-ESI calcd for C$_{30}$H$_{30}$O$_9$ (M+Na)$^+$ 557.17820, found 557.17658.

Example 2

A first series of phyllanthusmin analogues were synthesized (FIG. 1).

Cytotoxicity Against HT-29 Cells.

The cytotoxicity of the compounds in FIG. 1 was screened against HT-29 cells by a previously reported procedure (Ren Y et al. *J. Nat. Prod* 2011, 74, 1117-1125). A summary of the results is described in Table 1.

TABLE 1

Antiproliferative activities of PHY analogs against HT-29 cells.

| PHY Compound | IC$_{50}$ (µM) |
|---|---|
| 17 | 1.42 |
| 18 | 0.57 |
| 19 | 1.56 |
| 20 | 1.21 |
| 21 | 0.018 |
| 22 | 6.9 |
| 23 | 1.44 |
| 24 | 0.626 |
| 25 | 0.0017 |
| 26 | NT* |
| 27 | NT* |
| 28 | 1.55 |
| 29 | 19.02 |
| 30 | 0.0108 |
| 31 | 0.00529 |

*IC$_{50}$ were not tested against HT-29 cells. Data obtained in other cell lines.

Water Solubility.

The phyllanthusmin compounds generally exhibit limited water solubility. A series of compounds were synthesized to improve their water solubility. In particular, phyllanthusmin derivatives including an arabinose derivative with a free C$_2$ hydroxy group, have been explored to produce phosphate, succinate, and amino acid conjugates. In addition PHY-25 and PHY-30 have also been synthesized to contain similar alcohol functionality that can ultimately be utilized to improve water solubility. PHY-28 and PHY-29 containing a glucosamine moiety were also synthesized for improved water solubility. The water solubility of these and other PHY derivatives was assessed (Table 2) to establish a baseline of solubility in a series of 4 solutions. This was accomplished using a plate reader-based absorbance assay.

TABLE 2

Solubility of PHY compounds.

| Compound | M.W. | Solubility in DMSO (mg/ml) | Solubility in PEG300 (mg/ml) | Solubility in 10% Cremaphor EL/PBS (mg/ml) | Solubility in PBS (mg/ml) |
| --- | --- | --- | --- | --- | --- |
| PHY-1 | 711 | 97 | 33 | 8.4 | 0.12 |
| PHY-3 | 380 | 16 | 30 | 8.9 | 0.18 |
| PHY-4 | 639 | 63 | 32 | 9.4 | 0.17 |
| PHY-7 | 555 | 112 | 5.7 | 7.4 | 0.14 |
| PHY-11 | 639 | 83 | 15 | 10 | 0.18 |
| PHY-15 | 711 | 75 | 14 | 10 | 0.20 |
| PHY-20 | 639 | 86 | 24 | 10 | 0.16 |

* In Table 2, PHY-1 is phyllanthusmins D; PHY-3 is phyllanthusmins B; PHY-4 is phyllanthusmins C; PHY-7 is 7-O-((2,3,4-tri-O-acetyl)-α-L-arabinopyranosyl) diphyllin; PHY-11 is phyllanthusmins C; PHY-14 is phyllanthusmins C; PHY-15 is phyllanthusmins C; and PHY-20 is phyllanthusmins C (all previous described in PCT/US2015/23657).

Example 3

A second series of phyllanthusmin analogues were synthesized (FIG. 2) along with the natural product acutissimalignan A. After purification, all of the synthesized compounds were analyzed for purity by HPLC and tested for biological testing.

Figure 2:
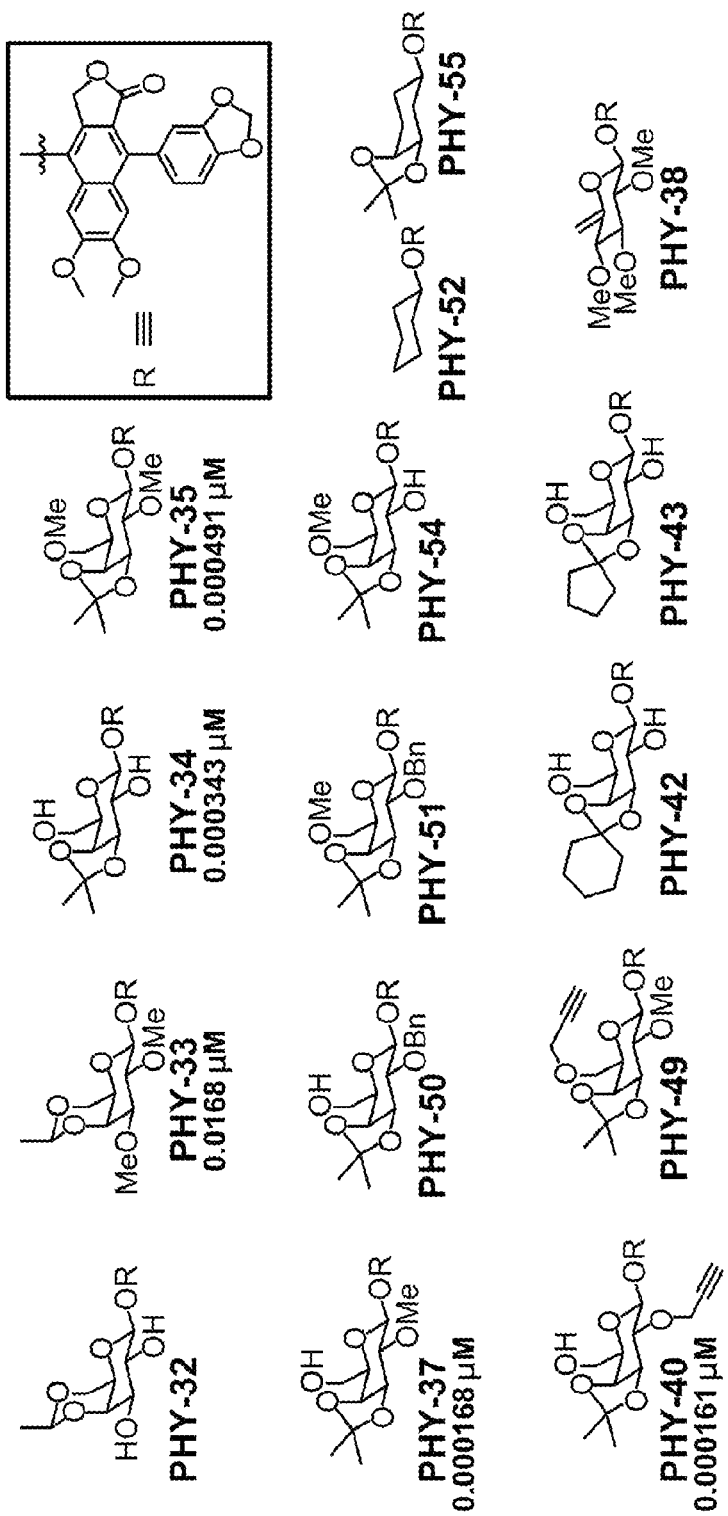
FIG. 2 displays the structures of several arylnaphthalene ligands disclosed herein.
Figure 2:
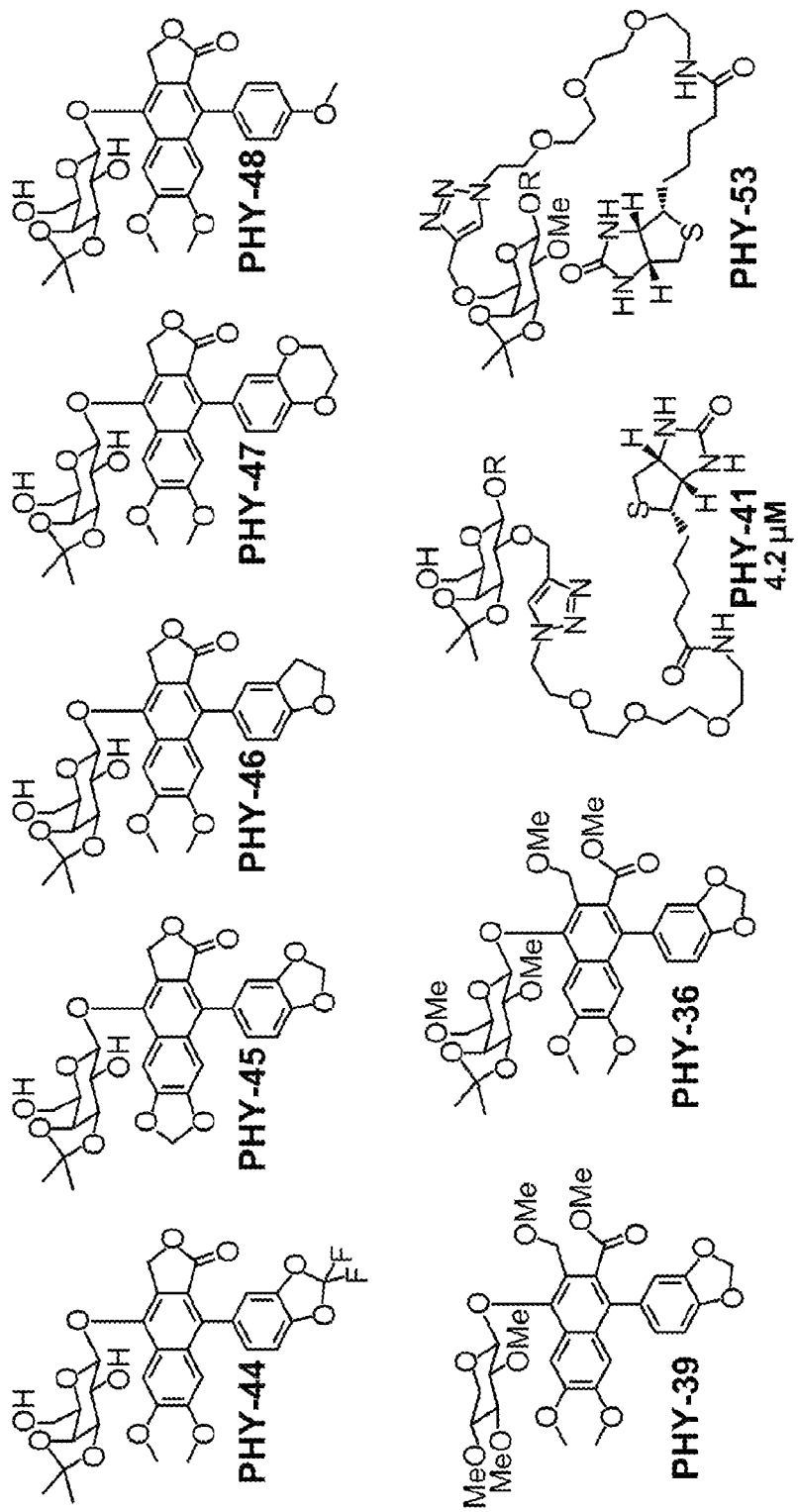
Figure 3A:
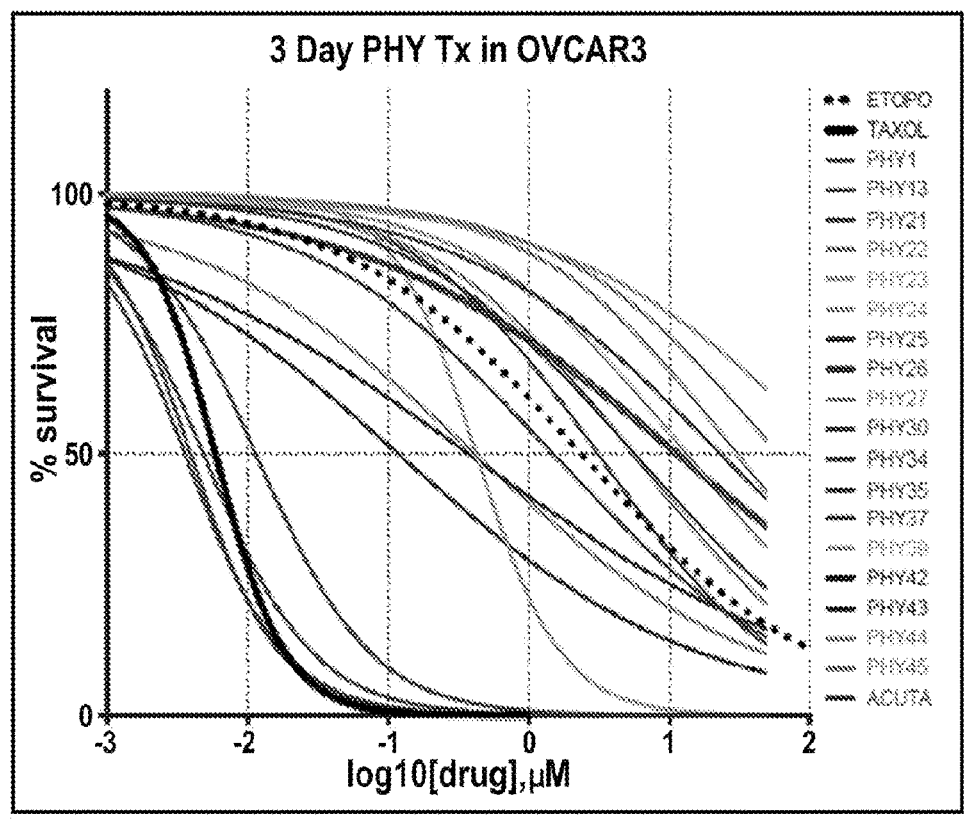
FIGS. 3A and 3B are graphs showing the survival of ovarian cancer cell lines (OVCAR3 and OVCAR8) in the presence of various arylnaphthalene ligands.
Figure 3B:
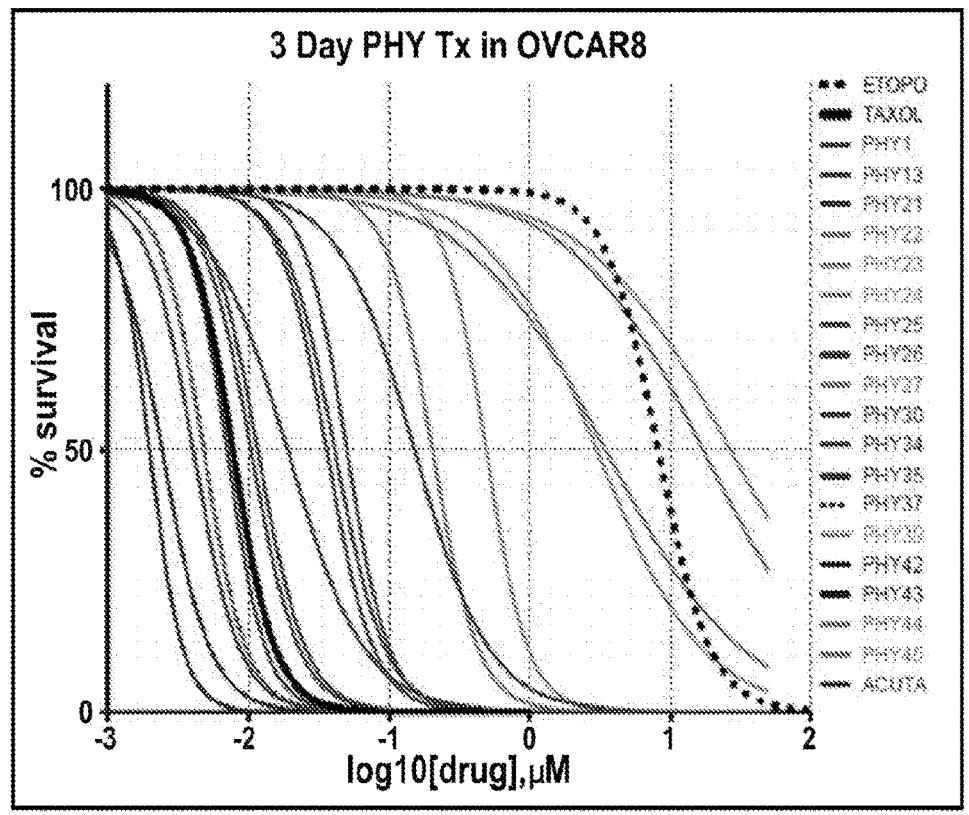
Figure 4:
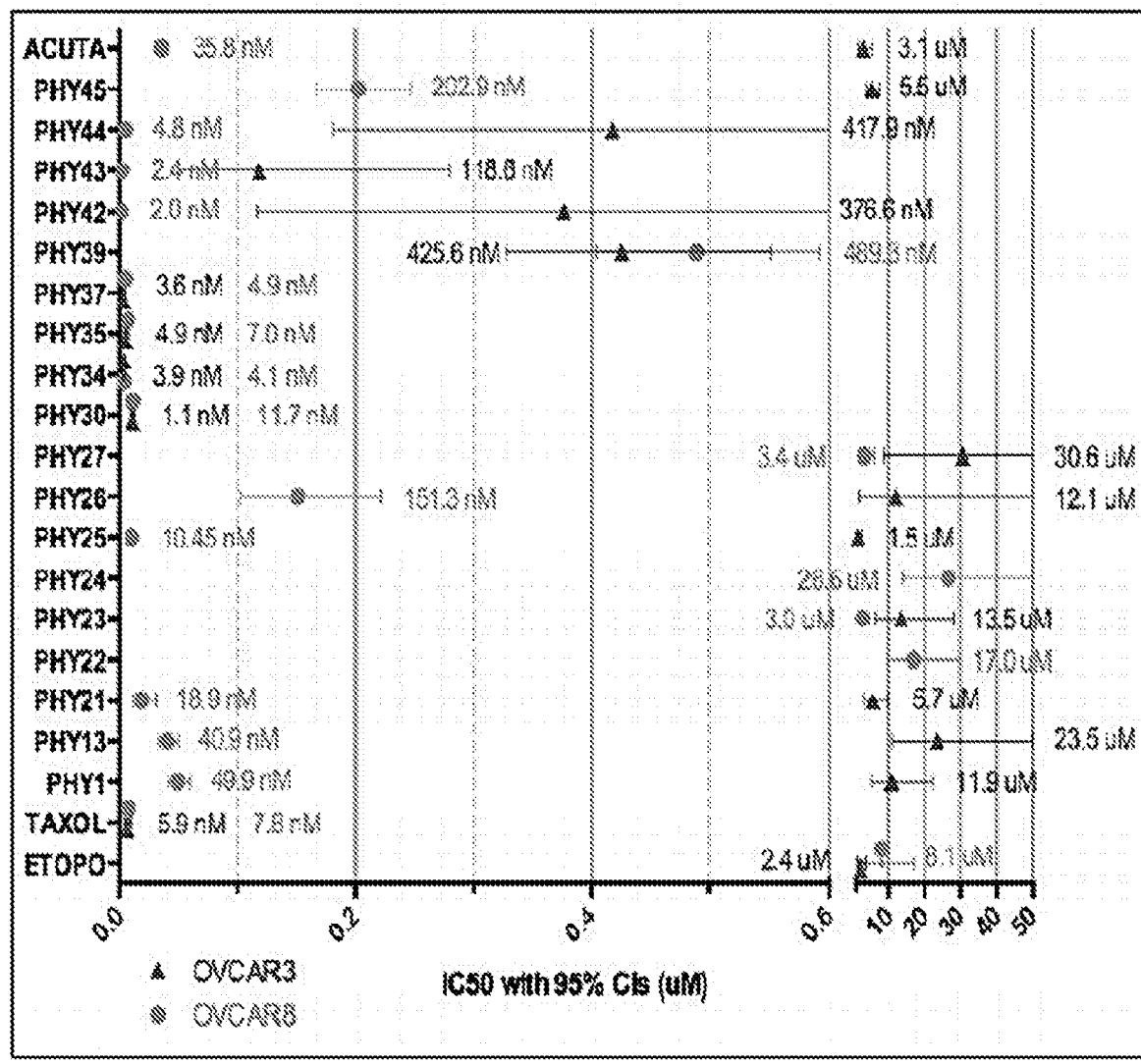
FIG. 4 is a graph showing the IC50 values of arylnaphthalene ligands tested against ovarian cancer cell lines (OVCAR3 and OVCAR8).

Ovarian Cancer Cells:

The compounds shown in FIG. 2 were tested against two different ovarian cancer cell lines (xenograft mouse model OVCAR3 and OVCAR8 ovarian cancer cell lines). Of these compounds, PHY-34 (FIG. 2) exhibited the highest potency in the ovarian cancer cell lines. These compounds are more potent than etoposide. They also do not affect topoisomerase activity. A summary of the test data is shown in FIGS. 3A, 3B, and 4 and Table 3. A comparison of the $IC_{50}$ values of the compounds in FIG. 2 in two of the ovarian cancer cell lines (OVCAR3 and OVCAR8) reveal subtle differences in activity. Some compounds showed nearly identical $IC_{50}$ values in both cells, while others are different.

TABLE 3

Comparison of the IC50 values of analogues in two of ovarian cancer cell lines (OVCAR3 and OVCAR8).

|  | OVCAR3 IC50 (uM) | OVCAR8 IC50 (uM) |
| --- | --- | --- |
| ETOPO | 2.381 | 8.126 |
| TAXOL | 0.005911 | 0.00776 |
| PHY1 | 10.91 | 0.04985 |
| PHY13 | 23.49 | 0.04088 |
| PHY21 | 5.735 | 0.01887 |
| PHY22 | 60.11 | 17.02 |
| PHY23 | 13.46 | 2.973 |
| PHY24 | 155.5 | 26.59 |
| PHY25 | 1.504 | 0.01045 |
| PHY26 | 12.05 | 0.1513 |
| PHY27 | 30.64 | 3.44 |

TABLE 3-continued

Comparison of the IC50 values of analogues in two of ovarian cancer cell lines (OVCAR3 and OVCAR8).

|  | OVCAR3 IC50 (uM) | OVCAR8 IC50 (uM) |
| --- | --- | --- |
| PHY30 | 0.01146 | 0.01167 |
| PHY34 | 0.003939 | 0.004063 |
| PHY35 | 0.004854 | 0.007044 |
| PHY37 | 0.003589 | 0.004867 |
| PHY39 | 0.4256 | 0.4893 |
| PHY42 | 0.3766 | 0.001986 |
| PHY43 | 0.1186 | 0.002437 |
| PHY44 | 0.4179 | 0.004783 |
| PHY45 | 5.516 | 0.2029 |
| ACUTA | 3.127 | 0.03578 |

PHY-34 exhibited sub-nanomolar activity in vitro in HT-29 cells, single digit nanomolar activity in numerous other cell lines and, demonstrated efficacy in vivo in a hollow fiber assay. PHY analogues 35, 37, 40, 49, 50, 51, and 54 represent analogues of PHY-34 and can be used to analyze the effect of differential functionalization of the hydroxyl groups present on the sugar moiety.

PHY analogues 32 and 33 demonstrate the loss of potency observed when the position of the acetal group is moved on the ring. PHY-42 and 43, however, show that variation in the size of the acetal moiety is well tolerated. Analogues 44-48 assess deviations in core structure, focusing on the A- and D-aryl rings. PHY-52 and -55 address the potential metabolic vulnerability of the glycosidic linkage. PHY-41 and -53 are biotinylated analogues may identify the molecular target for this class of compounds. The difference in location of the biotin on the glycone may identify a tolerated position.

PHY-34 was tested in the NCI 60-cell COMPARE assay system and data was recently obtained indicating a few compounds that share significant correlations with PHY-34 based on this assay, but these compounds do not appear to have a conserved mechanism of action.

The solubility, maximum tolerated dose, and pharmacokinetics of the phyllanthusmins, facilitating the in vivo studies with PHY-34, were also determined. These studies established reasonable solubility for the phyllanthusmins using PEG300 formulation. PHY-34 solution was shown to be stable (no significant degradation) upon storage for one week at temperatures ranging from 4° C. to −80° C. This study was not carried out to further time points to look at long-term degradation of the compound. The MTD of the compound was shown to be 1.8 mpk for IP administration. Interestingly, however, oral dosing showed no toxicity up to 30 mpk even though reasonable AUCs could be achieved through this dosing route.

Figure 5:
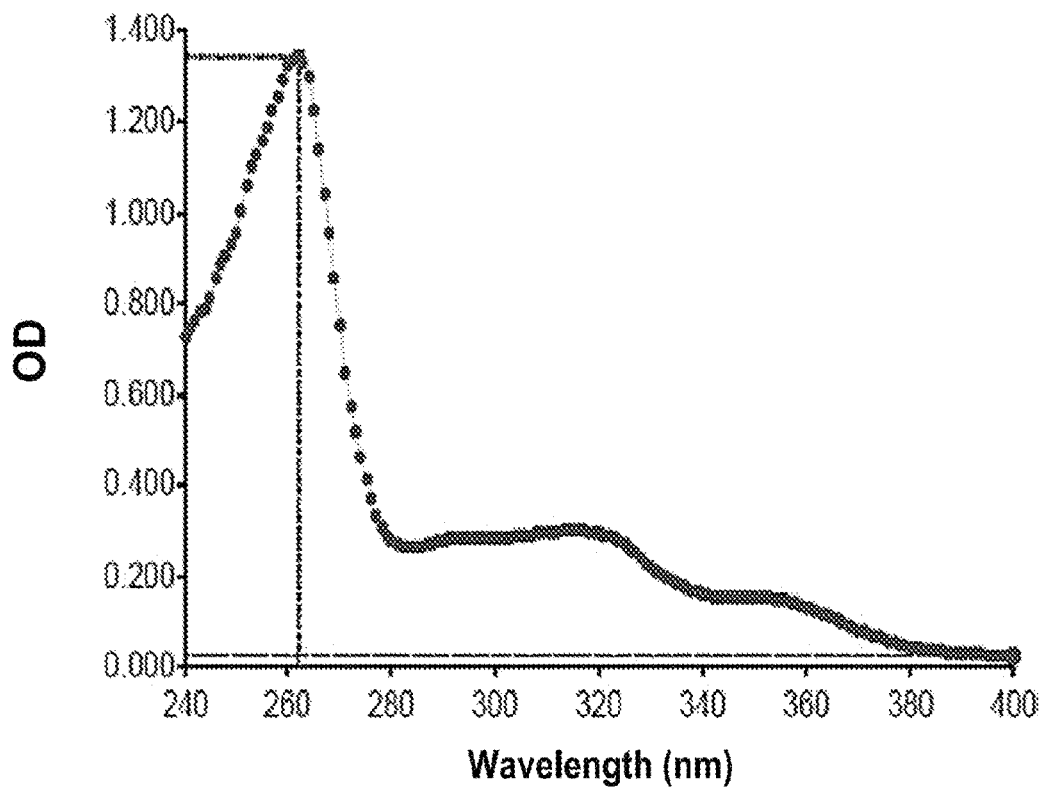
FIG. 5 is a graph showing the absorbance of arylnaphthalene formulated with PEG300 and saline.
Figure 6A:
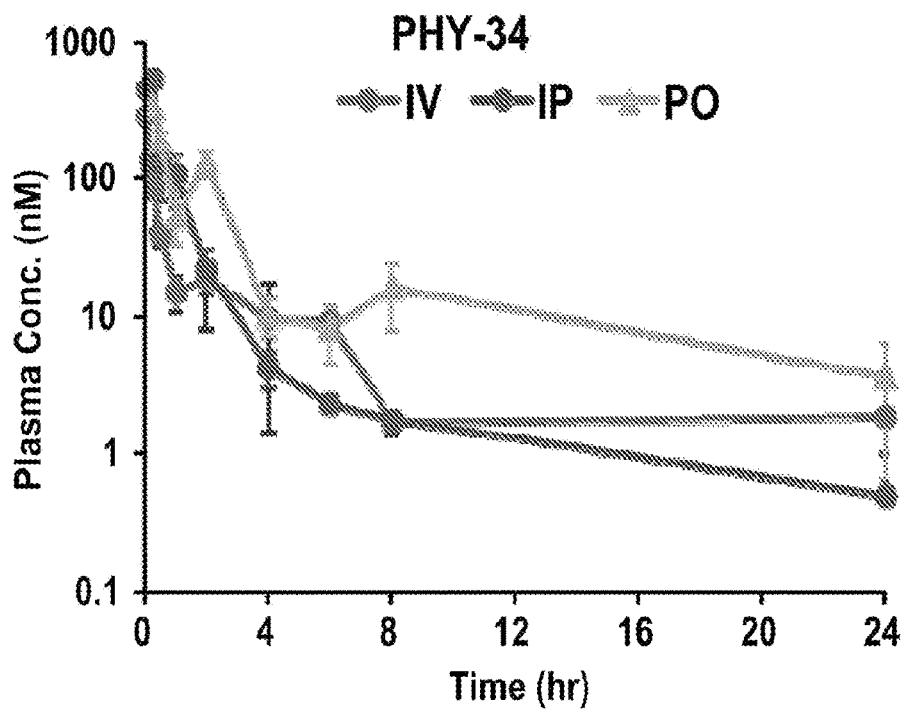
FIGS. 6A and 6B are graphs showing the concentration-time profile of PHY-34 in mouse plasma via different administration routes.
Figure 6B:
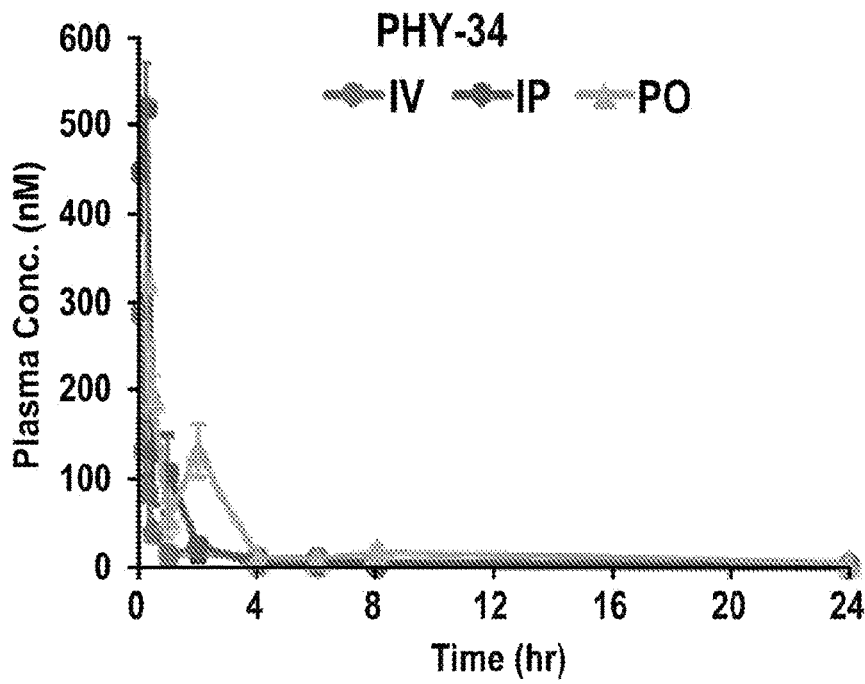
Figure 7:
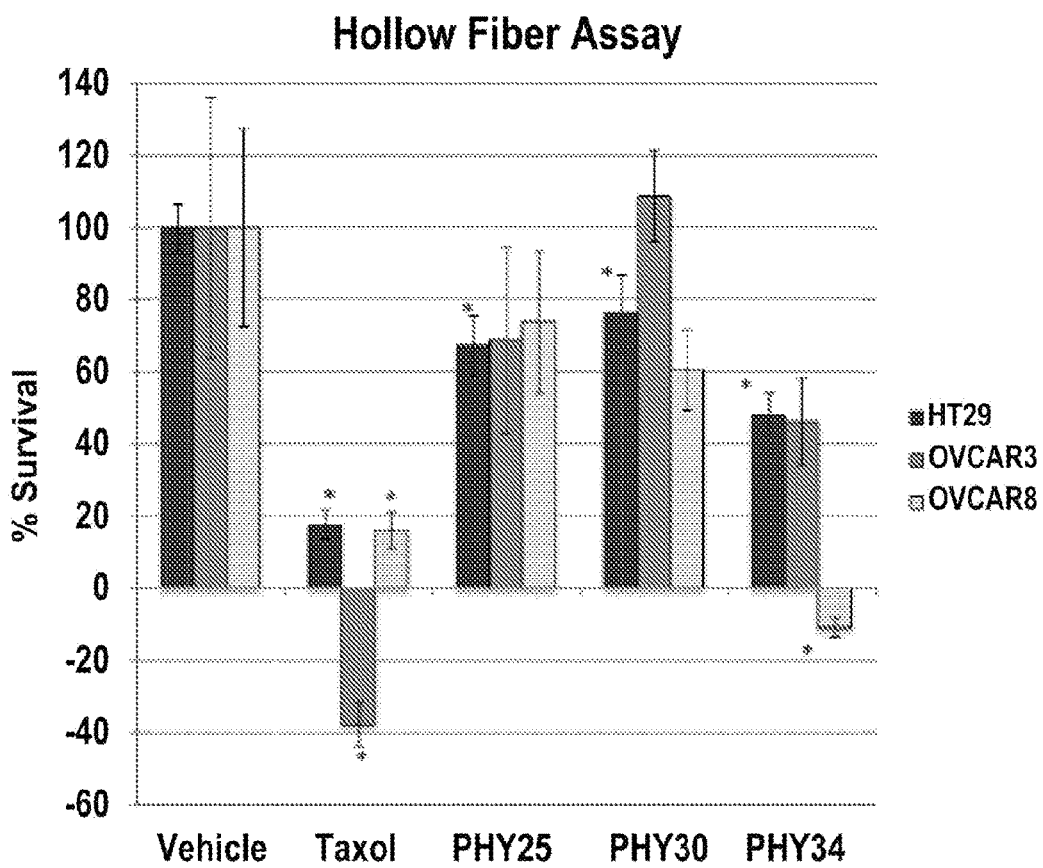
FIG. 7 is a graph showing a hollow fiber assay of various compounds. *p<0.05 as compared to vehicle control using ANOVA w/ mult. comparisons (Holm's method).
Figure 8:
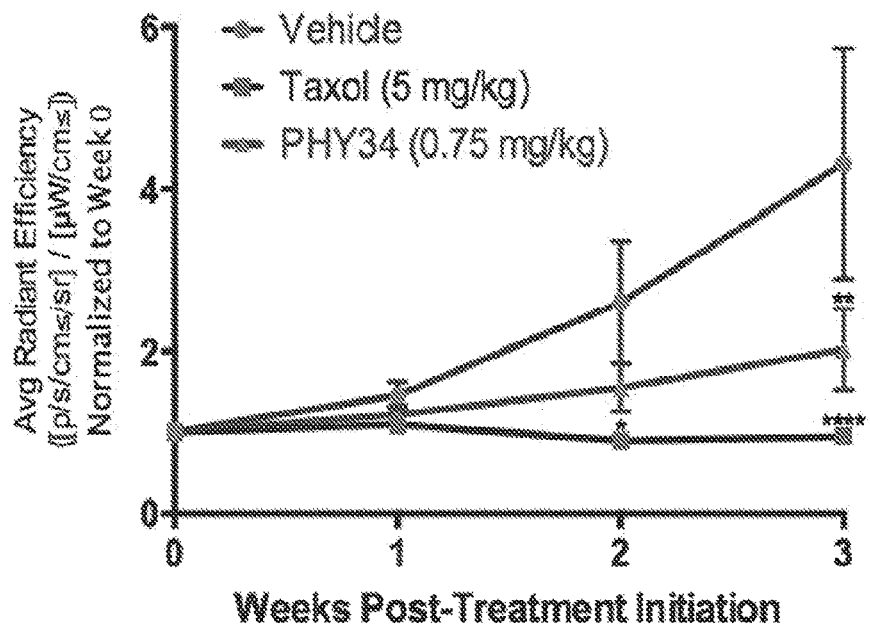
FIG. 8 is a graph showing OVCAR8-RFP xenograft IVIS imaging.
Figure 9A:
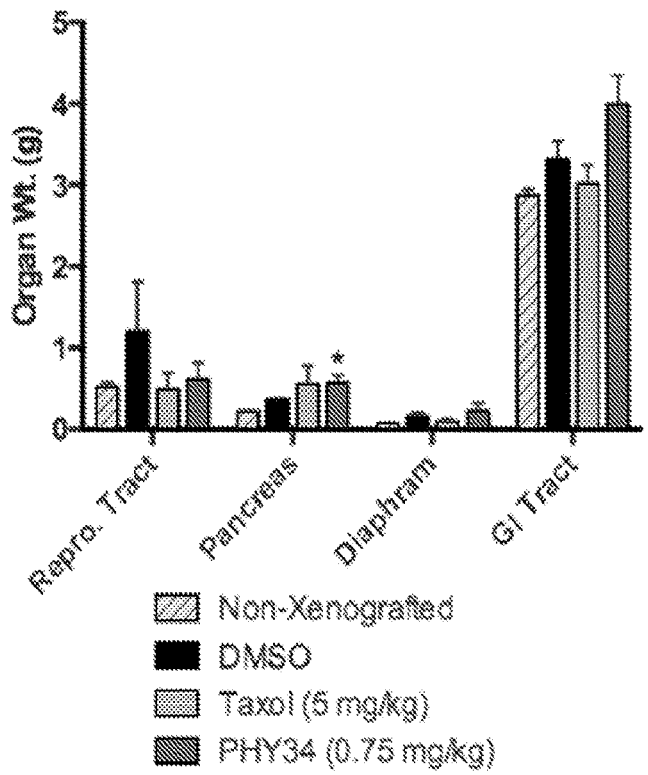
FIGS. 9A-9C are bar graphs showing tumor burdens in various organs in the presence of Taxol or PHY-34.
Figure 9B:
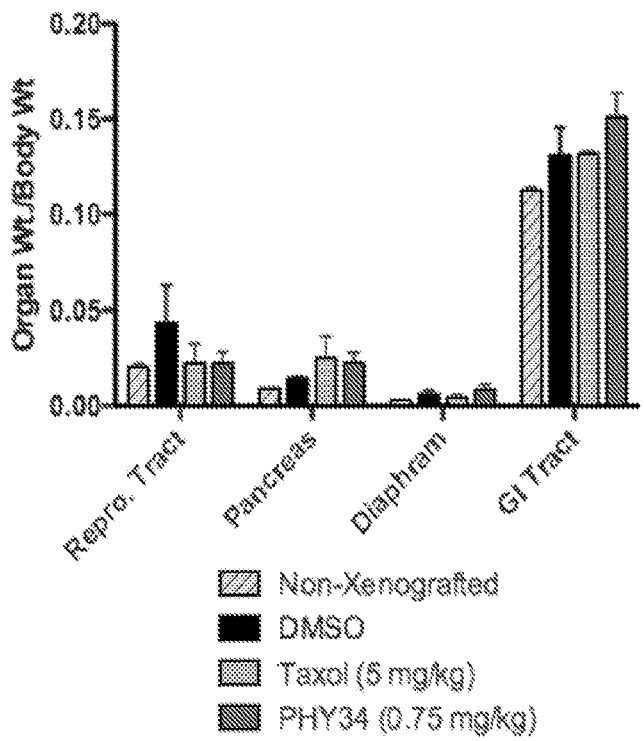
Figure 9C:
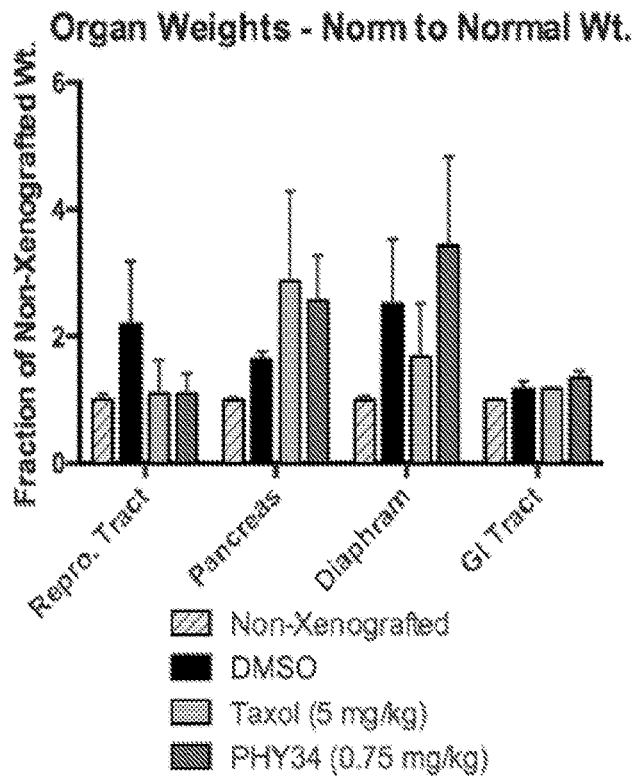
Figure 10A:
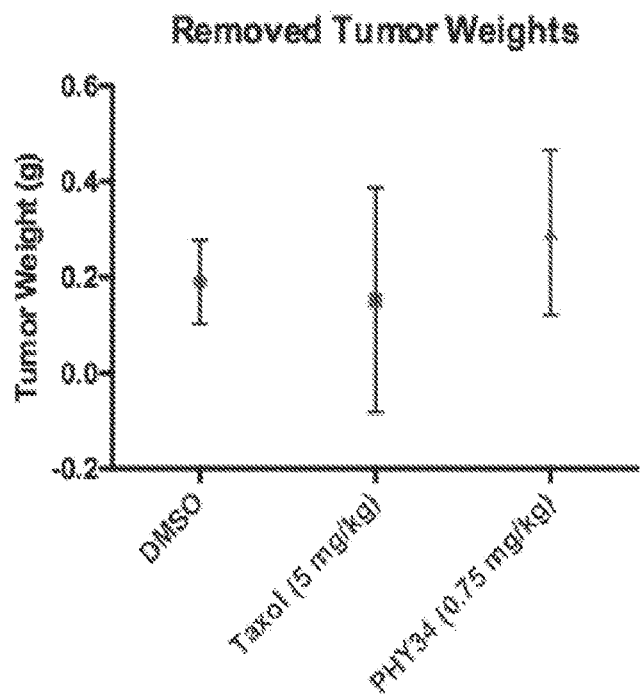
FIGS. 10A-10D are graphs showing tumor weight, tumor count, and ascites weight in the presence of Taxol or PHY-34.
Figure 10B:
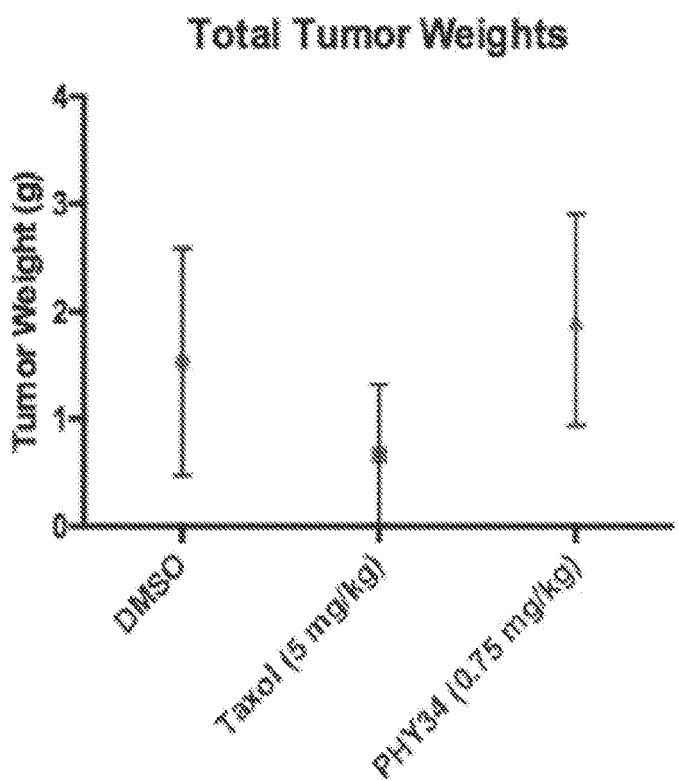
Figure 10C:
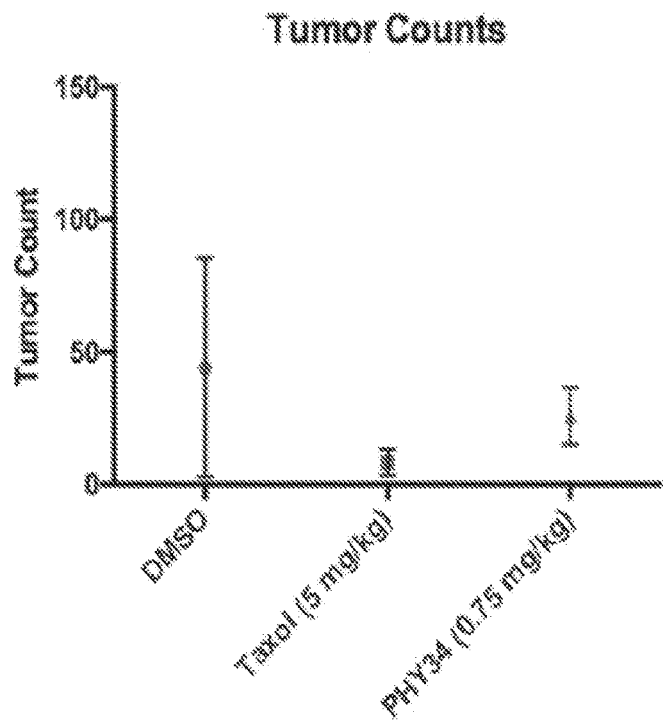
Figure 10D:
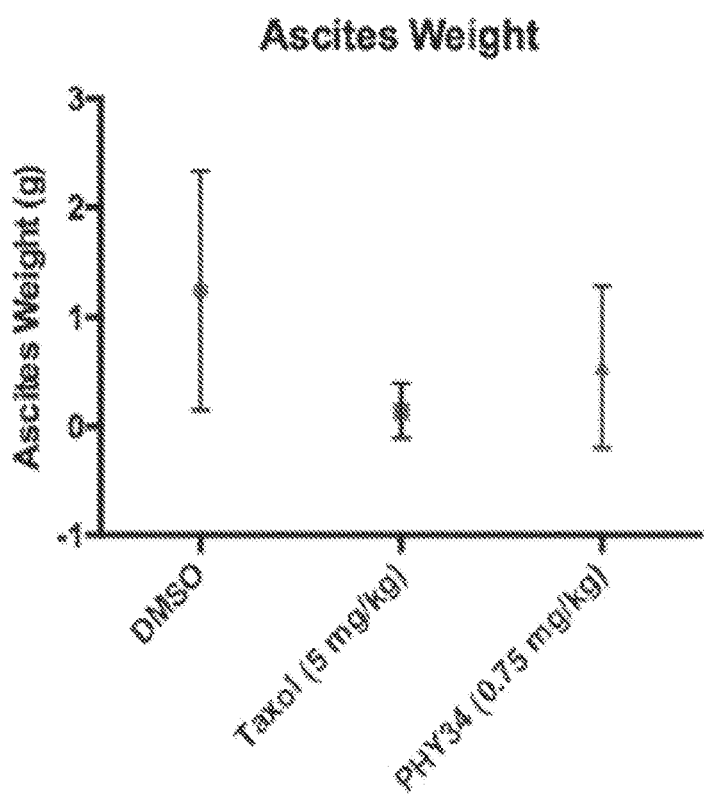
Figure 11:
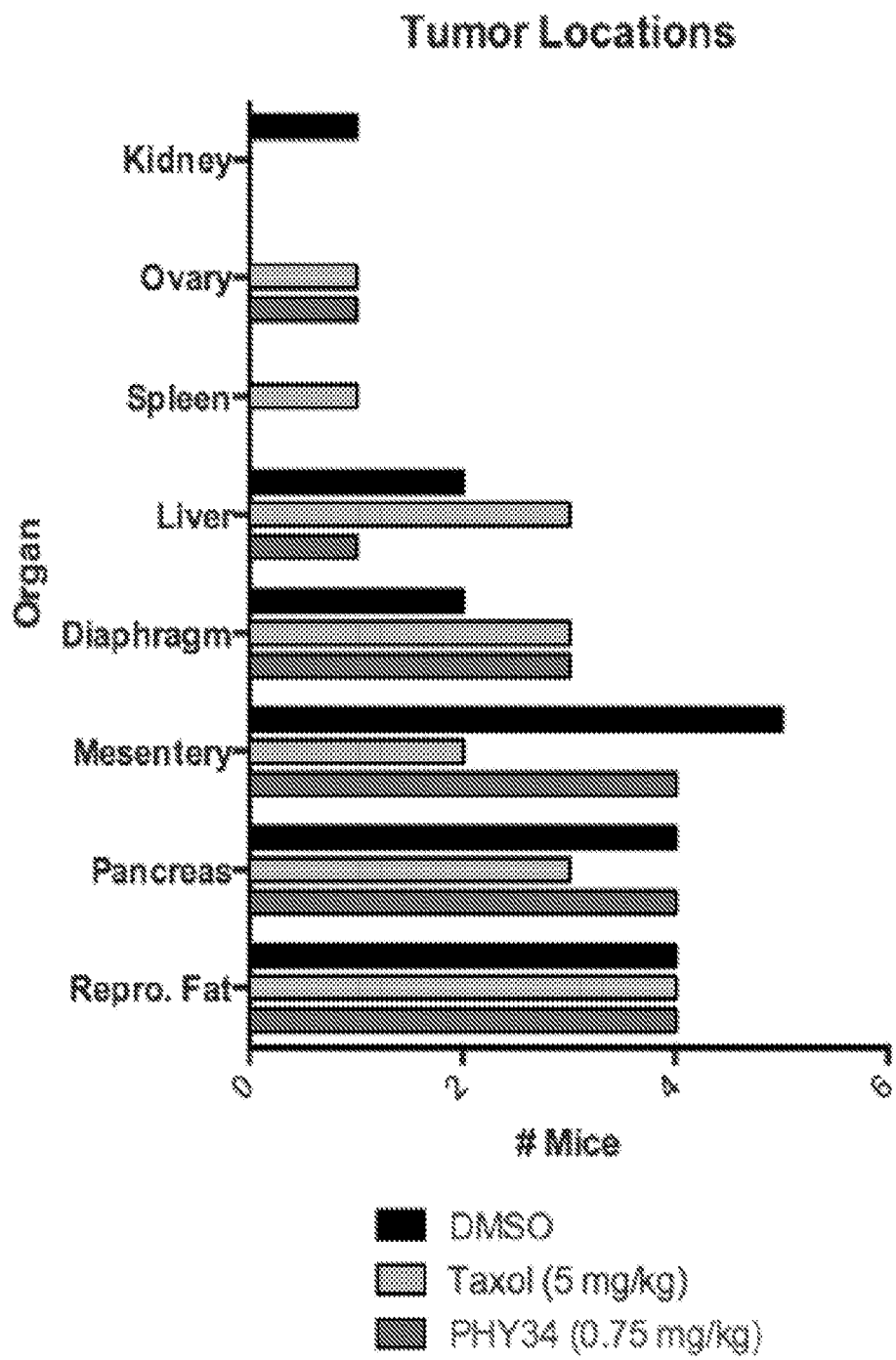
FIG. 11 is a bar graph showing tumor location in mice in the presence of Taxol or PHY-34.
Figure 12:
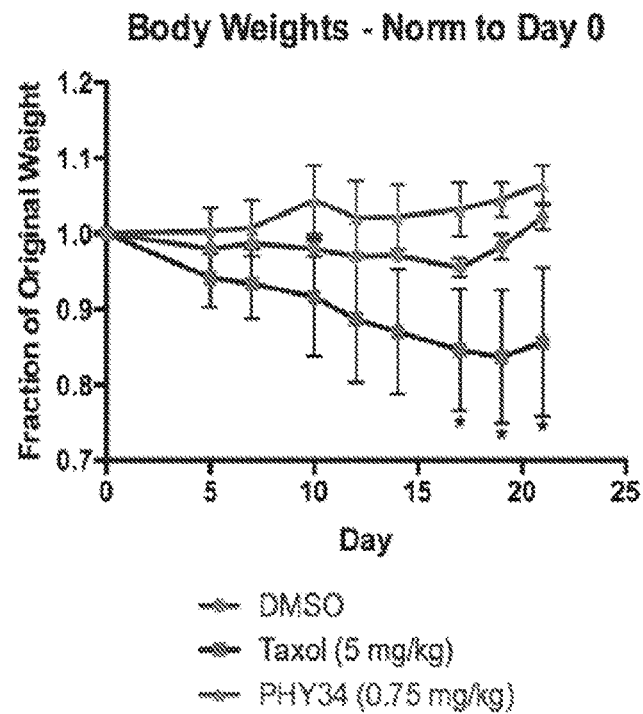
FIG. 12 is a graph showing the toxicity of Taxol or PHY-34 in mice.
Figure 13:
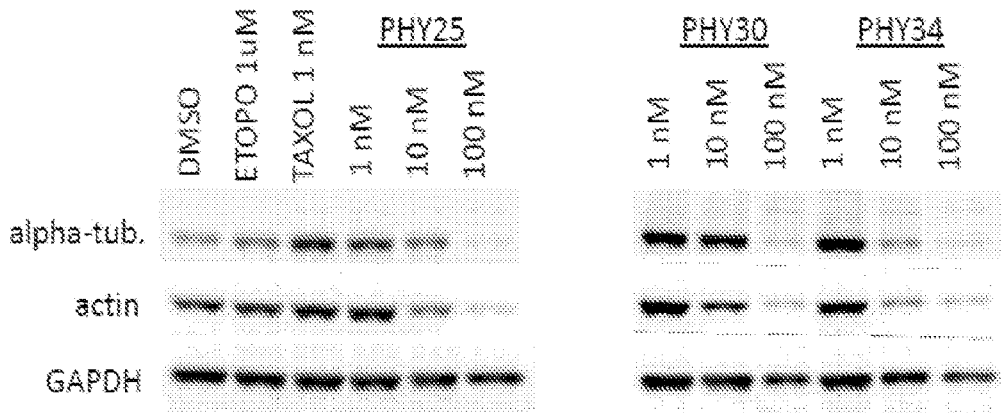
FIG. 13 shows tubulin inhibition for etoposide, Taxol, and various arylnaphthalene ligans.
Figure 13:
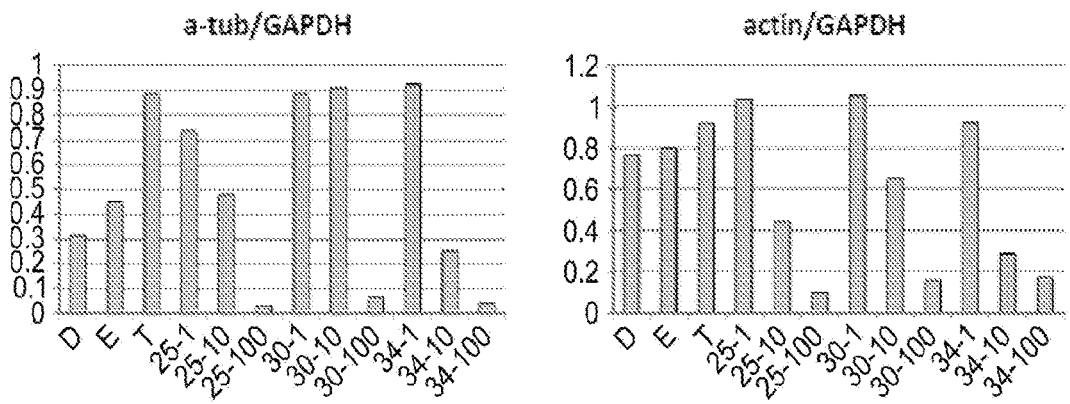
Figure 14:
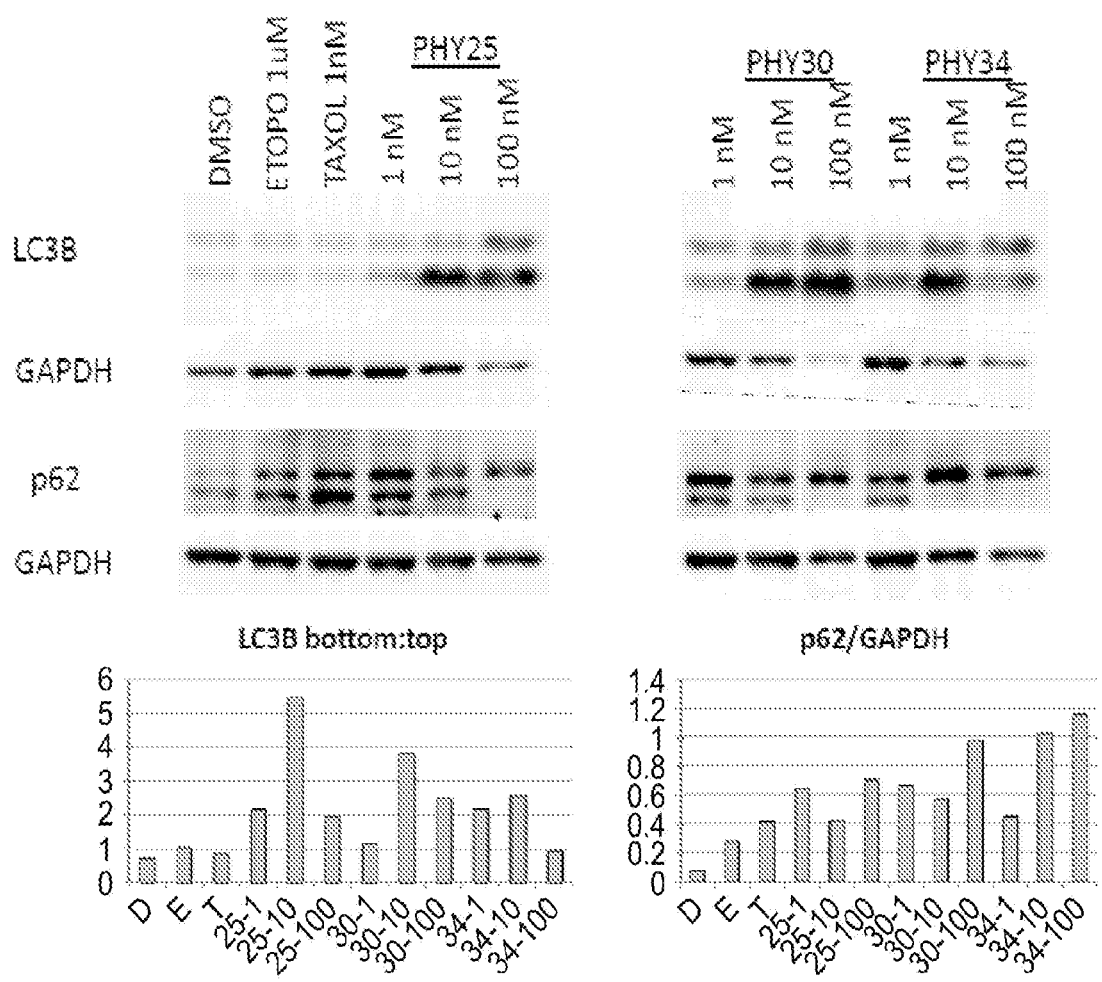
FIG. 14 shows autophagy for etoposide, Taxol, and various arylnaphthalene ligans.

Solubility, Stability, and pK Parameters:

The solubility, maximum tolerated dose, and pharmacokinetics of the phyllanthusmins, facilitating the in vivo studies with PHY-34, were also determined. The solubility of the compounds were assessed in DMSO, PEG300, HPβCD, and PBS. The stability of PHY-34 was assessed in a formulation comprising PEG300 and saline at a 1:1 volume ratio. The solution was prepared at a concentration of 7 mg/ml. A plate reader-based absorbance assay or LC-MS/MS was used. Table 4 summarizes the solubility measurements. FIG. 5 and Table 5 summarize the stability measurements. FIGS. 6A and 6B show the concentration-time profile of PHY-34 in mouse plasma via different administration routes To determine toxicity, PHY-34 was administered to mice by the bolus intravenous (IV), bolus intraperitoneal (IP), or oral (PO) route to the assigned animals. The dosing volume of the compound are given in Table 5.

TABLE 4

Solubility of analogues in various solvents and buffers.

| Compound | MW | Solubility in DMSO (mg/ml) | Solubility in PEG300 (mg/ml) | Solubility in 30% HPβCD (mg/ml) | Solubility in PBS (mg/ml) |
|---|---|---|---|---|---|
| PHY-34 | 582.6 | 114.4 | 27.6 | 1.7 | 0.03 |
| PHY-35 | 610.6 | 86.8 | 25.4 | — | — |
| PHY-37 | 596.6 | 104.0 | 28.7 | 0.6 | — |

—: below the limit of quantitation (0.01 mg/ml)

TABLE 5

Stability of PHY-34.

| RT | 0 hr | 100 | 100 |
|---|---|---|---|
|  | 6 hr | 87 | 82 |
| 4° C. | 1 day | 95 | 77 |
|  | 1 week | 86 | — |
| −20° C. | 1 day | 90 | 82 |
|  | 1 week | 87 | 77 |
| −80° C. | 1 day | 93 | 80 |
|  | 1 week | 86 | 81 |

TABLE 6

Toxicity of PHY-34 as a function of the route of administration.

| Dose (mpk) | IV | IP | PO |
|---|---|---|---|
| 0.3 | all 5 alive | | |
| 0.6 | all 5 alive | all 3 alive | |
| 1 | 1 out of 5 died within 0.5 hour | | |
| 1.8 | | all 5 alive | |
| 3 | all 5 died within 5 minutes | all 3 died within 0.5 | |
| 6 | | all 5 died within 0.5 hour | |
| 30 | | | all 5 alive |
| MTD | 0.6 mpk | 1.8 mpk | >30 mpk | mpk—mg/Kg
MTD—maximum tolerated dose

These studies established reasonable solubility for the phyllanthusmins using PEG300 formulation. PHY-34 solution was shown to be stable (no significant degradation) upon storage for one week at temperatures ranging from 4° C. to −80° C. The MTD of the compound was shown to be 1.8 mpk for IP administration. Interestingly, however, oral dosing showed no toxicity up to 30 mpk even though reasonable AUCs could be achieved through this dosing route.

Hollow fiber assay, IVIS imaging, tubulin inhibition, autophagy, and tumor burden were determined in mice exposed to various arylnaphthalene ligans. The results are summarized in FIGS. 7-14.

The compounds and methods of the appended claims are not limited in scope by the specific compounds and methods described herein, which are intended as illustrations of a few aspects of the claims and any compounds and methods that are functionally equivalent are within the scope of this disclosure. Various modifications of the compounds and methods in addition to those shown and described herein are intended to fall within the scope of the appended claims. Further, while only certain representative compounds, methods, and aspects of these compounds and methods are specifically described, other compounds and methods and combinations of various features of the compounds and methods are intended to fall within the scope of the appended claims, even if not specifically recited. Thus a combination of steps, elements, components, or constituents can be explicitly mentioned herein; however, all other combinations of steps, elements, components, and constituents are included, even though not explicitly stated.

What is claimed is:

1. A compound having a structure according to Formula I or a pharmaceutically acceptable salt or prodrug thereof:

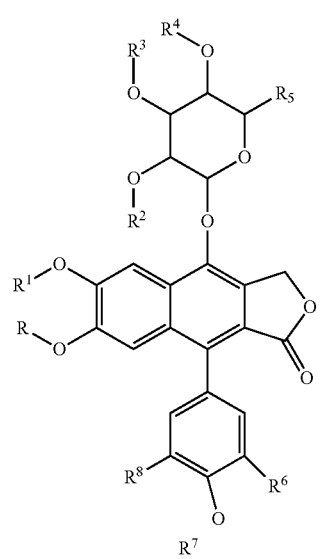

wherein
R, $R^1$, $R^2$, $R^6$, and $R^7$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, R and $R^1$ taken together with the atoms to which they are attached form a substituted or unsubstituted 5 to 7 membered heterocyclic moiety, or $R^6$ and $R^7$ taken together with the atoms to which they are attached form a substituted or unsubstituted 5 to 7 membered heterocyclic moiety;

$R^5$ and $R^8$ are independently hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio;

$R^3$ is hydrogen, halogen, substituted or unsubstituted $C_1$-$C_4$ alkyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and wherein $R^3$ and $R^4$ taken together with the atoms to which they are attached form a substituted or unsubstituted 5 to 7 membered heterocyclic moiety, or $R^4$ and $R^5$ taken together with the atoms to which they are attached form a substituted or unsubstituted 5 to 7 membered heterocyclic moiety;

with the proviso that when $R^4$ and $R^5$ taken together with the atoms to which they are attached form a substituted or unsubstituted 5 to 7 membered heterocyclic moiety, R, $R^1$, and $R^2$ are not all $CH_3$.

2. The compound of claim 1, wherein one or more of R, $R^1$, $R^2$, $R^6$, and $R^7$ are substituted or unsubstituted phosphonyl, substituted or unsubstituted sulfinyl, substituted or unsubstituted sulfonyl, or substituted or unsubstituted sulfonamide.

3. The compound of claim 1, wherein $R^1$ is a substituted or unsubstituted phosphonyl, substituted or unsubstituted sulfinyl, substituted or unsubstituted sulfonyl, or substituted or unsubstituted sulfonamide.

4. The compound of claim 1, wherein R, $R^1$, and $R^2$ are independently hydrogen, substituted or unsubstituted $C_1$-$C_4$ alkyl, substituted or unsubstituted aryl, or substituted or unsubstituted phosphonyl.

5. The compound of claim 4, wherein R, $R^1$, and $R^2$ are independently hydrogen, $CH_3$, or $PO_3H_2$.

6. The compound of claim 1, wherein R and $R^1$ are both $CH_3$.

7. The compound of claim 1, wherein $R^2$ is a substituted or unsubstituted phosphonyl, substituted or unsubstituted sulfinyl, substituted or unsubstituted sulfonyl, or substituted or unsubstituted sulfonamide.

8. The compound of claim 1, wherein $R^2$ is H, $CH_3$, or benzyl.

9. The compound of claim 1, wherein $R^3$ and $R^4$ taken together with the atoms to which they are attached form a substituted or unsubstituted 5 membered heterocyclic moiety or a substituted or unsubstituted 6 membered heterocyclic moiety.

10. The compound of claim 9, wherein the heterocyclic moiety formed by $R^3$ and $R^4$ is substituted with a $C_1$-$C_6$ alkyl, $C_1$-$C_6$ alkoxy, $C_1$-$C_6$ acyl, or phosphonyl.

11. The compound of claim 10, wherein the heterocyclic moiety formed by $R^3$ and $R^4$ is substituted with $CH_3$, $OCH_3$, $C(O)CH_3$, $CO(O)CH_3$, or $PO_3H_2$.

12. The compound of claim 1, wherein $R^5$ is hydrogen, hydroxyl, substituted or unsubstituted $C_1$-$C_6$ alkyl, substituted or unsubstituted $C_1$-$C_4$ alkenyl, substituted or unsubstituted $C_2$-$C_4$ alkynyl, substituted or unsubstituted $C_1$-$C_6$ alkoxy, substituted or unsubstituted $C_1$-$C_6$ alkylhydroxyl, or substituted or unsubstituted $C_1$-$C_6$ ether.

13. The compound of claim 12, wherein $R^5$ is hydrogen, hydroxyl, $OCH_3$, $CH_2OCH_3$, $CH_2OH$ or OCCH.

14. The compound of claim 1, wherein $R^5$ is a substituted or unsubstituted phosphonyl, substituted or unsubstituted sulfinyl, substituted or unsubstituted sulfonyl, or substituted or unsubstituted sulfonamide.

15. The compound of claim 1, wherein $R^6$ and $R^7$ taken together with the atoms to which they are attached form a 5 membered heterocyclic moiety.

16. The compound of claim 1, wherein $R^8$ is hydrogen, substituted or unsubstituted $C_1$-$C_4$ alkyl, or substituted or unsubstituted phosphonyl.

17. The compound of claim 16, wherein $R^8$ is hydrogen, $CH_3$, or $PO_3H_2$.

18. The compound of claim 1, wherein the compound is of Formula I-B, or a pharmaceutically acceptable salt or prodrug thereof:

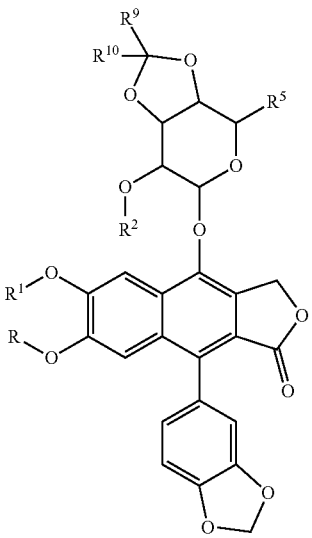

I-B wherein $R^9$ and $R^{10}$ are independently hydrogen, halogen, hydroxyl, substituted or unsubstituted $C_1$-$C_6$ alkyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ alkylhydroxyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, substituted or unsubstituted thio, or $R^9$ and $R^{10}$ taken together with the atoms to which they are attached form a substituted or unsubstituted 5 to 7 membered cyclic moiety.

19. The compound of claim 1, wherein the compound is of Formula I-C, or a pharmaceutically acceptable salt or prodrug thereof:

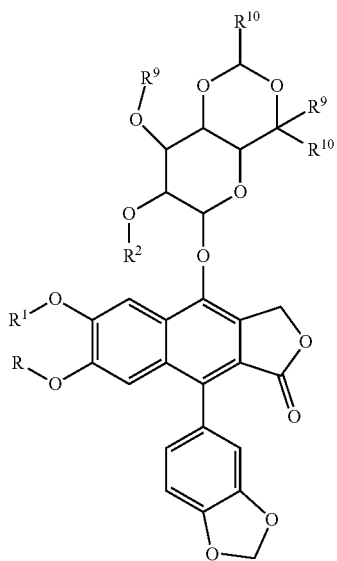

I-C wherein

R[9] and R[10] are independently hydrogen, halogen, hydroxyl, substituted or unsubstituted $C_1$-$C_6$ alkyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ alkylhydroxyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio.

20. The compound of claim 18, wherein R[9] and R[10] are independently hydrogen, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether.

21. The compound of claim 20, wherein R[9] and R[10] are independently hydrogen, $CH_3$, $OCH_3$, $CH_2OCH_3$, or —$CH_2OH$.

22. The compound of claim 1, wherein the compound is of a formula below, or a pharmaceutically acceptable salt or prodrug thereof:

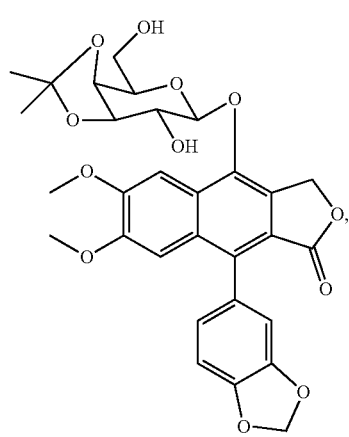

-continued

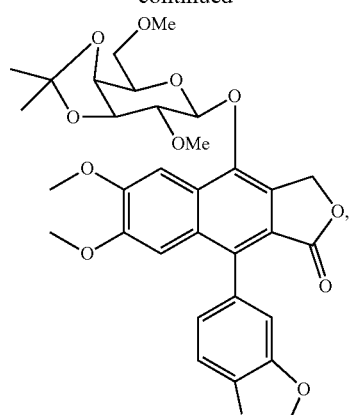

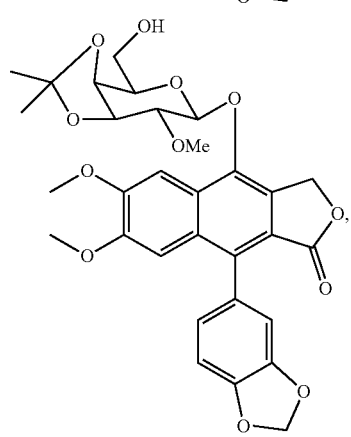

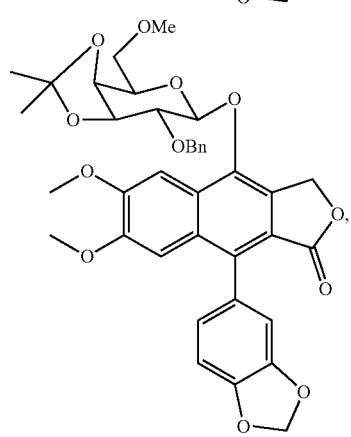

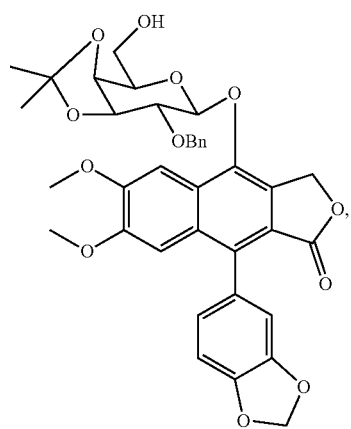

81
-continued
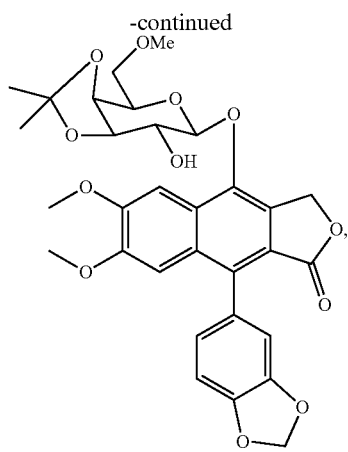
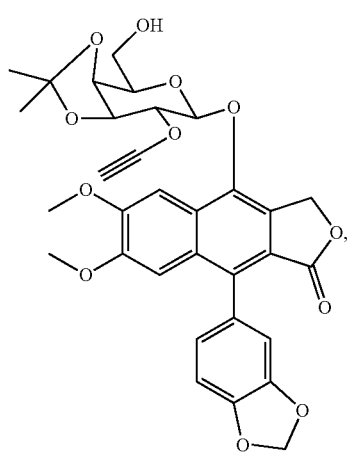
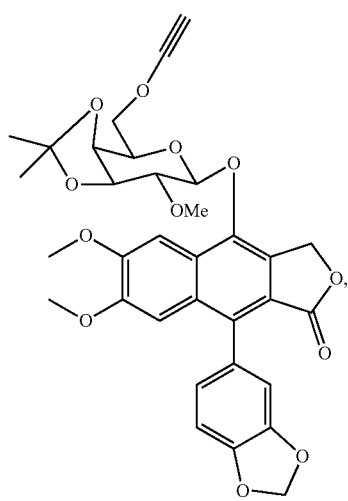
82
-continued
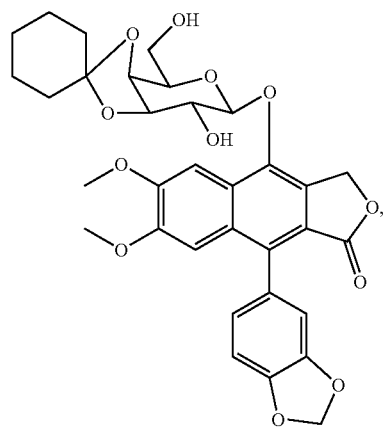
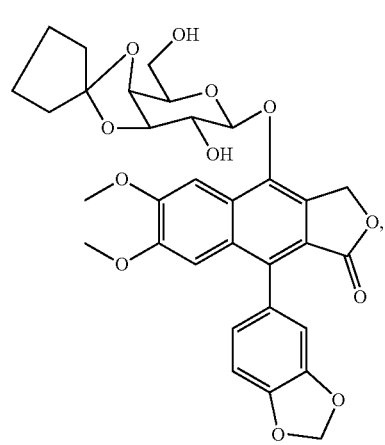
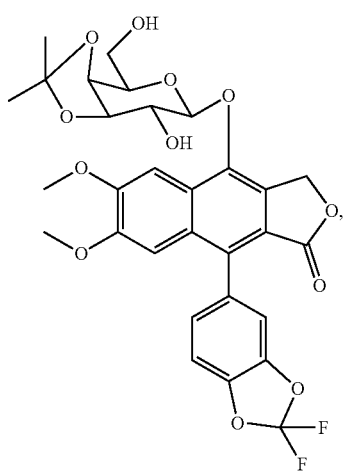

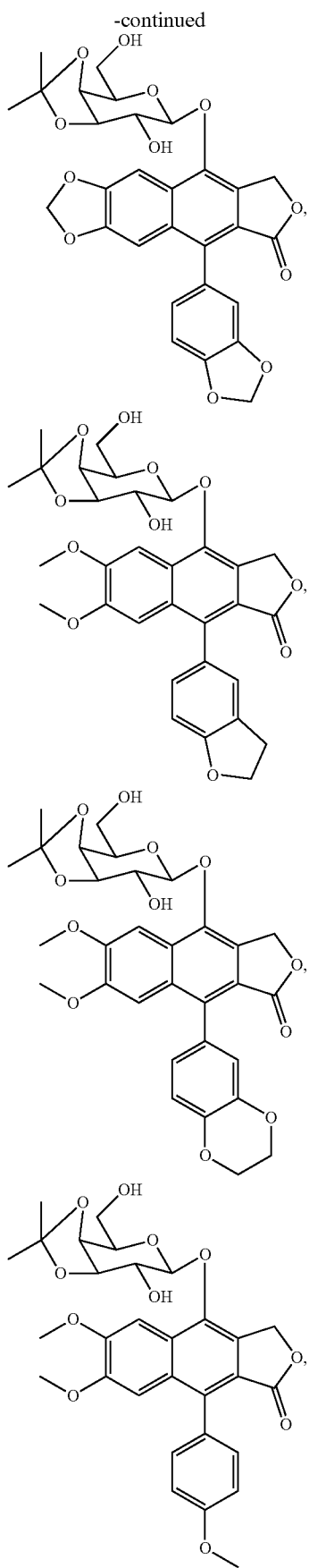
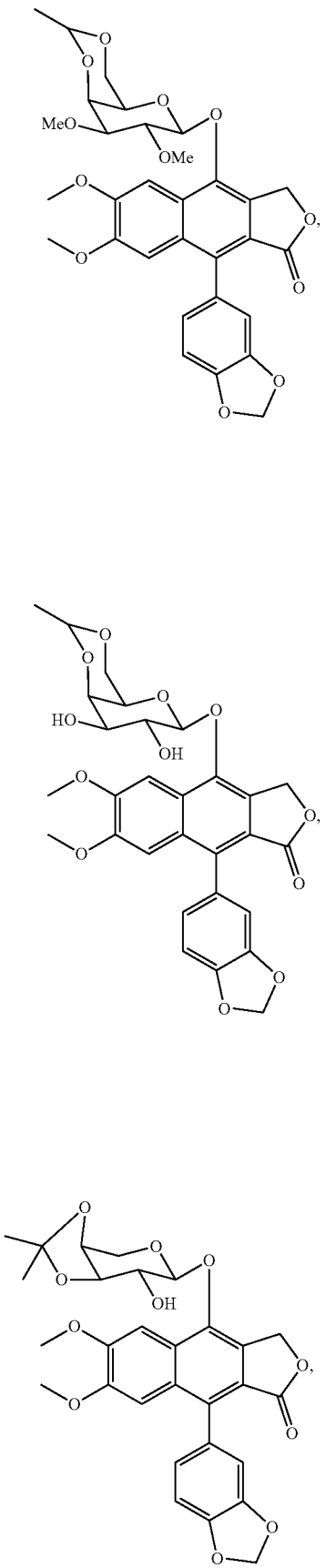

-continued

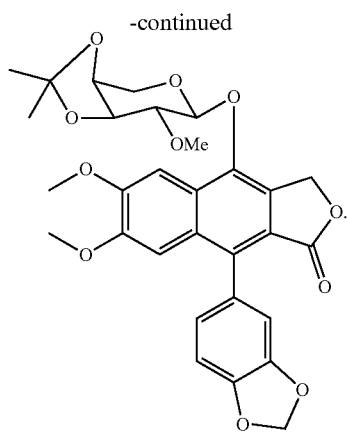

23. A composition compound having a structure according to Formula III or a pharmaceutically acceptable salt or prodrug thereof:

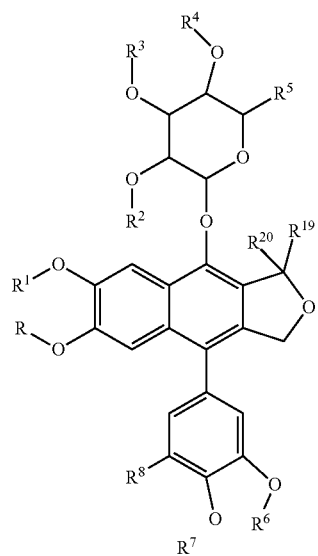

III wherein
R, $R^1$, $R^2$, $R^3$, $R^4$, $R^6$, and $R^7$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, or one or more of R and $R^1$, $R^3$ and $R^4$ or $R^6$ and $R^7$ taken together with the atoms to which they are attached form a substituted or unsubstituted 5 to 7 membered heterocyclic moiety;

$R^5$ and $R^8$ are independently hydrogen, halogen, hydroxyl, substituted or unsubstituted $C_1$-$C_6$ alkyl, substituted or unsubstituted alkenyl, substituted or unsubstituted alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^{19}$ and $R^{20}$ are hydrogen or $R^{19}$ and $R^{20}$ taken together with the atoms to which they are attached form C=O, wherein one or more of R, $R^1$, $R^2$, $R^3$, $R^4$, $R^6$, and $R^7$ are substituted or unsubstituted phosphonyl, substituted or unsubstituted sulfinyl, substituted or unsubstituted sulfonyl, or substituted or unsubstituted sulfonamide.

24. The compound of claim 23, wherein $R^2$, $R^3$, and $R^4$ are independently hydrogen, hydroxyl, substituted or unsubstituted $C_1$-$C_6$ alkyl, or substituted or unsubstituted $C_1$-$C_4$ alkylcarbonyl.

25. The compound of claim 23, wherein $R^5$ and $R^8$ are independently hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether.

26. The compound of claim 23, wherein $R^6$ and $R^7$ taken together with the atoms to which they are attached form a 5 membered heterocyclic moiety.

27. The compound of claim 23, wherein $R^{19}$ and $R^{20}$ are hydrogen.

28. The compound of claim 23, wherein $R^{19}$ and $R^{20}$ taken together with the atoms to which they are attached form C=O.

29. A compound having a structure according to Formula VI or a pharmaceutically acceptable salt or prodrug thereof:

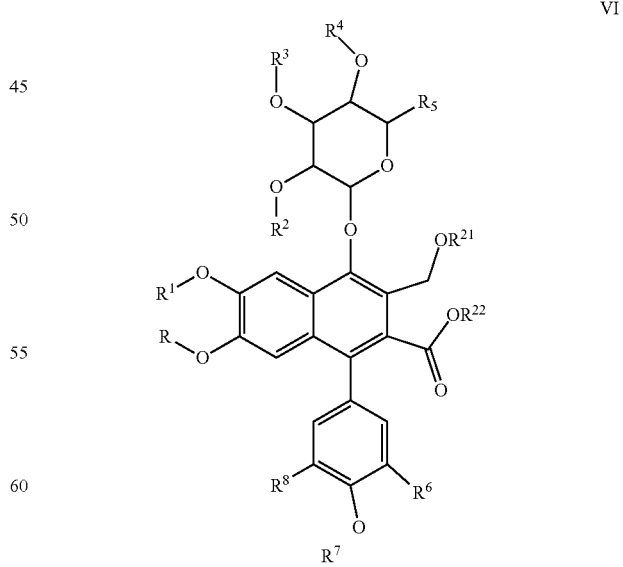

VI wherein
R, $R^1$, $R^2$, $R^6$, $R^7$, $R^{21}$, and $R^{22}$ are independently hydrogen, halogen, substituted or unsubstituted $C_1$-$C_4$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio, R and $R^1$ taken together with the atoms to which they are attached form a substituted or unsubstituted 5 to 7 membered heterocyclic moiety, or $R^6$ and $R^7$ taken together with the atoms to which they are attached form a substituted or unsubstituted 5 to 7 membered heterocyclic moiety;

$R^5$ and $R^8$ are independently hydrogen, halogen, hydroxyl, substituted or unsubstituted $C_1$-$C_6$ alkyl, substituted or unsubstituted $C_2$-$C_4$ alkenyl, substituted or unsubstituted $C_2$-$C_4$ alkynyl, substituted or unsubstituted aryl, substituted or unsubstituted $C_1$-$C_6$ alkylhydroxyl, substituted or unsubstituted $C_1$-$C_6$ alkoxy, substituted or unsubstituted $C_1$-$C_6$ alkoxycarbonyl, hydroxycarbonyl, substituted or unsubstituted $C_1$-$C_6$ acyl, substituted or unsubstituted $C_1$-$C_6$ ether, substituted or unsubstituted amino, substituted or unsubstituted amido, substituted or unsubstituted $C_1$-$C_6$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; and $R^3$ and $R^4$ are independently hydrogen, halogen, substituted or unsubstituted $C_1$-$C_4$ alkyl, substituted or unsubstituted $C_1$-$C_4$ alkoxy, substituted or unsubstituted $C_1$-$C_4$ alkoxycarbonyl, hydroxycarbonyl, substituted or unsubstituted $C_1$-$C_4$ acyl, substituted or unsubstituted amino, substituted or unsubstituted amido, substituted or unsubstituted $C_1$-$C_4$ carbamoyl, substituted or unsubstituted phosphonyl, substituted or unsubstituted sulfinyl, substituted or unsubstituted sulfonyl, substituted or unsubstituted sulfonamide, or substituted or unsubstituted thio; or $R^3$ and $R^4$ taken together with the atoms to which they are attached form a substituted or unsubstituted 5 to 7 membered heterocyclic moiety, or $R^4$ and $R^5$ taken together with the atoms to which they are attached form a substituted or unsubstituted 5 to 7 membered heterocyclic moiety.

30. The compound of claim 29, wherein R and $R^1$ are both $CH_3$.

31. The compound of claim 29, wherein $R^2$ is H or $CH_3$.

32. The compound of claim 29, wherein $R^3$ and $R^4$ taken together with the atoms to which they are attached form a substituted or unsubstituted 5 membered heterocyclic moiety or a substituted or unsubstituted 6 membered heterocyclic moiety.

33. The compound of claim 32, wherein the heterocyclic moiety formed by $R^3$ and $R^4$ is substituted with a $C_1$-$C_6$ alkyl, $C_1$-$C_6$ alkoxy, $C_1$-$C_6$ acyl, or phosphonyl.

34. The compound of claim 29, wherein $R^5$ is hydrogen, hydroxyl, substituted or unsubstituted $C_1$-$C_6$ alkyl, substituted or unsubstituted $C_1$-$C_6$ alkoxy, substituted or unsubstituted $C_1$-$C_6$ alkylhydroxyl, or substituted or unsubstituted $C_1$-$C_6$ ether.

35. The compound of claim 29, wherein $R^5$ is a substituted or unsubstituted phosphonyl, substituted or unsubstituted sulfinyl, substituted or unsubstituted sulfonyl, or substituted or unsubstituted sulfonamide.

36. The compound of claim 29, wherein $R^6$ and $R^7$ taken together with the atoms to which they are attached form a 5 membered heterocyclic moiety.

37. The compound of claim 29, wherein $R^8$ is hydrogen, $CH_3$, or $PO_3H_2$.

38. The compound of claim 29, wherein $R^{21}$ and $R^{22}$ are independent selected from hydrogen or substituted or unsubstituted $C_1$-$C_4$ alkyl.

* * * * *

UNITED STATES PATENT AND TRADEMARK OFFICE
CERTIFICATE OF CORRECTION

PATENT NO. : 10,682,367 B2
APPLICATION NO. : 16/079754
DATED : July 9, 2019
INVENTOR(S) : James Fuchs, Alan Douglas Kinghorn and Andrew Huntsman Page 1 of 1

It is certified that error appears in the above-identified patent and that said Letters Patent is hereby corrected as shown below:

In the Specification

Column 1, Lines 14-19 replace the Government Support Clause with:
--This invention was made with government support under CA125066 awarded by National Institutes of Health. The government has certain rights in the invention.--

Signed and Sealed this
Eleventh Day of August, 2020

Andrei Iancu
*Director of the United States Patent and Trademark Office*